(12) United States Patent
Kheir et al.

(10) Patent No.: US 10,577,554 B2
(45) Date of Patent: *Mar. 3, 2020

(54) GAS-FILLED STABILIZED PARTICLES AND METHODS OF USE

(71) Applicant: Children's Medical Center Corporation, Boston, MA (US)

(72) Inventors: John Kheir, Boston, MA (US); Brian D. Polizzotti, Boston, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/776,774

(22) PCT Filed: Mar. 14, 2014

(86) PCT No.: PCT/US2014/028742
§ 371 (c)(1),
(2) Date: Sep. 15, 2015

(87) PCT Pub. No.: WO2014/144364
PCT Pub. Date: Sep. 18, 2014

(65) Prior Publication Data
US 2016/0030596 A1    Feb. 4, 2016

Related U.S. Application Data

(60) Provisional application No. 61/787,061, filed on Mar. 15, 2013.

(51) Int. Cl.
*C10L 10/18* (2006.01)
*A61K 9/50* (2006.01)
*A61K 47/69* (2017.01)

(52) U.S. Cl.
CPC ............ *C10L 10/18* (2013.01); *A61K 9/5031* (2013.01); *A61K 9/5036* (2013.01); *A61K 47/6925* (2017.08); *A61K 9/5015* (2013.01); *A61K 9/5026* (2013.01)

(58) Field of Classification Search
CPC .... A61K 2300/00; A61K 33/40; A61K 35/14; A61K 49/223; A61K 49/227; A61K 9/1271; A61K 2800/87; A61K 41/0004; A61K 41/0028; A61K 41/0052; A61K 47/6925; A61K 49/1815; A61K 49/22; A61K 8/14; A61K 8/70; A61K 9/127; A61K 9/1277; A61K 9/1278; A61K 2123/00; A61K 47/48869; A61K 47/51; A61K 49/1806; A61K 49/225; A61K 49/226; A61K 51/1258; A61K 8/046; A61K 9/1641; A61K 9/5031; A61M 5/3145; A61Q 19/00; A61F 11/00; A61F 11/08; A61F 11/10; A61F 2011/085; C08G 79/025
See application file for complete search history.

(56) References Cited

U.S. PATENT DOCUMENTS

| | | |
|---|---|---|
| 3,526,481 A | 9/1970 | Rubricius et al. |
| 4,276,885 A | 7/1981 | Tickner et al. |
| 4,446,642 A | 5/1984 | Chap |
| 4,466,442 A | 8/1984 | Hilmann et al. |
| 4,844,882 A | 7/1989 | Widder et al. |
| 4,911,689 A | 3/1990 | Hattler |
| 5,084,011 A | 1/1992 | Grady |
| 5,219,538 A | 6/1993 | Henderson et al. |
| 5,487,390 A * | 1/1996 | Cohen ................. A61K 9/1271 424/501 |
| 5,558,094 A | 9/1996 | Quay |
| 5,573,751 A | 11/1996 | Quay |
| 5,665,383 A | 9/1997 | Grinstaff et al. |
| 5,711,933 A | 1/1998 | Bichon et al. |
| 5,733,572 A * | 3/1998 | Unger ..................... A61K 8/14 424/1.21 |
| 5,827,504 A | 10/1998 | Yan et al. |
| 5,840,275 A | 11/1998 | Bichon et al. |
| 5,863,520 A | 1/1999 | Bichon et al. |
| 5,869,538 A | 2/1999 | Van Liew et al. |
| 5,882,717 A | 3/1999 | Panesar et al. |
| 5,935,553 A | 8/1999 | Unger et al. |
| 6,045,777 A | 4/2000 | Church et al. |
| 6,200,548 B1 | 3/2001 | Bichon et al. |
| 6,210,611 B1 | 4/2001 | Needham et al. |
| 6,261,537 B1 | 7/2001 | Klaveness et al. |

(Continued)

FOREIGN PATENT DOCUMENTS

| | | |
|---|---|---|
| EP | 0 077 752 A2 | 4/1983 |
| EP | 0 699 445 A2 | 3/1996 |

(Continued)

OTHER PUBLICATIONS

Silvay et al. ("Cardiopulmonary Bypass for Adult Patients: A Survey of Equipment and Techniques", Journal of Cardiothoracic and Vascular Anesthesia, vol. 9, Issue 4, Aug. 1995, pp. 420-424).*
Davis et al. ("Topical Oxygen Emulsion: A Novel Wound Therapy", Arch. Dermatol. 2007; 143(10): 1252-1256).*
Sirsi et al. ("Microbubble Compositions, Properties and Biomedical Applications", Bubble Sci Eng Technol, Nov. 2009; 1(1-2); 3-17).*
Xiong et al. (Polymeric microbubbles for ultrasonic molecular imaging and targeted therapeutics, J Biomater Sci Polym Ed. 2011; 22(4-6): 417-28. Doi: 10.1163/092050610X540550, cited by Applicant in IDS filed Aug. 31, 2017) (Year: 2011).*

(Continued)

*Primary Examiner* — Audrea B Coniglio
(74) *Attorney, Agent, or Firm* — Wolf, Greenfield & Sacks, P.C.

(57) ABSTRACT

Provided herein are various gas-filled particles having a stabilized membrane that encapsulates the gas. Pharmaceutical compositions, methods of use and treatment, and methods of preparation are also described.

16 Claims, 27 Drawing Sheets

(56) References Cited

U.S. PATENT DOCUMENTS

| | | | |
|---|---|---|---|
| 6,315,981 | B1 | 11/2001 | Unger |
| 6,333,021 | B1 | 12/2001 | Schneider et al. |
| 6,416,740 | B1 | 7/2002 | Unger |
| 6,443,898 | B1 | 9/2002 | Unger et al. |
| 6,537,246 | B1 | 3/2003 | Unger et al. |
| 6,808,720 | B2 | 10/2004 | Unger |
| 6,844,317 | B2 | 1/2005 | Winslow et al. |
| 7,105,151 | B2 | 9/2006 | Unger et al. |
| 7,122,027 | B2 | 10/2006 | Trescony et al. |
| 7,141,235 | B2 | 11/2006 | Trevino et al. |
| 7,303,156 | B1 | 12/2007 | Kim et al. |
| 8,481,077 | B2 | 7/2013 | Kheir et al. |
| 2002/0155098 | A1* | 10/2002 | Bolton .................. A61K 33/40 424/93.7 |
| 2003/0120204 | A1 | 6/2003 | Unger et al. |
| 2004/0013662 | A1 | 1/2004 | Porter et al. |
| 2005/0260189 | A1 | 11/2005 | Klibanov et al. |
| 2006/0051297 | A1 | 3/2006 | Schneider et al. |
| 2007/0134332 | A1 | 6/2007 | Turnell et al. |
| 2009/0191244 | A1 | 7/2009 | Kheir et al. |
| 2010/0069814 | A1 | 3/2010 | Borgia et al. |
| 2010/0080759 | A1 | 4/2010 | Chang et al. |
| 2010/0158813 | A1 | 6/2010 | Paradossi et al. |
| 2010/0209532 | A1 | 8/2010 | Dube et al. |
| 2011/0207062 | A1 | 8/2011 | McAlister |
| 2012/0156300 | A1 | 6/2012 | Kheir et al. |
| 2012/0175305 | A1 | 7/2012 | Borden et al. |
| 2012/0201900 | A1 | 8/2012 | Borden et al. |
| 2013/0066264 | A1 | 3/2013 | Matsumoto et al. |
| 2014/0010848 | A1 | 1/2014 | Kheir et al. |
| 2014/0057108 | A1 | 2/2014 | Sun et al. |
| 2015/0164787 | A1 | 6/2015 | Kheir et al. |
| 2016/0067276 | A1 | 3/2016 | Polizzotti et al. |

FOREIGN PATENT DOCUMENTS

| | | |
|---|---|---|
| EP | 0 605 477 B2 | 6/2007 |
| EP | 2 253 308 A1 | 11/2010 |
| WO | WO 98/18501 A2 | 5/1988 |
| WO | WO 92/05806 A1 | 4/1992 |
| WO | WO 92/17514 A1 | 10/1992 |
| WO | WO 94/18954 A1 | 9/1994 |
| WO | WO 94/28874 A1 | 12/1994 |
| WO | WO 95/16467 A1 | 6/1995 |
| WO | WO 97/00638 A2 | 1/1997 |
| WO | WO 97/22409 A1 | 6/1997 |
| WO | WO 2004/069284 A2 | 8/2004 |
| WO | WO 2005/063305 A1 | 7/2005 |
| WO | WO2009/043031 A2 * | 4/2009 ............ A61K 47/48 |
| WO | WO 2009/082449 A2 | 7/2009 |
| WO | WO 2011/013032 A2 | 2/2011 |
| WO | WO 2011/034892 A2 | 3/2011 |
| WO | WO2012/065060 A2 * | 5/2012 ............ A61K 47/48 |
| WO | WO 2012/065060 A2 | 5/2012 |
| WO | WO 2015/196065 A1 | 12/2015 |

OTHER PUBLICATIONS

Phong (Properties and hydrolysis of PLGA and PLLA cross-linked with electron beam radiation, Polymer degradation and Stability 95 (2010) 771-777, published Feb. 12, 2010) (Year: 2010).*
Davis et al. ("Topical Oxygen Emulsion: A Novel Wound Therapy", Arch. Dermatol. 2007; 143(10): 1252-1256, previously cited) (Year: 2007).*
Goh et al. ("Alginates as a useful natural polymer for microencapsulation and therapeutic applications", Carbohydrate Polymers 88 (2012) 1-12, published online Nov. 12, 2011).*
U.S. Appl. No. 13/884,658, filed Sep. 24, 2013, Kheir et al.
U.S. Appl. No. 14/390,665, filed Oct. 3, 2014, Kheir et al.
U.S. Appl. No. 14/776,372, filed Sep. 14, 2015, Polizzotti et al.
EP 14763981.9, dated Aug. 4, 2016, Extended European Search Report.
PCT/US2014/028742, dated Jul. 29, 2014, International Search Report and Written Opinion.
PCT/US2014/028742, dated Sep. 24, 2015, International Preliminary Report on Patentability.
Extended European Search Report for European Application No. 14763981.9 dated Aug. 4, 2016.
International Search Report and Written Opinion for Application No. PCT/US2014/028742 dated Jul. 29, 2014.
International Preliminary Report on Patentability for Application No. PCT/US2014/028742 dated Sep. 24, 2015.
[No Author Listed], Acute Myocardial Infarction with HyperOxemic Therapy II (AMIHOT II). Clinical Trials.gov. Last Accessed from http://clinicaltrials.gov/ct2/show/NCT00175058?tern=therox &rank=1 on Nov. 9, 2010. 5 pages.
[No Author Listed], DownStream System. Therox. Last Accessed from http://www.therox.com/products/downstream-system/index.cfm?print on Nov. 9, 2010. 1 page.
Adjei et al., Pulmonary delivery of peptide drugs: effect of particle size on bioavailability of leuprolide acetate in healthy male volunteers. Pharm Res. Jun. 1990;7(6):565-9.
Asai et al., Interaction of soybean oil with phosphatidylcholine and their formation of small dispersed particles. Drug Dev Ind Pharm. May 1999;25(5):643-50.
Baker et al., Hypothermia prevents ischemia-induced increases in hippocampal glycine concentrations in rabbits. Stroke. May 1991;22(5):666-73.
Barnhart et al., Characteristics of Albunex: air-filled albumin microspheres for echocardiography contrast enhancement. Invest Radiol. Sep. 1990;25 Suppl 1:S162-4.
Batchelor et al., The determination of the bulk stress in a suspension of spherical particles to order c2. J Fluid Mech. 1972;56(3):401-27.
Bisazza et al., Microbubble-mediated oxygen delivery to hypoxic tissues as a new therapeutic device. Conf Proc IEEE Eng Med Biol Soc. 2008;2008:2067-70.
Borden et al., Oxygen permeability of fully condensed lipid monolayers. J Phys Chem. 2004:108(19):6009-16.
Borden et al., A stimulus-responsive contrast agent for ultrasound molecular imaging. Biomaterials. Feb. 2008;29(5):597-606. Epub Oct. 30, 2007.
Borden et al., Dissolution behavior of lipid monolayer-coated, air filled microbubbles: Effect of lipid hydrophobic chain length. Langmuir. 2002;18(24):9225-33.
Borden et al., Influence of lipid shell physicochemical properties on ultrasound-induced microbubble destruction. IEEE Trans Ultrason Ferroelectr Freq Control. Nov. 2005;52(11):1992-2002.
Borden et al., Lateral phase separation in lipid-coated microbubbles. Lateral phase separation in lipid-coated microbubbles. Langmuir. Apr. 25, 2006;22(9):4291-7.
Borden et al., Physico-chemical properties of the microbubble lipid shell. IEEE Transactions on Ultrasonics Ferroelectrics and Frequency Control, Montreal, Canada (2004).
Borden et al., Surface phase behavior and microstructure of lipid/PEG-emulsifier monolayer-coated microbubbles. Colloids Surf B Biointerfaces. Jun. 1, 2004;35(3-4):209-23.
Brancewicz et al., Hydrophobic gas bubble formation in definity (R): a freeze fracture electron microscopy study. J Dispersion Sci Tech. 2006;27(5):761-5.
Brezis et al., Hypoxia of the renal medulla—its implications for disease. N Engl J Med. Mar. 9, 1995;332(10):647-55.
Bucana et al., Preservation of multilamellar lipid vesicles (liposomes) for ultrastructural studies. Scan Electron Microsc. 1983;(Pt 3):1329-37.
Burkhard et al., Oxygen transport to tissue by persistent bubbles: theory and simulations. J Appl Physiol. 1994;77(6):2874-8.
Cabrales et al., Early difference in tissue pH and microvascular hemodynamics in hemorrhagic shock resuscitation using polyethylene glycol-albumin- and hydroxyethyl starch-based plasma expanders. Shock. Jul. 2005;24(1):66-73.
Cabrales et al., Extreme hemodilution with PEG-hemoglobin vs. PEG-albumin. Am J Physiol Heart Circ Physiol. Dec. 2005;289(6):H2392-400. Epub Jul. 15, 2005.
Choi et al., Liposomes and niosomes as topical drug delivery systems. Skin Pharmacol Physiol. Sep.-Oct. 2005;18(5):209-19. Epub Jul. 5, 2005.

(56) References Cited

OTHER PUBLICATIONS

Choi et al., Noninvasive, transcranial and localized opening of the blood-brain barrier using focused ultrasound in mice. Ultrasound Med Biol. Jan. 2007;33(1):95-104.

Cortesi et al., Sugar cross-linked gelatin for controlled release: microspheres and disks. Biomaterials. Sep. 1998;19(18):1641-9.

Dewall et al., A simple, expendable, artificial oxygenator for open heart surgery. Surg Clin North Am. Aug. 1956:1025-34.

Diebel et al., Right ventricular response after myocardial contusion and hemorrhagic shock. Surgery. Oct. 1993;114(4):788-92; discussion 793.

Dressaire et al., Interfacial polygonal nanopatterning of stable microbubbles. Science. May 30, 2008;320(5880):1198-201.

Dubourg et al., Failure of the loop diuretic torasemide to improve renal function of hypoxemic vasomotor nephropathy in the newborn rabbit. Pediatr Res. Apr. 2000;47(4 Pt 1):504-8.

Duncan et al., Test of the Epstein-Plesset model for gas microparticle dissolution in aqueous media: effect of surface tension and gas undersaturation in solution. Langmuir. Mar. 30, 2004;20(7):2567-78.

Elberger et al., Double-labeling of tissue containing the carbocyanine dye DiI for immunocytochemistry. J Histochem Cytochem. May 1990;38(5):735-9.

El-Desoky et al., Effect of graded hypoxia on hepatic tissue oxygenation measured by near infrared spectroscopy. J Hepatol. Jul. 1999;31(1):71-6.

Epstein et al., On the stability of gas bubbles in liquid-gas solutions. J Chem Phys. 1950;18(11):1505-9.

Farook et al., Microbubbling by co-axial electrohydrodynamic atomization. Med Biol Eng Comput. Aug. 2007;45(8):781-9. Epub Jul. 12, 2007.

Farook et al., Preparation of microbubble suspensions by co-axial electrohydrodynamic atomization. Med Eng Phys. Sep. 2007;29(7):749-54. Epub Oct. 10, 2006.

Feinstein et al., Microbubble dynamics visualized in the intact capillary circulation. J Am Coll Cardiol. Sep. 1984;4(3):595-600.

Feinstein, The powerful microbubble: from bench to bedside, from intravascular indicator to therapeutic delivery system, and beyond. Am J Physiol Heart Circ Physiol. Aug. 2004;287(2):H450-7.

Ferrara et al., Ultrasound microbubble contrast agents: fundamentals and application to gene and drug delivery. Annu Rev Biomed Eng. 2007;9:415-47.

Feshitan et al., Microbubble size isolation by differential centrifugation. J Colloid Interface Sci. Jan. 15, 2009;329(2):316-24. doi: 10.1016/j.jcis.2008.09.066. Epub Oct. 1, 2008.

Fuchs et al., Ischemic hepatitis: clinical and laboratory observations of 34 patients. J Clin Gastroenterol. Apr. 1998;26(3):183-6.

Gerber et al., Long lived microbubbles for oxygen delivery. Artif Cells Blood Substit Immobil Biotechnol. 2007;35(1):119-24.

Hansel et al., Metabolic syndrome is associated with elevated oxidative stress and dysfunctional dense high-density lipoprotein particles displaying impaired antioxidative activity. J Clin Endocrinol Metab. Oct. 2004;89(10):4963-71.

Hattler et al., A respiratory gas exchange catheter: in vitro and in vivo tests in large animals. J Thorac Cardiovasc Surg. Sep. 2002;124(3):520-30.

Hernot et al., Microbubbles in ultrasound-triggered drug and gene delivery. Adv Drug Deliv Rev. Jun. 30, 2008;60(10):1153-66. Epub Apr. 3, 2008.

Jones et al., Demonstration of nonperfused myocardium in late hemorrhagic shock. Circ Shock. 1978;5(2):97-104.

Karlsson et al., Dynamics of hepatic enzyme activity following birth asphyxia. Acta Paediatr. Nov. 2006;95(11):1405-11.

Kaya et al., Changes in lipid-encapsulated microbubble population during continuous infusion and methods to maintain consistency. Ultrasound Med Biol. Oct. 2009;35(10):1748-55. doi: 10.1016/j.ultrasmedbio.2009.04.023. Epub Jul. 26, 2009.

Kheir et al., Bulk manufacture of concentrated oxygen gas-filled microparticles for intravenous oxygen delivery. Adv Healthc Mater. Aug. 2013;2(8):1131-41. doi: 10.1002/adhm.201200350. Epub Mar. 8, 2013.

Kheir et al., Novel oxygen-bearing nanoparticles provide dose-dependent oxygen delivery. Critic Care Medic. 2007;35(12):A16-16.

Kim et al., Artificial oxygen carriers as red blood cell substitutes: a selected review and current status. Artif Organs. Sep. 2004;28(9):813-28.

Kim et al., Mechanical properties and microstructure of polycrystalline phospholipid monolayer shells: novel solid microparticles. Langmuir. 2003;19(20):8455-66.

Kim et al., New protocols for preparing dipalmitoylphosphatidylcholine dispersions and controlling surface tension and competitive adsorption with albumin at the air/aqueous interface. Colloids Surf B Biointerfaces. Jul. 10, 2005;43(3-4):256-66.

Kim, Mechanical properties, microstructure, and specific adhesion of phospholipid monolayer-coated microbubbles. Ph.D. Dissertation, Duke University, (1999).

Klemcke et al., Is survival time after hemorrhage a heritable, quantitative trait?: an initial assessment. Shock. Jun. 2008;29(6):748-53.

Klibanov et al., Amphipathic polyethyleneglycols effectively prolong the circulation time of liposomes. FEBS Lett. Jul. 30, 1990;268(1):235-7.

Klibanov et al., Ultrasound contrast agents: development of the field and current status. Topics Curr Chem. 2002;222:1-34.

Kohane et al., A re-examination of tetrodotoxin for prolonged duration local anesthesia. Anesthesiology. Jul. 1998;89(1):119-31.

Kohane et al., Sciatic nerve blockade in infant, adolescent, and adult rats: a comparison of ropivacaine with bupivacaine. Anesthesiology. Nov. 1998;89(5):1199-208; discussion 10A.

Kuhl et al., Modulation of interaction forces between bilayers exposing short-chained ethylene oxide headgroups. Biophys J. May 1994;66(5):1479-88.

Kvale et al., Size fractionation of gas-filled microspheres by flotation. Separations Technol. 1996;6(4):219-26.

Laine et al., Polyethylene glycol nephrotoxicity secondary to prolonged high-dose intravenous lorazepam. Ann Pharmacother. Nov. 1995;29(11):1110-4.

Ledingham, Heart failure in experimental refractory shock. Eur J Intensive Care Med. Nov. 1976;2(3):111-7.

Leonov et al., Extending the golden hour of hemorrhagic shock tolerance with oxygen plus hypothermia in awake rats. An exploratory study. Resuscitation. Feb. 2002;52(2):193-202.

Li et al., Acoustic emulsification Part 1. Instability of oil-water interface to form initial droplets. J Fluid Mech. 1978;88(Oct):499-511.

Li et al., Acoustic Emulsification Part 2. Breakup of large primary oil droplets in a water medium. J Fluid Mech. 1978;88(Oct):513-28.

Lindner, Microbubbles in medical imaging: current applications and future directions. Nat Rev Drug Discov. Jun. 2004;3(6):527-32.

Lum et al., Ultrasound radiation force enables targeted deposition of model drug carriers loaded on microbubbles. J Control Release. Mar. 10, 2006;111(1-2):128-34. Epub Dec. 27, 2005.

Lundgren et al., Intravascular fluorocarbon-stabilized microbubbles protect against fatal anemia in rats. Artif Cells Blood Substit Immobil Biotechnol. 2006;34(5):473-86.

Masters et al., Prolonged regional nerve blockade by controlled release of local anesthetic from a biodegradable polymer matrix. Anesthesiology. Aug. 1993;79(2):340-6.

Mclure et al., Review of local anaesthetic agents. Minerva Anestesiol. Mar. 2005;71(3):59-74.

Meade et al., Ventilation strategy using low tidal volumes, recruitment maneuvers, and high positive end-expiratory pressure for acute lung injury and acute respiratory distress syndrome: a randomized controlled trial. JAMA. Feb. 13, 2008;299(6):637-45.

Meure et al., Conventional and dense gas techniques for the production of liposomes: a review. AAPS PharmSciTech. 2008;9(3):798-809. doi: 10.1208/s12249-008-9097-x. Epub Jul. 3, 2008.

(56) References Cited

OTHER PUBLICATIONS

Mezzetti et al., Oxidative stress and cardiovascular complications in diabetes: isoprostanes as new markers on an old paradigm. Cardiovasc Res. Aug. 18, 2000;47(3):475-88.
Mulholland et al., Investigation and quantification of the blood trauma caused by the combined dynamic forces experienced during cardiopulmonary bypass. Perfusion. Nov. 2000;15(6):485-94.
O'Neill et al., Acute Myocardial Infarction with Hyperoxemic Therapy (AMIHOT): a prospective, randomized trial of intracoronary hyperoxemic reperfusion after percutaneous coronary intervention. J Am Coll Cardiol. Jul. 31, 2007;50(5):397-405. Epub Jul. 16, 2007.
Pancholi et al., Generation of microbubbles for diagnostic and therapeutic applications using a novel device. J Drug Target. Jul. 2008;16(6):494-501. doi: 10.1080/10611860802184884.
Pancholi et al., Novel methods for preparing phospholipid coated microbubbles. Eur Biophys J. Apr. 2008;37(4):515-20. Epub Aug. 9, 2007.
Pu et al., Collapse and shedding transitions in binary lipid monolayers coating microbubbles. Langmuir. Mar. 28, 2006;22(7):2993-9.
Pu et al., Effect of microstructure on molecular oxygen permeation through condensed phospholipid monolayers. J Am Chem Soc. May 11, 2005;127(18):6524-5.
Ryter et al., Heme oxygenase-1/carbon monoxide: from basic science to therapeutic applications. Physiol Rev. Apr. 2006;86(2):583-650.
Sakai et al., Hemoglobin-vesicles as oxygen carriers: influence on phagocytic activity and histopathological changes in reticuloendothelial system. Am J Pathol. Sep. 2001;159(3):1079-88.
Scholz, Mechanisms of (local) anaesthetics on voltage-gated sodium and other ion channels. Br J Anaesth. Jul. 2002;89(1):52-61.
Schubert et al., Using microbubbles to oxygenate blood: possible? Engineering in Medicine and Biology Society, 2003. Proceedings of the 25" Annual International Conference of the IEEE, 1(17-21):431-34 (2003).
Stieger et al., Enhancement of vascular permeability with low-frequency contrast-enhanced ultrasound in the chorioallantoic membrane model. Radiology. Apr. 2007;243(1):112-21.
Suslick et al., Acoustic Cavitation and Its Chemical Consequences. Phil. Trans. Roy. Soc. A. 1999;357:335-353.
Swanson et al., Phospholipid-stabilized microbubble foam for injectable oxygen delivery. Langmuir. Oct. 19, 2010;26(20):15726-9. doi: 10.1021/la1029432.
Takalkar et al., Binding and detachment dynamics of microbubbles targeted to P-selectin under controlled shear flow. J Control Release. May 18, 2004;96(3):473-82.
Takasu et al., Effects of increased oxygen breathing in a volume controlled hemorrhagic shock outcome model in rats. Resuscitation. Aug. 1, 2000;45(3):209-20.
Talu et al., Lipid-stabilized monodispersed microbubbles produced by flow focusing for use as ultrasound contrast agents. Ultrasonics Symposium, 2006 IEEE. 2006;2-6:1568-71.
Talu et al., Long-term stability by lipid coating monodisperse microbubbles formed by a flow-focusing device. Langmuir. Nov. 7, 2006;22(23):9487-90.
Talu et al., Maintaining monodispersity in a microbubble population formed by flow-focusing. Langmuir. Mar. 4, 2008;24(5):1745-9. Epub Jan. 19, 2008.
Talu et al., Tailoring the size distribution of ultrasound contrast agents: possible method for improving sensitivity in molecular imaging. Mol Imaging. Nov.-Dec. 2007;6(6):384-92.
Tayar et al., Severe hyperosmolar metabolic acidosis due to a large dose of intravenous lorazepam. N Engl J Med. Apr. 18, 2002;346(16):1253-4.
Taylor, Ostwald ripening in emulsions. Advances in Colloid and Interface Science. 1998;75(2):107-63.
Tracy et al., A method to fix lipids for staining fat embolism in paraffin sections. Histopathology. Jul. 2002;41(1):75-9.
Unger et al., Acoustically active liposheres containing paclitaxel: a new therapeutic ultrasound contrast agent. Invest Radiol. Dec. 1998;33(12):886-92.
Unger et al., Therapeutic applications of lipid-coated microbubbles. Adv Drug Deliv Rev. May 7, 2004;56(9):1291-314.
Vercherat et al., Stra13 regulates oxidative stress mediated skeletal muscle degeneration. Hum Mol Genet. Nov. 15, 2009;18(22):4304-16. doi: 10.1093/hmg/ddp383. Epub Aug. 13, 2009.
Wheatley et al., Surfactant-stabilized contrast agent on the nanoscale for diagnostic ultrasound imaging. Ultrasound Med Biol. Jan. 2006;32(1):83-93.
Winslow et al., Comparison of PEG-modified albumin and hemoglobin in extreme hemodilution in the rat. J Appl Physiol. Oct. 2004;97(4):1527-34. Epub Jun. 18, 2004.
Wu et al., Ultrasound, cavitation bubbles and their interaction with cells. Adv Drug Deliv Rev. Jun. 30, 2008;60(10):1103-16. Epub Apr. 8, 2008.
Xu et al., Controllable gas-liquid phase flow patterns and monodisperse microbubbles in a microfluidic T-junction device. Applied Physics Letters. 2006;88(13).
Zanen et al., The optimal particle size for parasympathicolytic aerols in mild asthmatics. Int J Pharm. 1995;114:111-5.
Zhao et al., Preparation, characterization and in vivo observation of phospholipid-based gas-filled microbubbles containing hirudin. Ultrasound Med Biol. Sep. 2005;31(9):1237-43.
Zhao et al., Radiation-force assisted targeting facilitates ultrasonic molecular imaging. Mol Imaging. Jul. 2004;3(3):135-48.
Sevitt, A review of the complications of burns, their origin and importance for illness and death. J Trauma. May 1979;19(5):358-69. Abstract Only.
Xiong et al., Polymeric microbubbles for ultrasonic molecular imaging and targeted therapeutics. J Biomater Sci Polym Ed. 2011;22(4-6):417-28. doi: 10.1163/092050610X540440.
Ferenz et al., Safety of poly (ethylene glycol)-coated perfluorodecalin-filled poly (lactide-co-glycolide) microcapsules following intravenous administration of high amounts in rats. Results Pharma Sci. Apr. 30, 2014;4:8-18. doi: 10.1016/j.rinphs.2014.04.001. eCollection 2014.
Kutscher et al., Threshold size for optimal passive pulmonary targeting and retention of rigid microparticles in rats. J Control Release. Apr. 2, 2010;143(1):31-7. doi: 10.1016/j.jconrel.2009.12.019. Epub Jan. 5, 2010. (Author Manuscript).
Paefgen et al., Evolution of contrast agents for ultrasound imaging and ultrasound-mediated drug delivery. Front Pharmacol. Sep. 15, 2015;6:197. doi: 10.3389/fphar.2015.00197. eCollection 2015.
Seekell et al., Oxygen delivery using engineered microparticles. Proc Natl Acad Sci U S A. Nov. 1, 2016;113(44):12380-12385. Epub Oct. 17, 2016.
Span et al., Engineered microparticles delivering oxygen to enhance radiotherapy efficacy. Proc Natl Acad Sci U S A. Dec. 13, 2016;113(50):E8009. Epub Dec. 7, 2016.
Spiess, Perfluorocarbon emulsions as a promising technology: a review of tissue and vascular gas dynamics. J Appl Physiol (1985). Apr. 2009;106(4):1444-52. doi: 10.1152/japplphysiol.90995.2008. Epub Jan. 29, 2009.
Teraphongphom et al., Nanoparticle Loaded Polymeric Microbubbles as Contrast Agents for Multimodal Imaging. Langmuir. Nov. 3, 2015;31(43):11858-67. doi: 10.1021/acs.langmuir.5b03473. Epub Oct. 16, 2015. (Author Manuscript).
Zagorski et al., Chemokines accumulate in the lungs of rats with severe pulmonary embolism induced by polystyrene microspheres. J Immunol. Nov. 15, 2003;171(10):5529-36.
Bauer et al., Perfluorocarbon-filled poly(lactide-co-gylcolide) nano- and microcapsules as artificial oxygen carriers for blood substitutes: a physico-chemical assessment. J Microencapsul. 2010;27(2):122-32. doi: 10.3109/02652040903052002.
Cravotto et al., On the mechanochemical activation by ultrasound. Chem Soc Rev. Sep. 21, 2013;42(18):7521-34. doi: 10.1039/c2cs35456j.
De Jong et al., Basic acoustic properties of microbubbles. Echocardiography. Apr. 2002;19(3):229-40.
Feshitan et al., Systemic oxygen delivery by peritoneal perfusion of oxygen microbubbles. Biomaterials. Mar. 2014;35(9):2600-6. doi: 10.1016/j.biomaterials.2013.12.070. Epub Jan. 15, 2014.
Hornig et al., Synthetic polymeric nanoparticles by nanoprecipitation. J. Mater. Chem. 19, 3838-3840; 2009.

(56) References Cited

OTHER PUBLICATIONS

Kheir et al., Oxygen gas-filled microparticles provide intravenous oxygen delivery. Sci Transl Med. Jun. 27, 2012;4(140):140ra88. doi: 10.1126/scitranslmed.3003679.
Korin et al., Shear-activated nanotherapeutics for drug targeting to obstructed blood vessels. Science. Aug. 10, 2012;337(6095):738-42. doi: 10.1126/science.1217815. Epub Jul. 5, 2012. Erratum in: Science. Sep. 21, 2012;337(6101):1453.
Liebert et al., Nanoparticles on the basis of highly functionalized dextrans. J Am Chem Soc. Aug. 3, 2005;127(30):10484-5.
Pekkanen et al., Nanoparticle enhanced optical imaging and phototherapy of cancer. J Biomed Nanotechnol. Sep. 2014;10(9):1677-712.
Sagi et al., Self-immolative polymers. J Am Chem Soc. Apr. 23, 2008;130(16):5434-5. doi: 10.1021/ja801065d. Epub Apr. 1, 2008.
PCT/US2018/020305, Apr. 23, 2018, Invitation to Pay Additional Fees.

* cited by examiner

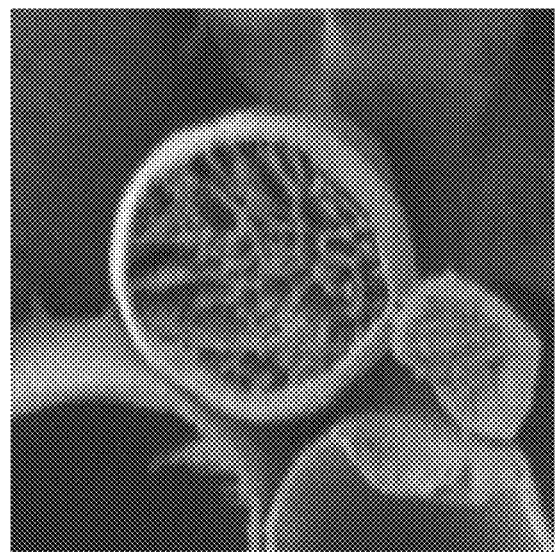
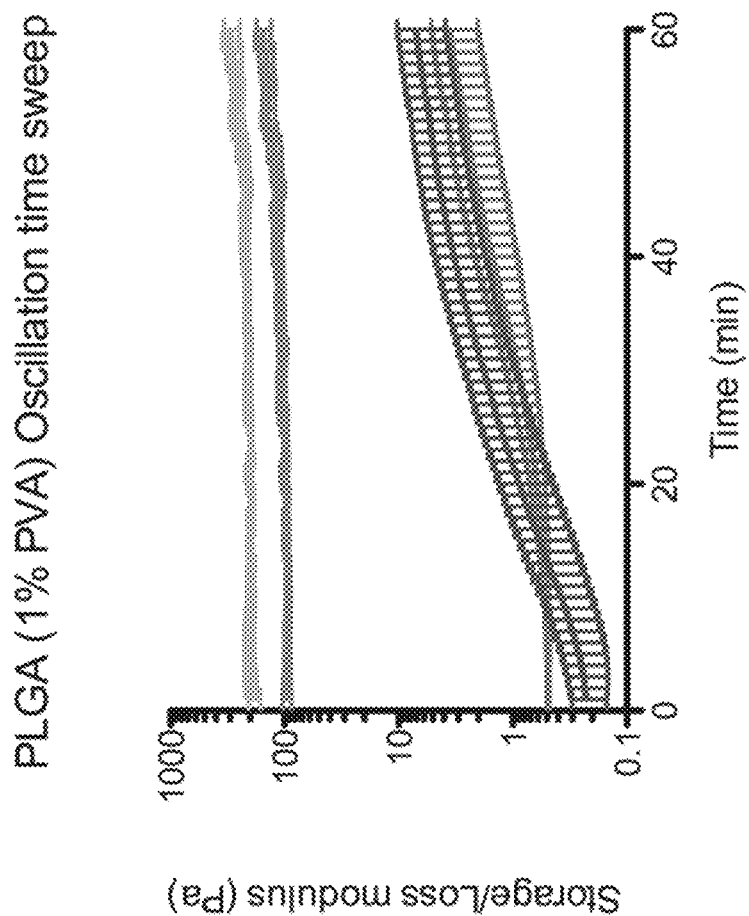
FIG. 14B
FIG. 14A

Interaction Profiles

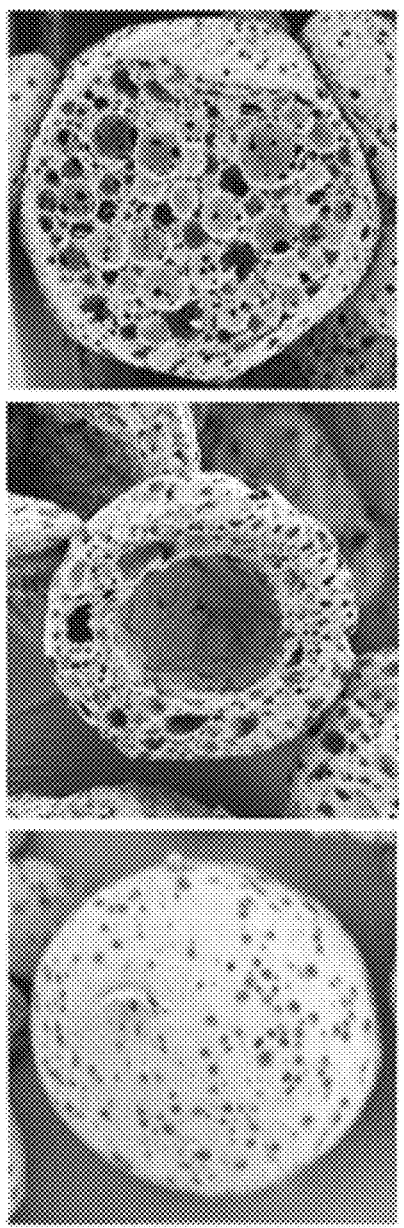
FIG. 21B
FIG. 21A
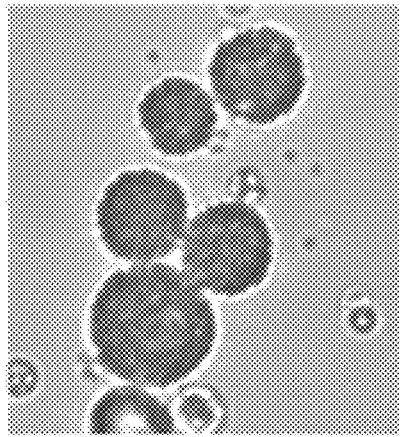
| Predicted Transformation Size (microns) | Predicted Actual Particle Size (microns) | Actual Particle Size (microns) |
|---|---|---|
| 5.25 | 5.78857042 | 5.41 |
| Predicted Transformation Yield (%) | Predicted Actual Yield (%) | Actual Yield (%) |
|---|---|---|
| 0.625308 | 65.3380228 | 68.7 |
FIG. 21C

GAS-FILLED STABILIZED PARTICLES AND METHODS OF USE

RELATED APPLICATIONS

This application is a national stage filing under U.S.C. § 371 of PCT International Application PCT/US2014/028742, entitled "GAS-FILLED STABILIZED PARTICLES AND METHODS OF USE", with an international filing date of Mar. 14, 2014, which claims priority under 35 U.S.C. § 119(e) to U.S. Provisional Application Ser. No. 61/787,061, entitled "GAS-FILLED STABILIZED PARTICLES AND METHODS OF USE" filed on Mar. 15, 2013, which are herein incorporated by reference in their entirety.

GOVERNMENT SUPPORT

This invention was made with government support under grant number W81XWH-11-2-0041 awarded by the U.S. Department of the Army. The Government has certain rights in the invention.

BACKGROUND

All human cells require a constant oxygen supply to maintain cellular structure and function. When oxygen delivery decreases below Pasteur's point, cells undergo anaerobic respiration. Clinically, this can lead to critical organ dysfunction (e.g., brain and myocardial injury), which could result in death if not rapidly corrected. Impairments in oxygen supply can occur during airways obstruction, parenchymal lung disease, or impairments in pulmonary blood flow, circulation, blood oxygen content, and oxygen uptake. Brief interruptions in ventilation or pulmonary blood flow can cause profound hypoxemia, leading to organ injury and death in critically ill subjects.

Providing even a small amount of oxygen supply may significantly reduce the death rate or the severity of tissue damage in subjects suffering from hypoxia. One conventional attempt to restore the oxygen level in a patient is supportive therapy of patient's respiratory system (e.g., mechanical ventilation). This approach may be insufficient to fully reverse hypoxemia in patients with lung injury. Emergency efforts such as lung recruitment maneuvers, increased fraction of inspired oxygen or inhalational nitric oxide are other approaches used to deliver oxygen to a patient. However, in some instances these may be inadequate and/or require too long to take effect due to lack of an adequate airway or overwhelming lung injury.

SUMMARY

Previous work has established the possibility of encapsulating a gas, such as oxygen, in a microbubble with a lipid outer membrane and a gas core for therapeutic delivery of the gas to a subject. For example, previous work has established that administering to asphyxial subjects oxygen-filled microparticles via intravenous injection successfully restores oxygen supply in the subject, preserves spontaneous circulation during asphyxia, and reduces occurrence of cardiac arrest. When administered to the subject, the lipid particles were able to immediately release the gas core into the blood based on the properties of the lipid outer membrane. See, e.g., US Publication No. 2009/0191244 and PCT Application Publication No. WO 2012/065060, incorporated herein by reference.

It was discovered, quite surprisingly, according to the invention, that stabilized particles encapsulating one or more gases in stabilized membranes such as a polymeric or crosslinked lipid membrane are useful for delivering gas to a subject for therapeutic and diagnostic purposes. The particles of the invention are stabilized, for example, by covalently or non-covalently crosslinking one or more components of the stabilized membrane that encapsulates the gas to form a crosslinked stabilized membrane; by covalently or non-covalently crosslinking one or more components of an stabilized membrane, and/or by the use of one or more stabilizing agents as a component of the stabilized membrane or sheath membrane to further stabilize the membrane. See, e.g., FIG. 1. The particles of the invention have a number of enhanced properties over the prior art microbubbles. For instance the particles of the invention have improved shelf life and stability, and thus are more readily available in a number of commercial settings. As a result of improved particle strength, the particles may also be loaded with gas under pressurized conditions. The particles containing pressurized gas have a higher percentage of gas per volume and can be administered in lower volumes to a subject or a higher quantity of gas may be administered to a subject than could be administered using non-pressurized gas particles. Additionally particles having an improved size distribution can be prepared according to the invention.

Thus, in one aspect, provided is a gas-filled particle comprising a stabilized membrane and/or sheath membrane encapsulating one or more gases. In some aspects and embodiments, a gas-filled particle comprising a stabilized membrane encapsulating one or more gases is provided. In other aspects and embodiments, a gas-filled particle comprising a stabilized membrane encapsulating a sheath membrane which further encapsulates one or more gases is provided. In certain embodiments, the stabilized membrane or sheath membrane includes at least two components selected from the following: a lipidic material, a polymer, and a carbohydrate. In certain embodiments, the stabilized membrane includes a lipidic material and a polymer. In certain embodiments, the stabilized membrane includes a lipidic material and a carbohydrate. In certain embodiments, the stabilized membrane includes a polymer and a carbohydrate. In certain embodiments, the stabilized membrane includes a lipidic material, a polymer, and a carbohydrate. In certain embodiments, the particle is prepared in a viscous medium.

In certain embodiments the stabilized membrane is stabilized by the presence of one or more stabilizing agents provided as a component of the membrane. In certain embodiments, the stabilized membrane is stabilized by covalently or non-covalently crosslinked components of the membrane. In certain embodiments, the stabilized membrane is stabilized by covalent crosslinking between components of the stabilized membrane. In certain embodiments, the stabilized membrane is stabilized by non-covalent crosslinking (e.g., by hydrogen and/or ionic bonds) between components of the stabilized membrane. In certain embodiments, the particle membrane includes at least two components selected from the following: a lipidic material, a polymer, and a carbohydrate. In certain embodiments, the stabilized membrane includes a lipidic material and a polymer. In certain embodiments, the stabilized membrane includes a lipidic material and a carbohydrate. In certain embodiments, the stabilized membrane includes a polymer and a carbohydrate. In certain embodiments, the stabilized membrane includes a lipidic material, a polymer, and a carbohydrate.

In certain embodiments the sheath membrane is stabilized by the presence of one or more stabilizing agents provided as a component of the shell. In certain embodiments the sheath membrane is stabilized by covalently crosslinking between components of the shell. In certain embodiments, the sheath membrane is stabilized by non-covalent crosslinking (e.g., by hydrogen and/or ionic bonds) between components of the stabilized membrane. In certain embodiments, the particle membrane includes at least two components selected from the following: a lipidic material, a polymer, and a carbohydrate. In certain embodiments, shell includes a lipidic material and a polymer. In certain embodiments, the shell includes a lipidic material and a carbohydrate. In certain embodiments, the shell includes a polymer and a carbohydrate. In certain embodiments, the shell includes a lipidic material, a polymer, and a carbohydrate. In certain embodiments, the particle is prepared in a viscous medium.

In certain embodiments, the stabilized membrane is stabilized by a crosslinked alginate. In certain embodiments, the particle comprises a stabilized membrane comprising a crosslinked alginate. In certain embodiments, the particle comprises an sheath membrane comprising a crosslinked alginate encapsulating a sheath membrane which further encapsulates one or more gases. In certain embodiments, the sheath membrane of such a particle comprises one or more stabilizing agents, lipidic materials, polymers, proteins, carbohydrates, antioxidants, cryoprotectants, and/or detergents. In certain embodiments, the stabilizing agent is cholesterol. In certain embodiments, the lipidic material is a phospholipid, such as 1,2-distearoyl-sn-glycero-3-phosphocholine (DSPC). In certain embodiments, the particle is prepared in a viscous medium. In certain embodiments, the membrane and/or sheath membrane is stabilized by one or more components stabilized by interactions such as surface charge. The zeta potential (surface charge) can be used to define pairs of components that can be used together in a manner that stabilizes the membrane. For instance, polyallylamine can be used to stabilize a shell containing a negative charge (like a 1,2-dioleoyl-sn-glycero-3-phosphoethanolamine-N-(succinyl) (sodium salt), which is a lipid with a terminal carboxylic acid group. The polyallylamine electrostatically binds to it. This process can be reversed and one can have amine-containing lipids in the shell and stabilize it with a poly-acid polymer. Particles with a negative zeta potential can be stabilized by addition of positively-charged polymers (i.e. Polyallylamine); whereas particles with a positive zeta potential can be stabilized by coating with a negative polymer such as Polyglutamic acid.

In certain embodiments, particle comprises a stabilized membrane comprising one or more stabilized components. In certain embodiments, the particle comprises a sheath membrane comprising one or more stabilized components, further encapsulating a sheath membrane which further encapsulates one or more gases. In certain embodiments, the sheath membrane of such a particle comprises one or more stabilizing agents, lipidic materials, polymers, proteins, carbohydrates, antioxidants, cryoprotectants, and/or detergents. In certain embodiments, the stabilizing agent is cholesterol. In certain embodiments, the lipidic material is a phospholipid, such as 1,2-distearoyl-sn-glycero-3-phosphocholine (DSPC). In certain embodiments, the particle is prepared in a viscous medium.

In certain embodiments, the stabilized membrane and/or sheath membrane is stabilized by one or more components crosslinked by covalent bonds. In certain embodiments, the membrane is a covalently crosslinked polymer, covalently crosslinked carbohydrate, or covalently crosslinked protein.

In certain embodiments, the crosslinked polymer is a crosslinked polyallylamine, a crosslinked polyglutamic acid (PG), and/or a poly(lactic-co-glycolic acid) (PLGA), e.g., modified with one or more "X" or "Y" groups to form a crosslink "A". In certain embodiments, the polyallylamine is formed by covalently crosslinking allylamine. In certain embodiments, the crosslinked protein is a crosslinked albumin. A particle such as a PLGA particle may have some hydrogen bonding, but typically it is stabilized by its hydrophobicity.

In other embodiments the stabilized membrane is composed of polymers that are not crosslinked. The polymers may be stabilized due to electrostatic forces. In other embodiments the polymeric particles may be a combination of electrostatic and crosslinked.

In any of the above aspect, in certain embodiments, the one or more gases is not a fluorinated gas, perfluorocarbon based liquid, or a hemoglobin (e.g., a natural or synthetic hemoglobin). In certain embodiments, the one or more gases is not air (e.g., natural air). In certain embodiments, the one or more gases is not covalently bound to the particle. In certain embodiments, the one or more gases is not dissolved in the stabilized membrane or the sheath membrane. In certain embodiments, the gas is not hydrogen gas ($^1H_2$) or an isotope thereof, e.g., the gas is not deuterium gas ($^2H_2$) or tritium gas ($^3H_2$). In certain embodiments, the gas is a biological gas, e.g., a gas used for therapeutic purposes.

In certain embodiments, the gas encapsulated in the particle is oxygen, nitrogen, carbon dioxide, nitric oxide, helium, an inhalational anesthetic, argon, xenon, hydrogen sulfide or a mixture thereof. In certain embodiments, particle comprises at least about 10%, 20%, 30%, 40%, 50%, 60%, 70%, 80% 90% or 95% gas by volume. In certain embodiments, the shelf-life of the particles is greater than 6 months. In certain embodiments, the shelf-life of the particles is greater than 1 year.

In certain embodiments, the particle is a microparticle. In certain embodiments, the particle has a diameter of 0.05 microns to about 50 microns.

In another aspect, provided is a pharmaceutical composition comprising a particle as described herein and a pharmaceutically acceptable excipient. In yet another aspect, provided is a suspension comprising a particle as described herein provided in aqueous solution for storage. In certain embodiments, the aqueous solution comprises a calcium salt for enhanced stability. In certain embodiments, the particle and/or pharmaceutical composition comprising the particle further includes a therapeutic agent. In certain embodiments, the particle and/or pharmaceutical composition comprising the particle further includes a therapeutic agent co-formulated with the gas to be delivered.

In another aspect, provided is a method of delivering a gas to a subject in need thereof, the method comprising administering to the subject a pharmaceutical composition comprising a particle as described herein and a pharmaceutically acceptable excipient. In certain embodiments, the pharmaceutical composition is administered to the subject by intravenous, intraosseous, or intraarterial injection. In certain embodiments, the pharmaceutical composition is administered to the subject by inhalation or nebulization. In certain embodiments, the pharmaceutical composition is administered topically to the skin, e.g., to a wound or lesion. In certain embodiments, the gas is oxygen. In certain embodiments, oxygen is delivered at an infusion rate of 10 to 400 ml/minute to the subject. In certain embodiments, the subject is or is suspected of experiencing local or systemic hypoxia. In certain embodiments, the subject has or is suspected of having a disease or disorder selected from the group consisting of congenital physical or physiologic disease, transient ischemic attack, stroke, acute trauma, cardiac arrest, exposure to a toxic agent (e.g., such as carbon monoxide), heart disease, hemorrhagic shock, pulmonary disease, acute respiratory distress syndrome, infection (e.g. sepsis), acute decompression sickness, and multi-organ dysfunction syndrome.

In certain embodiments, the particle is useful as a volume expander.

In another aspect, provided are methods of preparing a particle as described herein.

For example, in one aspect, provided is a method of preparing a core/sheath membrane, such as a particle encapsulating a gas, the method comprising:
(i) mixing one or more materials in a medium to form a pre-suspension; and
(ii) dispersing one or more gases into the pre-suspension to form gas-filled particles comprising a stabilized membrane.

In another aspect, provided is a method of preparing a particle encapsulating a gas, the method comprising:
(i) mixing one or more materials in a medium to form a pre-suspension, wherein at least one material comprises a covalent or non-covalent crosslinkable group;
(ii) dispersing one or more gases into the pre-suspension to form gas-filled particles comprising a stabilized membrane; and
(iii) subjecting the gas-filled particle to polymerization or crosslinking conditions in order to provide a covalent or non-covalent crosslinked stabilized membrane.

An example of this method is BSA conjugated to an acrylate group.

In another aspect, provided is a method of preparing a particle encapsulating a gas, the method comprising:
(i) mixing one or more materials in a medium to form a pre-suspension;
(ii) dispersing one or more gases into the pre-suspension to form gas-filled particles comprising a stabilized membrane; and
(iii) contacting the gas-filled particle with a material which comprises a covalent or non-covalent crosslinkable group, wherein the material encapsulates the membrane as a covalent or non-covalent crosslinked sheath membrane upon subjecting the mixture to polymerization or crosslinking conditions.

Polyallylamine coated on 1,2-dioleoyl-sn-glycero-3-phosphoethanolamine-N-(succinyl) (sodium salt) is an example of this method.

Optionally, in another aspect, the inventors contemplate making particles around a small core component to create a hollow structure, wherein the core component is removed to form a hollow dried particle.

For example, in one embodiment, provided is a method of preparing a particle encapsulating a core component, the method comprising mixing one or more materials with a core component to form a pre-suspension comprising particles encapsulating the core component in a stabilized membrane.

In another embodiment, provided is a method of preparing a particle encapsulating a core component, the method comprising: mixing one or more materials with a core component to form a pre-suspension comprising particles encapsulating the core component in a stabilized membrane, wherein at least one material comprises a covalent or non-covalent crosslinkable group; and subjecting the particle to polymerization or crosslinking conditions in order to provide a covalent or non-covalent crosslinked stabilized membrane. In some embodiments the core component is removed. In other embodiments the core component is a volatile medium.

In another aspect, provided is a method of preparing a particle encapsulating a core component, the method comprising: mixing one or more materials with a core component to form a pre-suspension comprising particles encapsulating the core component around a stabilized membrane, wherein at least one material comprises a covalent or non-covalent crosslinkable group; and contacting the particle with a material which comprises a covalent or non-covalent crosslinkable group, wherein the material encapsulates the membrane as a covalent or non-covalent crosslinked sheath membrane upon subjecting the mixture to polymerization or crosslinking conditions. In certain embodiments, the core component is removed from the particle to provide a hollow dried particle.

In another aspect a method for preparing a gas filled particle is provided. The method involves spray drying a polymer with a core component to produce a hollow dry particle and contacting the hollow dry particle with a biological gas. In some embodiments the biological gas is oxygen. In other embodiments the gas is pressurized. In yet other embodiments the spray drying of the polymer is achieved using a 3-fluid nozzle.

The details of one or more embodiments of the invention are set forth in the accompanying Detailed Description, Examples, Claims, and Figures. Other features, objects, and advantages of the invention will be apparent from the description and from the claims.

Definitions

Definitions of specific functional groups and chemical terms are described in more detail below. The chemical elements are identified in accordance with the Periodic Table of the Elements, CAS version, Handbook of Chemistry and Physics, $75^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, $5^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, $3^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of*

*Carbon Compounds* (McGraw-Hill, NY, 1962); and Wilen, S. H. *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., —$CH_3$). In certain embodiments, the alkyl group is a substituted $C_{1-10}$ alkyl.

As used herein, "haloalkyl" is a substituted alkyl group as defined herein wherein one or more of the hydrogen atoms are independently replaced by a halogen, e.g., fluoro, bromo, chloro, or iodo.

As used herein, "perhaloalkyl" is a substituted alkyl group as defined herein wherein all of the hydrogen atoms are independently replaced by a halogen, e.g., fluoro, bromo, chloro, or iodo. In some embodiments, the alkyl moiety has 1 to 8 carbon atoms ("$C_{1-8}$ perhaloalkyl"). In some embodiments, the alkyl moiety has 1 to 6 carbon atoms ("$C_{1-6}$ perhaloalkyl"). In some embodiments, the alkyl moiety has 1 to 4 carbon atoms ("$C_{1-4}$ perhaloalkyl"). In some embodiments, the alkyl moiety has 1 to 3 carbon atoms ("$C_{1-3}$ perhaloalkyl"). In some embodiments, the alkyl moiety has 1 to 2 carbon atoms ("$C_{1-2}$ perhaloalkyl"). In some embodiments, all of the hydrogen atoms are replaced with fluoro. In some embodiments, all of the hydrogen atoms are replaced with chloro. Examples of perhaloalkyl groups include —$CF_3$, —$CF_2CF_3$, —$CF_2CF_2CF_3$, —$CCl_3$, —$CFCl_2$, —$CF_2Cl$, and the like.

As used herein, "heteroalkyl" refers to an alkyl group as defined herein which further includes at least one heteroatom (e.g., 1, 2, 3, or 4 heteroatoms) selected from oxygen, nitrogen, or sulfur within (i.e., inserted between adjacent carbon atoms of) the parent chain. In certain embodiments, a heteroalkyl group refers to a saturated group having from 1 to 10 carbon atoms and 1, 2, 3, or 4 heteroatoms within the parent chain ("hetero$C_{1-10}$ alkyl"). In some embodiments, a heteroalkyl group is a saturated group having 1 to 9 carbon atoms and 1, 2, 3, or 4 heteroatoms within the parent chain ("hetero$C_{1-9}$ alkyl"). In some embodiments, a heteroalkyl group is a saturated group having 1 to 8 carbon atoms and 1, 2, 3, or 4 heteroatoms within the parent chain ("hetero$C_{1-8}$ alkyl"). In some embodiments, a heteroalkyl group is a saturated group having 1 to 7 carbon atoms and 1, 2, 3, or 4 heteroatoms within the parent chain ("hetero$C_{1-7}$ alkyl"). In some embodiments, a heteroalkyl group is a saturated group having 1 to 6 carbon atoms and 1, 2, or 3 heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

As used herein, "alkenyl" refers to a radical of a straight-chain or branched hydrocarbon group having from 2 to 10 carbon atoms and one or more double bonds (e.g., 1, 2, 3, or 4 double bonds) and optionally one or more triple bonds (e.g., 1, 2, 3, or 4 triple bonds). In certain embodiments, the alkynyl group does not contain any triple bonds. In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl.

As used herein, "heteroalkenyl" refers to an alkenyl group as defined herein which further includes at least one heteroatom (e.g., 1, 2, 3, or 4 heteroatoms) selected from oxygen, nitrogen, or sulfur within (i.e., inserted between adjacent carbon atoms of) the parent chain. In certain embodiments, a heteroalkenyl group refers to a group having from 2 to 10 carbon atoms, at least one double bond, and 1, 2, 3, or 4 heteroatoms within the parent chain ("heteroC$_{2-10}$ alkenyl"). In some embodiments, a heteroalkenyl group has 2 to 9 carbon atoms at least one double bond, and 1, 2, 3, or 4 heteroatoms within the parent chain ("heteroC$_{2-9}$ alkenyl"). In some embodiments, a heteroalkenyl group has 2 to 8 carbon atoms, at least one double bond, and 1, 2, 3, or 4 heteroatoms within the parent chain ("heteroC$_{2-8}$ alkenyl"). In some embodiments, a heteroalkenyl group has 2 to 7 carbon atoms, at least one double bond, and 1, 2, 3, or 4 heteroatoms within the parent chain ("heteroC$_{2-7}$ alkenyl"). In some embodiments, a heteroalkenyl group has 2 to 6 carbon atoms, at least one double bond, and 1, 2, or 3 heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and 1 or 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

As used herein, "alkynyl" refers to a radical of a straight-chain or branched hydrocarbon group having from 2 to 10 carbon atoms and one or more triple bonds (e.g., 1, 2, 3, or 4 triple bonds) and optionally one or more double bonds (e.g., 1, 2, 3, or 4 double bonds) ("C$_{2-10}$ alkynyl"). In certain embodiments, the alkynyl group does not contain any double bonds. In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_2$-alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted C$_{2-10}$ alkynyl. In certain embodiments, the alkynyl group is a substituted C$_{2-10}$ alkynyl.

As used herein, "heteroalkynyl" refers to an alkynyl group as defined herein which further includes at least one heteroatom (e.g., 1, 2, 3, or 4 heteroatoms) selected from oxygen, nitrogen, or sulfur within (i.e., inserted between adjacent carbon atoms of) the parent chain. In certain embodiments, a heteroalkynyl group refers to a group having from 2 to 10 carbon atoms, at least one triple bond, and 1, 2, 3, or 4 heteroatoms within the parent chain ("heteroC$_{2-10}$ alkynyl"). In some embodiments, a heteroalkynyl group has 2 to 9 carbon atoms, at least one triple bond, and 1, 2, 3, or 4 heteroatoms within the parent chain ("heteroC$_{2-9}$ alkynyl"). In some embodiments, a heteroalkynyl group has 2 to 8 carbon atoms, at least one triple bond, and 1, 2, 3, or 4 heteroatoms within the parent chain ("heteroC$_{2-8}$ alkynyl"). In some embodiments, a heteroalkynyl group has 2 to 7 carbon atoms, at least one triple bond, and 1, 2, 3, or 4 heteroatoms within the parent chain ("heteroC$_{2-7}$ alkynyl"). In some embodiments, a heteroalkynyl group has 2 to 6 carbon atoms, at least one triple bond, and 1, 2, or 3 heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and 1 or 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

As used herein, "carbocyclyl" refers to a radical of a non-aromatic cyclic hydrocarbon group having from 3 to 10 ring carbon atoms ("C$_{3-10}$ carbocyclyl") and zero heteroatoms in the non-aromatic ring system. In some embodiments, a carbocyclyl group has 3 to 8 ring carbon atoms ("C$_{3-8}$ carbocyclyl"). In some embodiments, a carbocyclyl group has 3 to 6 ring carbon atoms ("C$_{3-6}$ carbocyclyl"). In some embodiments, a carbocyclyl group has 3 to 6 ring carbon atoms ("C$_{3-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_6$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-10}$ cycloalkyl. In certain embodiments, the cycloalkyl group is a substituted $C_{3-10}$ cycloalkyl.

As used herein, "heterocyclyl" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, thiorenyl. Exemplary 4-membered heterocyclyl groups containing 1 heteroatom include, without limitation, azetidinyl, oxetanyl and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo-[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group, as defined herein, substituted by an aryl group, as defined herein, wherein the point of attachment is on the alkyl moiety.

As used herein, "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group, as defined herein, substituted by a heteroaryl group, as defined herein, wherein the point of attachment is on the alkyl moiety.

As used herein, the term "partially unsaturated" refers to a ring moiety that includes at least one double or triple bond. The term "partially unsaturated" is intended to encompass rings having multiple sites of unsaturation, but is not intended to include aromatic groups (e.g., aryl or heteroaryl moieties) as herein defined.

As used herein, the term "saturated" refers to a ring moiety that does not contain a double or triple bond, i.e., the ring contains all single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

As understood from the above, alkyl, alkenyl, alkynyl, heteroalkyl, heteroalkenyl, heteroalkynyl, carbocyclyl, heterocyclyl, aryl, and heteroaryl groups, as defined herein, are, in certain embodiments, optionally substituted. Optionally substituted refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{1-10}$ heteroalkyl, C$_{2-10}$ heteroalkenyl, C$_{2-100}$ heteroalkynyl, C$_{3-14}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{1-10}$ heteroalkyl, C$_{2-10}$ heteroalkenyl, C$_{2-10}$ heteroalkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{1-10}$ heteroalkyl, C$_{2-10}$ heteroalkenyl, C$_{2-10}$ heteroalkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{1-10}$ heteroalkyl, C$_{2-10}$ heteroalkenyl, C$_{2-10}$heteroalkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NRCO$_2$R$^{ee}$, —NR$^{ff}$C(=O)N(R$^{ff}$)$_2$, —C(=NR$^{ff}$)OR$^{ee}$, OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O) (R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{1-6}$ heteroalkyl, C$_{2-6}$ heteroalkenyl, C$_{2-6}$heteroalkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{1-6}$ heteroalkyl, C$_{2-6}$ heteroalkenyl, C$_{2-6}$heteroalkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{1-6}$ heteroalkyl, $C_{2-6}$ heteroalkenyl, $C_{2-6}$heteroalkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{2-16}$ alkyl, —SO$_2$OC$_1$ alkyl, —OSO$_2$C$_{1-6}$ alkyl, —SOC$_{1-6}$alkyl, —Si(C$_{1-6}$ alkyl)$_3$, —OSi(C$_{1-6}$ alkyl)$_3$ —C(=S)N(C$_{1-6}$ alkyl)$_2$, C(=S)NH(C$_{1-6}$ alkyl), C(=S)NH$_2$, —C(=O)S(C$_{1-5}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$alkyl, C$_{1-6}$ perhaloalkyl, C$_{2-6}$ alkenyl, C$_{2-6}$ alkynyl, C$_{1-6}$heteroalkyl, C$_{2-6}$ heteroalkenyl, C$_{2-6}$heteroalkynyl, C$_{3-10}$ carbocyclyl, C$_{6-10}$ aryl, 3-10 membered heterocyclyl, 5-10 membered heteroaryl; or two geminal $R^{gg}$ substituents can be joined to form =O or =S; wherein X$^-$ is a counterion.

As used herein, the term "halo" or "halogen" refers to fluorine (fluoro, —F), chlorine (chloro, —Cl), bromine (bromo, —Br), or iodine (iodo, —I).

As used herein, a "counterion" is a negatively charged group associated with a positively charged quarternary amine in order to maintain electronic neutrality. Exemplary counterions include halide ions (e.g., F$^-$, Cl$^-$, Br$^-$, I$^-$), NO$_3^-$, ClO$_4^-$, OH$^-$, H$_2$PO$_4^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{1-10}$ heteroalkyl, C$_{2-10}$ heteroalkenyl, C$_{2-10}$ heteroalkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{1-10}$ heteroalkyl, C$_{2-10}$ heteroalkenyl, C$_{2-10}$ heteroalkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10, 10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido) ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), J3-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

These and other exemplary substituents are described in more detail in the Detailed Description, Examples, and claims. The invention is not intended to be limited in any manner by the above exemplary listing of substituents.

As used herein, the term "salt" refers to any and all salts. The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

"Microbubbles" and "bubbles" are used interchangeably herein to refer to a gas core surrounded by a lipid membrane (non-crosslinked), which can be either a monolayer or a bilayer and wherein the lipid membrane can contain one or more lipids and one or more stabilizing agents.

"Particles", "nanoparticles" and "microparticles" are used interchangeably herein to refer to a membrane capable of housing a gas within the hollow core.

A "stabilized membrane" as used herein is a membrane surrounding a hollow core capable of being filled with a gas and which is stabilized with respect to a microbubble membrane. The stabilized membrane comprises a polymer, a monomer, a polymer-lipid mixture, a monomer-polymer mixture, a monomer-lipid mixture or a cross-linked lipid. The stabilized membrane is not composed of a non-crosslinked lipid and/or non-crosslinked lipid/stabilizer in the absence of a polymer.

A "stabilized particle", as used herein, refers to a particle comprising a stabilized membrane. The stabilized particle may be composed solely of a stabilized membrane and a gas core. Alternatively the stabilized particle may include a stabilized membrane surrounding an optional sheath wherein the sheath is positioned between the gas core and the stabilized membrane and/or other components. The sheath may be composed of a lipid membrane. In some embodiments the sheath is a lipid membrane such as a microbubble lipid membrane described in US Publication No. 2009/0191244 or PCT Publication No. WO2012/065060. The stabilized membrane and sheath may be each independently covalently or non-covalently crosslinked and/or stabilized, for example, by a stabilizing agent or by the interactions between the one or more components of the membrane or based on the chemical properties of the one or more components of the membrane (for instance the hydrophobicity of a polymer such as PLGA). A "stabilized particle" as used herein does not encompass a bubble or microbubble having a non-crosslinked lipid membrane, unless the bubble or microbubble includes a further stabilized membrane composed of a material other than non-crosslinked lipids. For instance, a stabilized particle may include an inner non-crosslinked lipid membrane and an outer stabilized membrane of crosslinked lipids or of polymers.

BRIEF DESCRIPTION OF THE DRAWINGS

FIG. 13A), a scanning electron micrograph of a hollow microparticle with a thin (~300 nm) PLGA shell (FIG. 13B) and a microparticle size distribution (optical light scattering) after filtration through a 20 μm nylon mesh filter (FIG. 13C).

FIGS. 14A-14B show shows Viscoelasticity (represented by storage and loss moduli) of LOMs and a 55 volume % PLGA slurry measured every minute over a 60 minute observation period. The fluid phase enters the particle core, causing viscosity to increase over time (FIG. 14A). LOMs demonstrate no change in viscoelasticty over the 60 minute observation period. Utilizing lower concentrations of PVA or alternative polymers will prevent this phenomenon. Some particles contain PVA webbing in the core, leading to increased fluid filling (FIG. 14B).

(FIG. 18A) The percent yield of honeycomb particles was analyzed using the effect screening platform within the least squares personality. The fitted model had a adjusted root mean squared value (R2) of 0.78. ANOVA analysis revealed a p value <0.001, suggesting the presence of significant effects the model. Significant model terms (p<0.05) are shown in order of decreasing significance within the sorted parameters effects table. (FIG. 18B) Plot of the significant interaction terms.

(FIG. 19A) The diameter of honeycomb particles was analyzed using the effect screening platform within the least squares personality. The fitted model had a adjusted root mean squared value (R2) of 0.63. ANOVA analysis revealed a p value <0.001, suggesting the presence of significant effects the model. Significant model terms (p<0.05) are shown in order of decreasing significance within the sorted parameters effects table. (FIG. 19B) Plot of the models significant interaction terms.

FIGS. 21A-21C. The model was evaluated by using the prediction profiler to predict the percent yield and particle size when the secondary emulsion was changed to 15,000 rpm. (FIG. 21A) Optical photomicrographs of the microparticles reveal a highly porous structure. (FIG. 21B) Scanning electron micrographs reveal the presence of surface defects and the heterogeneous internal morphologies of honeycomb microparticles fabricated at 15,000 rpm. (FIG. 21C) Predicted and actual percent yields and particle diameters for particles manufactured at 15,000 rpm.

DETAILED DESCRIPTION OF CERTAIN EMBODIMENTS OF THE INVENTION

Figure 1:
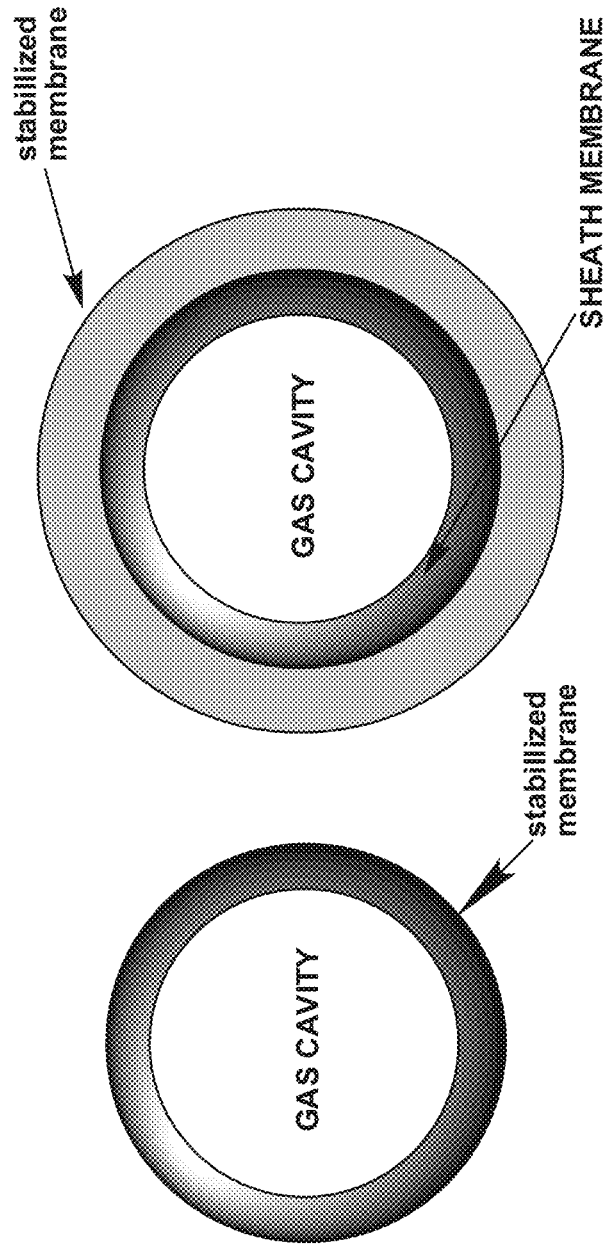
FIG. 1 depicts two concepts for forming stabilized particles encapsulating a gas. One concept envisions stabilizing the particle within the stabilized membrane. The other concept envisions stabilizing the particle with a stabilized membrane surrounding the sheath membrane.

Previous work has established the possibility of encapsulating a gas, such as oxygen, in a lipid membrane in the form of a microbubble for therapeutic delivery of the gas to a subject. The fluidity of the lipid membrane of the microbubble resulted in rapid delivery of the gases when administered to a subject. For example, previous work has established that administering to asphyxial subjects oxygen-filled microparticles via intravenous injection successfully restores oxygen supply in the subject, preserves spontaneous circulation during asphyxia, and reduces occurrence of cardiac arrest. See, e.g., US Publication No. 2009/0191244 and PCT Application Publication No. WO 2012/065060, incorporated herein by reference. However, current microbubble formulations may break upon experiencing high shear forces (e.g. by rapid injection through an intravenous or intraosseous catheter) due to the fact the lipids self-assemble at the gas-liquid interface; these may limit its utility in emergency situations. Furthermore, the instability of lipid-based microparticles when stored prior to use may be attributed to three main mechanisms: lipid oxidiation, lipid hydrolysis, and/or aggregation. The microbubbles also may be less stable at various temperatures. Lipid oxidation and hydrolysis can occur via a variety of mechanisms and ultimately lead to the degradation of the lipid backbone, which destabilizes the lipid monolayer and promotes dissolution of the encapsulated oxygen gas, causing these molecules to have a short shelf life.

It was discovered, quite surprisingly, according to the invention, that stabilized particles encapsulating one or more gases in a stabilized membrane such as a polymeric or crosslinked lipid membrane or polymeric-lipid membrane are useful for delivering gas to a subject for therapeutic and diagnostic purposes. The particles of the invention may be stabilized, for example, by covalently or non-covalently (e.g., ionically) crosslinking one or more components of the stabilized membrane that encapsulates the gas to form a crosslinked stabilized membrane, by encapsulating a sheath membrane in a stabilized membrane, and/or by the use of one or more stabilizing agents as a component of the sheath membrane to stabilize the membrane. It was further discovered, in some embodiments, that preparing these types of particles in a viscous medium, such as corn syrup, simplifies the preparative process, and produces particles with less defects, with higher shelf life, and improved size distribution compared to particles not prepared in a viscous medium. Additionally, particles of the invention may be polymeric particles produced by methods such as spray drying. Such particles have been found to successfully encapsulate gasses and have excellent stability properties.

Thus, in one aspect, provided is a gas-filled particle comprising a stabilized membrane encapsulating one or more gases. This stabilized membrane refers to a membrane formed around a core of gas that may be a single or double layer membrane or a crosslinked membrane. In other aspects and embodiments, a gas-filled particle comprising a stabilized membrane encapsulating a sheath membrane which further encapsulates one or more gases is provided. In certain embodiments, the particle membrane includes at least two components selected from the following: a lipidic material, a polymer, and a carbohydrate. In certain embodiments, the sheath membrane or stabilized membrane includes a lipidic material and a polymer. In certain embodiments, the sheath membrane or stabilized membrane includes a lipidic material and a carbohydrate. In certain embodiments, the sheath membrane or stabilized membrane includes a polymer and a carbohydrate. In certain embodiments, the sheath membrane or stabilized membrane includes a lipidic material, a polymer, and a carbohydrate. In certain embodiments, the particle is prepared in a viscous medium.

In certain embodiments, the membrane is comprised of one or more biocompatible materials, e.g., biocompatible polymers, carbohydrates, or proteins, e.g., selected from the group consisting of poly(lactic-co-glycolic acid (PLGA), polyglutamic acid (PG), dextran, hyaluronic acid, poly(citrate), poly(glycerol sebacate), elastin, chitosan, poly(carbonate), poly(hydroxy acids), polyanhydrides, polyorthoesters, polyamides, polycarbonates, polyalkylenes, polyalkylene glycols, polyalkylene oxides, polyalkylene terephthalates, polyvinyl alcohols, polyvinyl ethers, polyvinyl esters, polyvinyl halides, polyvinylpyrrolidone, polysiloxanes, poly(vinyl alcohols), poly(vinyl acetate), polystyrene, polyurethanes and co-polymers thereof, synthetic celluloses, polyacrylic acids, poly(butyric acid), poly(valeric acid), and poly(lactide-co-caprolactone), ethylene vinyl acetate, copolymers and blends thereof. In certain embodiments, the biocompatible material is selected from the group consisting of poly(lactic-co-glycolic acid (PLGA), polyglutamic acid (PG) dextran, hyaluronic acid, poly(citrate), poly(glycerol sebacate), and poly(carbonate).

In particular smaller carbohydrates are useful in spray drying techniques. In some instances it is desirable to modify the small carbohydrates such that they are water insoluble. For instance carbohydrates may be modified by acetylation to produce water insoluble modified carbohydrates. Such modifications are well known in the art. Larger carbohydrates are useful in multiple methods of making the particles including spray drying and emulsions, and may or may not be modified for optimum effect.

In any of the embodiments, wherein the membrane is stabilized with one or more stabilizing agents, the gas-filled particle is not necessarily, but may be optionally, crosslinked. For example, in certain embodiments, the stabilized membrane is further crosslinked. In certain embodiments, the particle further comprises a crosslinked sheath membrane encapsulated within the stabilized membrane.

In any of the above aspect, in certain embodiments, the one or more gases is not a fluorinated gas, perfluorocarbon based liquid, or a hemoglobin (e.g., a natural or synthetic hemoglobin). In certain embodiments, the one or more gases is not air (e.g., natural air). In certain embodiments, the one or more gases is not covalently bound to the particle. In certain embodiments, the one or more gases is not dissolved in the stabilized membrane or the sheath membrane. In certain embodiments, the gas is not hydrogen gas ($^1H_2$) or an isotope thereof, e.g., the gas is not deuterium gas ($^2H_2$) or tritium gas ($^3H_2$).

Non-Covalent Crosslinking

As generally understood from the above disclosure, in certain embodiments, the stabilized membrane or the sheath membrane is stabilized by non-covalent bonding, e.g., ionic bonding, i.e., formed by ionically crosslinking one or more materials, and/or hydrogen bonding, i.e., forming a hydrogen bonded network between one or more materials. Crosslinking ions that are used to ionically crosslink polymers may be anions or cations, depending on whether the material is anionically or cationically crosslinkable. Appropriate crosslinking ions include but are not limited to polyvalent cations selected from the group consisting of calcium, magnesium, barium, strontium, boron, beryllium, aluminum, iron, copper, cobalt, lead and silver cations ions. Crosslinking anions may be selected from, but are not limited to, the group consisting of phosphate, citrate, borate, succinate, maleate, adipate and oxalate anions. More broadly, crosslinking anions are commonly derived from polybasic organic or inorganic acids.

Ionic crosslinking may be carried out by methods known in the art, for example, by contacting the material with an aqueous solution containing dissolved ions. For some materials, the solution in which the crosslinking is performed may contain a high concentration of calcium to enhance stability. After formation of the particle, the emulsion may be "activated" or uncrosslinked by mixing with citrate (or other calcium-binding agent) just prior to use.

Examples of ionically crosslinkable materials are disclosed, for example, in U.S. Pat. Nos. 6,096,018 and 6,060,534. Ionically crosslinkable polymers can be either cationic or anionic in nature and include carboxylic, sulfate, and amine functionalized polymers such as polyacrylic acid, polymethacrylic acid, polyhydroxy ethyl methacrylate, polyvinyl alcohol, polyacrylamide, poly(N-vinyl pyrrolidone), polyethylene oxide, hydrolyzed polyacrylonitrile, polyethylene amine, polysaccharides, alginates (e.g., alginic acid (alginate), Propylene glycol alginate (PGA), gelatin, pectinic acid, carboxy methyl cellulose, hyaluronic acid, heparin, heparin sulfate, chitosans (e.g., chitosan, cationic chitosan (conjugated with amines), carboxymethyl chitosan, chitin, carboxymethyl starch, dextran, carboxymethyl dextran, chondroitin sulfate, cationic guar, hyaluronic acid, cationic starch, pectinic acid, pullulan, gellan, xanthan, and collagen as well as mixtures, derivatives (such as salts and esters) and copolymers thereof. Cationic and anionic polymers include for instance polyallylamine and polyglutamic acid, etc. Many of these materials are may be crosslinked with each other, with other covalent crosslinking agents, or with other ionic crosslinking agents. For example, in certain embodiments, the membrane and/or sheath membrane comprises a crosslinked alginate, e.g., crosslinked with alginate and/or other material. In certain embodiments, the membrane and/or sheath membrane comprises a crosslinked alginate and chitosan mixture.

In certain embodiments, the material that is non-covalently crosslinked forms a hydrogel.

Covalent Crosslinking

As is also generally understood from the above disclosure, in certain embodiments, the stabilized membrane or the sheath membrane is stabilized by covalent bonds, i.e., formed by covalently crosslinking complimentary functionalized materials using chemical coupling or free radical methods. In certain embodiments, these methods comprise a set of reactions typically referred to as "Click chemistry."

Click chemistry is a chemical philosophy introduced by Sharpless in 2001 and describes chemistry tailored to generate substances quickly and reliably by joining small units together. See, e.g., Kolb, Finn and Sharpless *Angewandte Chemie International Edition* (2001) 40: 2004-2021; Evans, *Australian Journal of Chemistry* (2007) 60: 384-395). Exemplary chemical coupling reactions (some which may be classified as "Click chemistry") include, but are not limited to, formation of esters, thioesters, amides (e.g., such as peptide coupling) from activated acids or acyl halides; nucleophilic displacement reactions (e.g., such as nucleophilic displacement of a halide or ring opening of strained ring systems); azide-alkyne Huisgon cycloaddition; thiol-yne addition; imine formation; and Michael additions (e.g., maleimide addition).

In general, for the purposes of covalent crosslinking, at least two materials must be present (referred to as $R^{M1}$ and $R^{M2}$), one material modified with at least one "Y" substituent, and the other material modified with at least one "X" substituent, wherein the "X" and "Y" substituents are complimentary and reactive with each other to form a group "A". For example, if "Y" is a nucleophilic group, then the group "X" must be a electrophilic group, and if "X" is a nucleophilic group, then the group "Y" must be a electrophilic group. If the materials are monofunctionalized, then one covalent bond forms between the two materials. If the materials are di-functionalized or poly-functionalized, then more than one covalent bond forms, and crosslinking between the two materials results. See, e.g., Scheme 1.

Scheme 1.

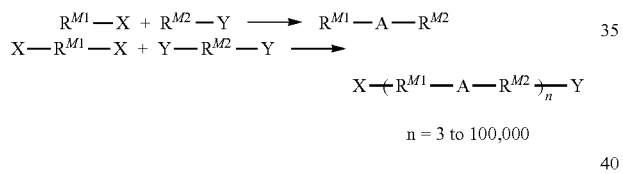

n = 3 to 100,000

Exemplary X and Y substituents include, but are not limited to, —SH, —OH, —NH$_2$, —NH—NH$_2$, —N$_3$, halogen, —C(=O)R$^{Z1}$,

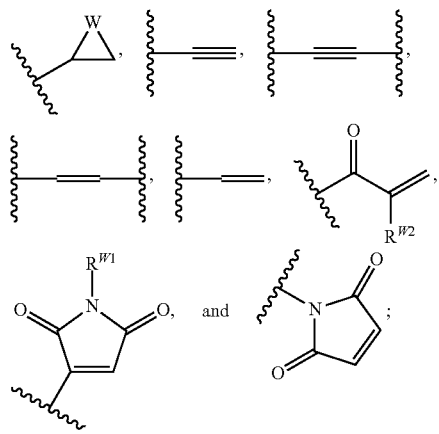

wherein $R^{Z1}$ is hydrogen, halogen, or —OR$^{Z2}$, wherein $R^{Z2}$ is hydrogen, substituted or unsubstituted alkyl, or an oxygen protecting group; and W is —O—, —S—, or —NR$^{W1}$—, wherein R$^{W1}$ is hydrogen, substituted or unsubstituted alkyl, or a nitrogen protecting group; and R$^{W2}$ is hydrogen or substituted or unsubstituted alkyl; and wherein X and Y are paired compliments and react with each other to form a group "A" of the formula:

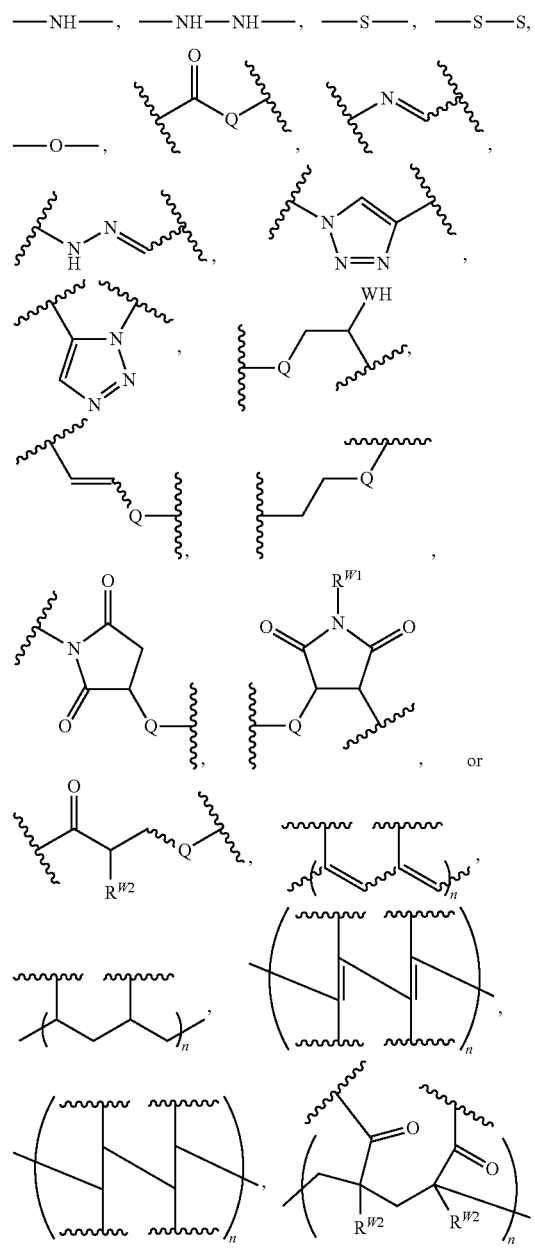

wherein W is —O—, —S—, or —NR$^{W1}$—, R$^{W1}$ is hydrogen, substituted or unsubstituted alkyl, or an amino protecting group; R$^{W2}$ is hydrogen or substituted or unsubstituted alkyl; Q is —NH—, —NH—NH—, —S—, —O—, and n is 3 to 100,000, inclusive; e.g., 3 to 90,000, 3 to 80,000, 3 to 70,000, 3 to 60,000, 3 to 50,000, 3 to 40,000, 3 to 30,000, 3 to 20,000, 3 to 10,000, 3 to 9,000, 3 to 8,000, 3 to 6,000, 3 to 5,000, 3 to 4,000, 3 to 2,000, 3 to 1,000, 3 to 900, 3 to 800, 3 to 700, 3 to 600, 3 to 500, 3 to 400, 3 to 300, 3 to 200, 3 to 100, or 3 to 50, inclusive.

In certain embodiments, the material that is covalently crosslinked forms a hydrogel.

Nucleophilic Addition to Esters or Acyl Halides

For example, in certain embodiments, one material modified with —C(=O)R$^{Z1}$ wherein R$^{Z1}$ is halogen (—Br, —I, or —Cl) or —OR$^{Z2}$ is covalently crosslinked with another material modified with —SH, —OH, —NH$_2$, —NH—NH$_2$ to provide a crosslinked material wherein the crosslink A is an amide (—C(=O)NHNH—, —C(=O)NH—), ester (—C(=O)O—), or thioester (—C(=O)S—) group.

Nucleophilic Displacement of Halogen

In certain embodiments, one material modified with a primary halogen (—Br, —I, or —Cl) is covalently crosslinked with another material modified with —SH, —OH, —NH$_2$, —NH—NH$_2$ by nucleophilic displacement of the halide to provide a crosslinked material wherein the crosslink A is an —S—, —O—, —NH—, or —NH—NH— group.

Nucleophilic Addition to Strained Ring Systems

In certain embodiments, one material modified with a

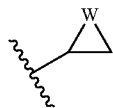

group is covalently crosslinked with another material modified with —SH, —OH, —NH$_2$, —NH—NH$_2$ by nucleophilic addition to strained ring systems to provide a crosslinked material wherein the crosslink A is

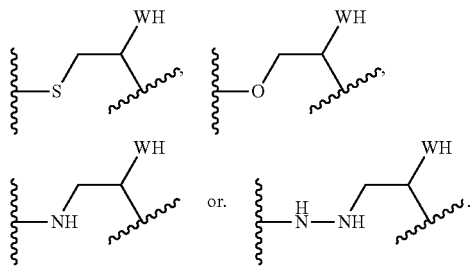

Azide-Alkyne Huisgon Cycloaddition

In certain embodiments, one material modified with a terminal alkyne

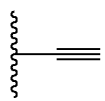

is covalently crosslinked with another material modified with —N$_3$ by azide-alkyne Huisgon cycloaddition to provide a crosslinked material wherein the crosslink A is

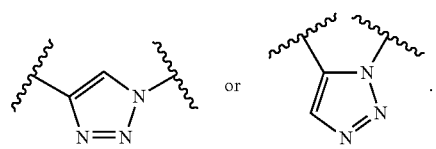 [SMILES: *c1cn(*)nn1 ; *c1cnnn1*]

These include, for instance, cyclooctynes.

Thiol-yne Addition

In certain embodiments, one material modified with a terminal alkyne

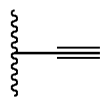 [SMILES: *C#C]

is covalently crosslinked with another material modified with —SH by thiol-yne addition to provide a crosslinked material wherein the crosslink A is

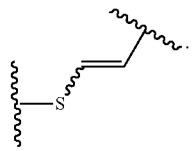

Disulfide Formation

In certain embodiments, two material modified with thiol moieties —SH are covalently crosslinked under oxidative conditions to provide a crosslinked material wherein the crosslink A is a disulfide bond —S—S—.

Imine Formation

In certain embodiments, one material modified with an aldehyde —CHO is covalently crosslinked with another material modified with —NH$_2$ or —NH—NH$_2$ by imine formation to provide a crosslinked material wherein the crosslink A is

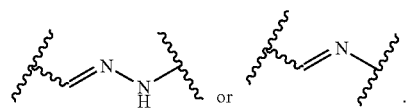

Michael Addition

In certain embodiments, one material modified with

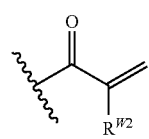

is covalently crosslinked with another material modified with —SH, —OH, —NH$_2$, —NH—NH$_2$ by Michael addition to provide a crosslinked material wherein the crosslink A is

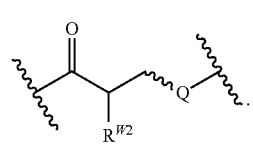

Maleimide Addition

In certain embodiments, one material modified with

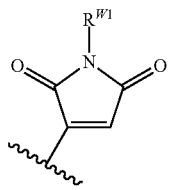

is covalently crosslinked with another material modified with —SH, —OH, —NH$_2$, —NH—NH$_2$ by maleimide addition to provide a crosslinked material wherein the crosslink A is

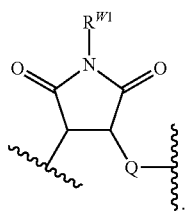

In certain embodiments, one material modified with

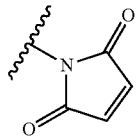

is covalently crosslinked with another material modified with —SH, —OH, —NH$_2$, —NH—NH$_2$ by maleimide addition to provide a crosslinked material wherein the crosslink A is

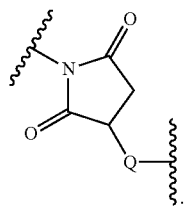

Polymerization

In certain embodiments, one material modified with an acrylate group:

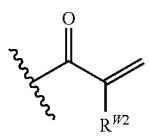

is covalently crosslinked with the same material or a different material modified with an acrylate group by polymerization (head to tail addition, e.g., by free radical polymerization, or cationic polymerization) to provide a crosslinked material wherein the resulting polymerized unit formed comprises:

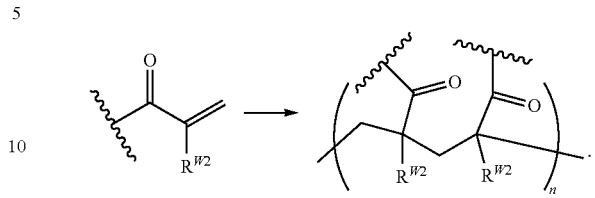

In certain embodiments, one material modified with an alkenyl group:

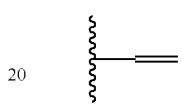

is covalently crosslinked with the same material or a different material modified with an amino group by polymerization (e.g., by cationic polymerization) to provide a crosslinked material wherein the resulting polymerized unit formed comprises:

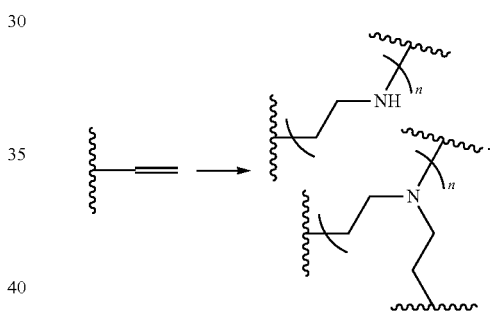

Other materials may be similarly polymerized. For example, materials modified with internal or terminal alkenyl or alkenyl groups:

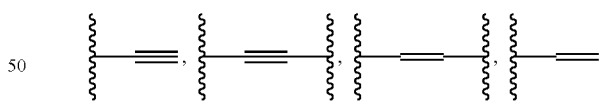

may be polymerized, e.g., by sonication, free radical polymerization, or cationic polymerization (e.g., upon exposure to an acid, H$^+$), to form various crosslinked materials, e.g., wherein the resulting polymerized unit formed is:

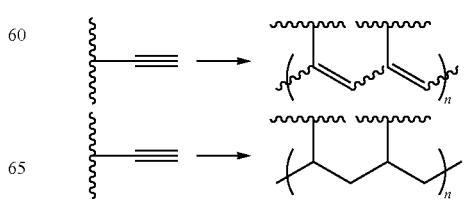

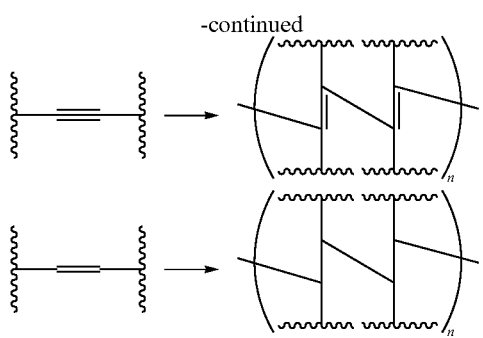

Free radical polymerization may be initiated by a variety of methods, e.g., such as by UV light initiation, chemical methods (e.g., free radical polymerization, cationic polymerization), or by sonication. Free radical polymerization may be initiated by a variety of methods, e.g., for example, by treatment with UV light or a chemical initiator such as AIBN. Cationic polymerization may be initiated by a variety of methods, e.g., for example, by treatment with an electrophile such as an acid ($H^+$ ion).

Lipidic Materials, Optionally Useful in Covalent Crosslinking

In any of the above and below embodiments, a material as a component of the stabilized membrane or sheath membrane may comprise a lipid tail "$R^L$" which, if optionally functionalized with one or more internal or terminal alkynyl or alkenyl groups, may be crosslinked. Such a material comprising a lipid tail is also referred to herein as a "lipidic material", or when crosslinked, a "crosslinked lipidic material." In certain embodiments, the membrane and/or sheath membrane is a crosslinked lipidic material (e.g., comprising a covalently crosslinked lipid tail) as described herein. As used herein, a lipid tail is understood to refer to a substituted or unsubstituted $C_{7-30}$alkyl, substituted or unsubstituted $C_{7-30}$alkenyl, or substituted or unsubstituted $C_{7-30}$alkenyl group. Lipidic materials comprise a group of molecules that include, but are not limited to, fatty acids/esters/amides, triacyl glycerol, terpenes, waxes, sphingolipids, and phospholipids (e.g., phosphocholines, phosphoglycerols, phosphatidic acids, phosphoethanolamines, and phosphoserines), wherein the lipidic material comprises a lipid tail $R^L$ attached thereto, as described herein. See also Tables 1 and 2 of the Examples, and US 2009/0191244, U.S. Pat. Nos. 7,105,151, and 6,315,981.

Lipid tails may be saturated or unsaturated, depending on whether or not the lipid tail comprises double or triple bonds. The lipid tail may also comprise different lengths, often categorized as medium (i.e., with tails between 7-12 carbons, e.g., $C_{7-12}$ alkyl, $C_{7-12}$ alkenyl, $C_{7-12}$ alkynyl), long (i.e., with tails greater than 12 carbons and up to 22 carbons, e.g., $C_{13-22}$ alkyl, $C_{13-22}$ alkenyl, $C_{13-22}$ alkynyl), or very long (i.e., with tails greater than 22 carbons, e.g., $C_{23-30}$ alkyl, $C_{23-30}$ alkenyl, $C_{23-30}$ alkynyl). The lipidic material may comprise one or more different $R^L$ lipid tails attached thereto, or may comprise one or more of the same $R^L$ lipid tails. In certain embodiments, the lipidic material comprises an $R^L$ alkyl tail and an $R^L$ alkenyl tail. In certain embodiments, the lipidic material comprises an $R^L$ alkyl tail and an $R^L$ alkynyl tail. In certain embodiments, the lipidic material comprises two $R^L$ alkenyl tails. In certain embodiments, the lipid comprises two $R^L$ alkynyl tails.

In certain embodiments, the lipid tail $R^L$ is a substituted or unsubstituted $C_{7-30}$alkyl group, e.g., substituted or unsubstituted $C_{10-30}$alkyl, substituted or unsubstituted $C_{20-30}$alkyl, substituted or unsubstituted $C_{10-20}$alkyl, substituted or unsubstituted $C_{10-15}$alkyl, substituted or unsubstituted $C_{15-20}$alkyl, substituted or unsubstituted $C_{15-25}$alkyl, substituted or unsubstituted $C_7$alkyl, $C_8$alkyl, $C_9$alkyl, $C_{10}$alkyl, $C_{11}$alkyl, $C_{12}$alkyl, $C_{13}$alkyl, $C_{14}$alkyl, $C_{15}$alkyl, $C_{16}$alkyl, $C_{17}$alkyl, $C_{18}$alkyl, $C_{19}$alkyl, $C_{20}$alkyl, $C_{21}$alkyl, $C_{22}$alkyl, $C_{23}$alkyl, $C_{24}$alkyl, $C_{25}$alkyl, $C_{26}$alkyl, $C_{27}$alkyl, $C_{28}$alkyl, $C_{29}$alkyl, or $C_{30}$alkyl.

In certain embodiments, the lipid tail $R^L$ is a substituted or unsubstituted $C_{7-30}$alkenyl group, e.g., substituted or unsubstituted $C_{10-30}$alkenyl, substituted or unsubstituted $C_{20-30}$alkenyl, substituted or unsubstituted $C_{10-20}$alkenyl, substituted or unsubstituted $C_{10-15}$alkenyl, substituted or unsubstituted $C_{15-20}$alkenyl, substituted or unsubstituted $C_{15-25}$alkenyl, substituted or unsubstituted $C_7$alkenyl, $C_8$alkenyl, $C_9$alkenyl, $C_{10}$alkenyl, $C_{11}$alkenyl, $C_{12}$alkenyl, $C_{13}$alkenyl, $C_{14}$alkenyl, $C_{15}$alkenyl, $C_{16}$alkenyl, $C_{17}$alkenyl, $C_{18}$alkenyl, $C_{19}$alkenyl, $C_{20}$alkenyl, $C_{21}$alkenyl, $C_{22}$alkenyl, $C_{23}$alkenyl, $C_{24}$alkenyl, $C_{25}$alkenyl, $C_{26}$alkenyl, $C_{27}$alkenyl, $C_{28}$alkenyl, $C_{29}$alkenyl, or $C_{30}$alkenyl.

In certain embodiments, the lipid tail $R^L$ is a substituted or unsubstituted $C_{7-30}$alkynyl group, e.g., substituted or unsubstituted $C_{10-30}$alkynyl, substituted or unsubstituted $C_{20-30}$alkynyl, substituted or unsubstituted $C_{10-20}$alkynyl, substituted or unsubstituted $C_{10-15}$alkynyl, substituted or unsubstituted $C_{15-20}$alkynyl, substituted or unsubstituted $C_{15-25}$alkynyl, substituted or unsubstituted $C_7$alkynyl, $C_8$alkynyl, $C_9$alkynyl, $C_{10}$alkynyl, $C_{11}$alkynyl, $C_{12}$alkynyl, $C_{13}$alkynyl, $C_{14}$alkynyl, $C_{15}$alkynyl, $C_{16}$alkynyl, $C_{17}$alkynyl, $C_{18}$alkynyl, $C_{19}$alkynyl, $C_{20}$alkynyl, $C_{21}$alkynyl, $C_{22}$alkynyl, $C_{23}$alkynyl, $C_{24}$alkynyl, $C_{25}$alkynyl, $C_{26}$alkynyl, $C_{27}$alkynyl, $C_{28}$alkynyl, $C_{29}$alkynyl, or $C_{30}$alkynyl.

Exemplary unsaturated lipid tails include, but are not limited to:
Myristoleic —$(CH_2)_7CH=CH(CH_2)_3CH_3$,
Palmitoliec —$(CH_2)_7CH=CH(CH_2)_5CH_3$,
Sapienic —$(CH_2)_4CH=CH(CH_2)_8CH_3$,
Oleic —$(CH_2)_7CH=CH(CH_2)_7CH_3$,
Linoleic —$(CH_2)_7CH=CHCH_2CH=CH(CH_2)_4CH_3$,
α-Linolenic —$(CH_2)_7CH=CHCH_2CH=CHCH_2CH=CHCH_2CH_3$,
Arachinodonic —$(CH_2)_3CH=CHCH_2CH=CHCH_2CH=CHCH_2CH=CH(CH_2)_4CH_3$,
Eicosapentaenoic —$(CH_2)_3CH=CHCH_2CH=CHCH_2CH=CHCH_2CH=CHCH_2CH_3$,
Erucic —$(CH_2)_{11}CH=CH(CH_2)_7CH_3$, and
Docosahexaenoic —$(CH_2)_2CH=CHCH_2CH=CHCH_2CH=CHCH_2CH=CHCH_2CH=CH—CH_2CH_3$.

Exemplary saturated lipid tails include, but are not limited to:
Lauric —$(CH_2)_{10}CH_3$,
Myristic —$(CH_2)_{12}CH_3$,
Palmitic —$(CH_2)_{14}CH_3$,
Stearic —$(CH_2)_{16}CH_3$,
Arachidic —$(CH_2)_{18}CH_3$,
Behenic —$(CH_2)_{20}CH_3$,
Lignoceric —$(CH_2)_{22}CH_3$, and
Cerotic —$(CH_2)_{24}CH_3$.

Exemplary fatty acids are of the formula $HOC(=O)R^L$, wherein $R^L$ is as defined herein.

Exemplary fatty esters are of the formula $R^EOC(=O)R^L$ or $R^LOC(=O)R^E$ wherein $R^L$ is as defined herein, and $R^E$ is $C_{1-6}$ alkyl, e.g., which include, for example, methyl, ethyl, and isopropyl esters.

Exemplary fatty amides are of the formula $R^E$NHC(=O)$R^L$ or $R^L$NHC(=O)$R^E$ wherein $R^L$ is as defined herein, and $R^E$ is $C_{1-6}$ alkyl, e.g., which include, for example, methyl, ethyl, and isopropyl amides.

Exemplary phospholipids contemplated include, but are not limited to, various phospholipids of the general formula:

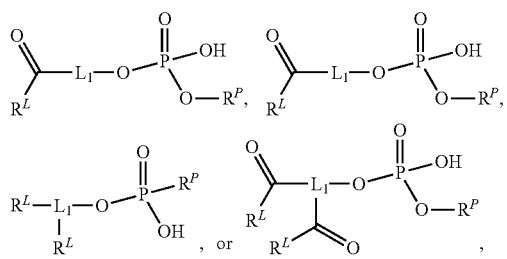

wherein $L^1$ is substituted or unsubstituted alkylene or heteroalkylene, $R^P$ is hydrogen, substituted or unsubstituted alkyl or substituted or unsubstituted heteroalkyl, and $R^L$ is as defined herein.

Specific phospholipids include, but are not limited to, disteroylphosphatidylcholine (DSPC), dimyristoylphosphatidylcholine (DMPC), Dipalmitoylphosphatidylcholine (DPPC), and dioleoyl-sn-glycero-3-phosphocholine (DOPC), 1,2-Dilauroyl-sn-Glycero-3-Phosphocholine (dilauroylphosphatidylcholine, DLPC), 1,2-Dimyristoyl-sn-Glycero-3-Phosphocholine (dimyristoylphosphatidylcholine, DMPC), 1,2-Dipentadecanoyl-sn-Glycero-3-Phosphocholine (dipentadecanoylphosphatidylcholine, DPDPC), 1,2-dipalmitoyl-sn-Glycero-3-Phosphocholine (dipalmitoylphosphatidylcholine, DPPC), 1-Myristoyl-2-Palmitoyl-sn-Glycero-3-Phosphocholine (1-myristoyl-2-palmitoylphosphatidylcholine, MPPC), 1,2-Dimyristoyl-sn-Glycero-3-[Phospho-rac-(1-glycerol)](DMPG), and 1,2-Dimyristoyl-3-Trimethylammonium-propane. Other phospholipids contemplated for use as a component of the particle are provided in Tables 1 and 2 of the Examples.

Stabilizing Agents

As generally defined above, one aspect of the present disclosure is a particle comprising a stabilized membrane encapsulating one or more gases, wherein the membrane or optional sheath membrane includes one or more additional components such as a stabilizing agent, e.g., in addition to stabilization by covalently bound and/or non-covalently bound components of the membrane. For example, stabilization of the membrane may further include non-covalent and/or covalent stabilization, and in that case, the addition of the stabilizing agent further stabilizes the membrane.

As used herein, a "stabilizing agent" refers to a compound capable of preventing particle aggregation and/or decomposition of the particle, and which aids in membrane formation at the gas/liquid interface. In certain embodiments, the stabilizing agent contains a hydrophobic component, which orients itself towards the gas filled core, and a hydrophilic component, which interacts with the aqueous phase and minimizes the energy of the particle, thereby enabling its stability.

In certain embodiments, the stabilizing agent is a hydrophilic material, e.g., a hydrophilic polymer, lipidic material, or carbohydrate, attached to a hydrophobic anchor via one or more covalent bonds. Hydrophilic, in this context, refers to a moiety of the polymer, lipidic material, or carbohydrate which orients itself towards an aqueous or hydrophilic environment. Hydrophobic, in this context, refers to a moiety which orients itself away from an aqueous or hydrophilic environment, and towards a non-aqueous (e.g., gaseous core) environment. In certain embodiments, the hydrophobic anchor is a lipid group $R^L$, as described herein.

The prevention of aggregation involves two main methods for stabilization, electrostatic and steric stabilization. In electrostatic the particles are made to repel each other, in steric the particles have large polymers (like polyethylene glycol) sprouting from there surfaces to physically prevent aggregation. It is also possible to enhance the viscosity of the solution in which the particle are immersed as to physically prevent touching. Other types of stabilization refer to prevention of degradation of the particle or the drug it houses. For instance, tocopherol prevents lipid oxidation. Also some humidity reducing agents that stops hydrolysis of PLGA are useful for this purpose.

The concentration of each of the various stabilizing agents can vary and optional concentrations can be determined via routine methodology. In certain embodiments, the stabilized membrane comprises from 0.1 to 20%, or from 5 to 10% of a stabilizing agent.

Detergents

A wide variety of detergents can be used as a component of the particle, e.g., provided in the stabilized membrane and/or the sheath membrane. Detergents, as used herein, include emulsifiers, surfactants, and wetting agents. Some detergents may also be used as stabilizing agents.

Polymers

The stabilized membrane and or sheath membrane may be composed of one or more polymers. A wide variety of polymers can be used as a component (or as the sole constituent) of the particle, e.g., provided in the stabilized membrane and/or the sheath membrane. A polymer is a chemical compound or mixture of compounds composed of structural units created through polymerization. Polymers include but are not limited to natural/biological and synthetic polymers. Polymers may be branched or unbranched.

In certain embodiments, the polymer is modified, e.g., by substitution or comprising a group X or Y attached to the material, to form covalent crosslinkages, and/or by substitution with a lipid tail $R^L$.

Exemplary polymers include, but are not limited to, proteins, carbohydrates, poly(hydroxy acids) (e.g., poly(lactic acid), poly(glycolic acid), and poly(lactic-co-glycolic acid) (PGLA), polyglycolides, polylactides, polylactide coglycolide copolymers and blends, polyanhydrides, polyorthoesters, polyglutamic acid (PG), polyamides, polycarbonates, polyalkylenes such as polyethylene and polypropylene, polyalkylene glycols such as poly(ethylene glycol), polyalkylene oxides such as poly(ethylene oxide), polyalkylene terepthalates such as poly(ethylene terephthalate), polyvinyl alcohols, polyvinyl ethers, polyvinyl esters, polyvinyl halides such as poly(vinyl chloride), polyvinylpyrrolidone, polysiloxanes, poly(vinyl alcohols), poly (vinyl acetate), polystyrene, polyurethanes and co-polymers thereof, derivativized celluloses such as alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium salt (jointly referred to herein as "synthetic celluloses"), polymers of acrylic acid, methacrylic acid or copolymers or derivatives thereof including esters, poly (methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate) (jointly referred to herein as "polyacrylic acids"), poly(butyric acid), poly(valeric acid), and poly(lactide-co-caprolactone), polyallylamines, copolymers and blends thereof. As used herein, "derivatives" include polymers having substitutions, additions of substituents, for example, alkyl, alkenyl (e.g., vinyl, allyl), alkynyl, carbocylyl, heterocyclyl, aryl, heteroaryl, etc. modifications by hydroxylations, oxidations (e.g., oxidation to provide —CHO or —CO$_2$H functionalization), and others routinely made by those skilled in the art.

The polymers may be provided in a variety of configurations, including cyclic, linear and branched configurations. Branched configurations include star-shaped configurations (e.g., configurations in which three or more chains emanate from a single branch point), comb configurations (e.g., graft polymers having a main chain and a plurality of branching side chains), and dendritic configurations (e.g., arborescent and hyperbranched polymers). The polymers can be formed from a single monomer (i.e., they can be homopolymers), or they can be formed from multiple monomers (i.e., they can be copolymers) that can be distributed, for example, randomly, in an orderly fashion (e.g., in an alternating fashion), or in blocks. In many embodiments of the present invention, biodisintegrable polymers are employed. A "biodisintegrable material" is one that, subsequent to release within the subject, undergoes dissolution, degradation, resorption and/or other disintegration processes.

Further examples of polymers for use in conjunction with the present invention, not necessarily exclusive of those listed above, and which may be repetitive, many of which are readily biodisintegrable, include, but are not limited to, cellulosic polymers and copolymers, for example, cellulose ethers such as methylcellulose (MC), hydroxyethylcellulose (HEC), hydroxypropyl cellulose (HPC), hydroxypropyl methyl cellulose (HPMC), methylhydroxyethylcellulose (MHEC), methylhydroxypropylcellulose (MHPC), carboxymethyl cellulose (CMC) and its various salts, including, e.g., the sodium salt, hydroxyethylcarboxymethylcellulose (HECMC) and its various salts, carboxymethylhydroxyethylcellulose (CMHEC) and its various salts, other polysaccharides and polysaccharide derivatives such as starch (e.g., Hetastarch), dextran, dextran derivatives, chitosan, and alginic acid and its various salts, carageenan, varoius gums, including xanthan gum, guar gum, gum arabic, gum karaya, gum ghatti, konjac and gum tragacanth, glycosaminoglycans and proteoglycans such as hyaluronic acid and its salts, proteins such as gelatin, collagen, albumin, and fibrin, other polymers, for example, polyhydroxyacids such as polylactide, polyglycolide, polyl(lactide-co-glycolide) and poly(epsilon.-caprolactone-co-glycolide)-, carboxyvinyl polymers and their salts (e.g., carbomer), polyvinylpyrrolidone (PVP), polyacrylic acid and its salts, polyacrylamide, polyacilic acid/acrylamide copolymer, polyalkylene oxides such as polyethylene oxide, polypropylene oxide, poly(ethylene oxide-propylene oxide), poloxomers, polyoxyethylene (polyethylene glycol, PEG), PEGylated lipids, polyanhydrides, polyvinylalchol, polyethyleneamine and polypyrridine, additional salts and copolymers thereof.

Examples of non-biodegradable polymers include ethylene vinyl acetate, poly(meth)acrylic acid, polyamides, copolymers and mixtures thereof.

Examples of preferred biodegradable polymers include polymers of hydroxy acids such as lactic acid and glycolic acid polylactide, polyglycolide, polylactide co glycolide, and copolymers with PEG, polyanhydrides, poly(ortho)esters, polyurethanes, poly(butyric acid), poly(valeric acid), and poly(lactide-co-caprolactone). In general, these materials degrade in vivo by both non-enzymatic and enzymatic hydrolysis.

Bioadhesive polymers of particular interest for use in imaging of mucosal surfaces, as in the gastrointestinal tract, include polyanhydrides, polyacrylic acid, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

In some embodiments, the polymer is a poloxamer. Poloxamers are nonionic triblock copolymers composed of a central hydrophobic chain of polyoxypropylene (also known as poly(propylene oxide)) flanked by two hydrophilic chains of polyoxyethylene (also known as poly(ethylene oxide)). The three digit number 188 indicates the approximate molecular mass of the polyoxypropylene core (i.e., 1800 g/mol) and the polyoxyethylene content (i.e., 80%). Poloxamers are commercially available, e.g., provided by BASF Corporation. Exemplary poloxamers include, but are not limited to, PLURONIC® F68, PLURONIC® F108, PLURONIC® F127, PLURONIC® F38, PLURONIC® F68, PLURONIC® F77, PLURONIC® F87, PLURONIC® F88, PLURONIC® F98, PLURONIC® L10, PLURONIC® L101, PLURONIC® L121, PLURONIC® L31, PLURONIC® L35, PLURONIC® L43, PLURONIC® L44, PLURONIC® L61, PLURONIC® L62, PLURONIC® L64, PLURONIC® L81, PLURONIC® L92, PLURONIC® N3, PLURONIC® P103, PLURONIC® P104, PLURONIC® P105, PLURONIC® P123, PLURONIC® P65, PLURONIC® P84, and PLURONIC® P85. In certain embodiments, the polymer is PLURONIC® F68 (poloxamer 188), PLURONIC® F108 (poloxamer 338), or PLURONIC® F127 (poloxamer 407), In certain embodiments, the polymer is a polyethylene glycol (PEG) polymer, such as a PEGylated lipid. Exemplary PEGylated lipids include, but are not limited to, PEG-stearate, 1,2-Distearoyl-sn-glycero-3-Phosphoethanolamine-N-[Methoxy(Polyethylene glycol)-1000], 1,2-Distearoyl-sn-glycero-3-Phosphoethanolamine-N-[Methoxy(Polyethylene glycol)-2000], and 1,2-Distearoyl-sn-glycero-3-Phosphoethanolamine-N-[Methoxy(Polyethylene glycol)-5000]. In certain embodiments, the polymer is PEG-stearate.

In certain embodiments, any one of the polymers as described herein is modified or comprise one or more X and Y groups to provide a crosslinkable polymer. In certain embodiments, the membrane and/or sheath membrane is a crosslinked polymer (e.g., functionalized with one or more groups X and Y to form a crosslink A) as described herein.

In certain embodiments, the X and Y groups are acrylate groups. For example, in one particular embodiment, the polymer is a poloxamer modified with one or more acrylate groups, such as pluronic F127 diacrylate. In certain embodiments, the polymer is polyglutamic acid (PG) or poly(lactic-co-glycolic acid) (PLGA), wherein one or more free carboxylic acids attached to the polymer backbone are optionally modified as acrylate groups.

Proteins are a type of polymer and may form the basis of the stabilized membrane.

In certain embodiments, the protein is modified, e.g., by substitution or comprising a group X or Y attached to the material, to form covalent crosslinkages, and/or by substitution with a lipid tail $R^L$. It is understood that "polypeptide" or "protein" are used interchangeably and refer to a string of at least three amino acids linked together by peptide bonds. Proteins may contain only natural amino acids, although non-natural amino acids (i.e., compounds that do not occur in nature but that can be incorporated into a polypeptide chain) and/or amino acid analogs as are known in the art may alternatively be employed. One or more of the amino acids in a protein may be modified, for example, by the addition of a chemical entity such as a carbohydrate group, a phosphate group, a farnesyl group, an isofarnesyl group, a fatty acid group, a linker for crosslinking, functionalization, or other modification.

Proteins include, for example, lipophilic and amphiphilic proteins, fibrous proteins (e.g., cytoskeletal proteins such as actin, keratin, collagen, gelatin, extracellular matrix proteins such as elastin), globular proteins (e.g., plasma proteins such as serum albumin, coagulation factors, acute phase proteins), hemoproteins, cell adhesion proteins, transmembrane transport proteins, immune system proteins (e.g., immunoglobulins (antibodies)), lung surfactant proteins (e.g., SP-A, SP-B, SP-C, or SP-D, synthetic lung surfactant proteins, lung surfactant protein mimetics), and enzymes.

In certain embodiments, the protein is a cytoskeletal protein such as gelatin.

In certain embodiments, the protein is a globular protein such as an albumin protein. In certain embodiments, the albumin protein is human serum albumin or bovine serum albumin (BSA).

In certain embodiments, any one of the proteins as described herein is modified or comprise with one or more X and Y groups to provide a crosslinkable protein. In certain embodiments, the membrane and/or sheath membrane is a crosslinked protein (e.g., functionalized or comprising one or more groups X and Y to form a crosslink A) as described herein.

In certain embodiments, the X and Y groups are thiol groups, and upon oxidation form a disulfide bond. For example, in one particular embodiment, the protein is albumin with cysteine groups which react, under oxidative conditions to form a crosslinked albumin protein.

Carbohydrates or sugars may also be used as a component of the particle, e.g., provided in the stabilized membrane and/or the sheath membrane.

The terms "sugar," "polysaccharide," and "carbohydrate" may be used interchangeably, and generally have the molecular formula $C_nH_{2n}O_n$. A carbohydrate may be a monosaccharide, a disaccharide, trisaccharide, oligosaccharide, or polysaccharide. The most basic carbohydrate is a monosaccharide in the D, L, cyclic or acyclic form, such as glucose (e.g., D-glucose, also known as dextrose), sucrose, galactose, mannose, ribose, arabinose, xylose, and fructose. Disaccharides are two joined monosaccharides. Exemplary disaccharides include sucrose, maltose, cellobiose, and lactose. Typically, an oligosaccharide includes between three and six monosaccharide units (e.g. raffinose, stachyose), and polysaccharides include six or more monosaccharide units. Exemplary polysaccharides include starch, glycogen, and cellulose. In certain embodiments, the carbohydrate is modified, e.g., by substitution or comprising a group X or Y attached to the material, to form covalent crosslinkages, and/or by substitution with one or more lipid tails $R^L$. Carbohydrates may further contain modified saccharide units such as 2'-deoxyribose wherein a hydroxyl group is removed, 2'-fluororibose wherein a hydroxyl group is replace with a fluorine, or N-acetylglucosamine, a nitrogen-containing form of glucose (e.g., 2'-fluororibose, deoxyribose, and hexose). Carbohydrates may exist in many different forms, for example, conformers, cyclic forms, acyclic forms, stereoisomers, tautomers, anomers, and isomers.

In certain embodiments, the carbohydrate is lactose or glucose (e.g., dextrose).

In certain embodiments, any one of the carbohydrates as described herein is modified or comprise with one or more X and Y groups to provide a crosslinkable sugar. In certain embodiments, the membrane and/or sheath membrane is a carbohydrate shell or membrane, e.g., a shell or membrane formed from modified carbohydrate (e.g., a carbohydrate modified with one or more lipid $R^L$ groups, such as sucrose stearate or crosslinked carbohydrate (e.g., functionalized or comprising one or more groups X and Y to form a crosslink A)).

In certain embodiments, the X and Y groups are acrylate groups. For example, in one particular embodiment, the carbohydrate is a sugar modified with one or more acrylate groups, such as starch modified with acrylate groups, which react to form a crosslinked carbohydrate.

Monomers

Monomers (or the building blocks of polymers) may also be used as a component of the particle. Monomers include for instance, the building blocks of sugars, such as sucrose and lactose.

Other Agents

Steroids

Steroids may also be used as a component of the particle, e.g., provided in the stabilized membrane and/or the sheath membrane. Some steroids may also be used as stabilizing agents, e.g., sterols such as cholesterol. In certain embodiments, the membrane comprises cholesterol; however, in certain embodiments, the membrane does not include cholesterol. In certain embodiments, the steroid is modified, e.g., by substitution or comprising a group X or Y attached to the steroid, to form covalent crosslinkages, and/or by substitution with one or more lipid tails $R^L$.

Anti-Oxidants

In certain embodiments, the stabilized membrane and/or the external crosslinked shell further comprises an anti-oxidant (e.g., non-enzymatic anti-oxidant). Exemplary anti-oxidants include, but are not limited to, tocopherol (vitamin E), vitamin A, glutathione, carotenoids (e.g. lycopene, lutein, polyphenols, β-carotene), flavonoids, flavones, flavonols, glutathione, N-acetyl cysteine, cysteine, lipoic acid, ubiquinal (coenzyme Q), ubiquinone (coenzyme Q10), melatonin, lycopene, butylated hydroxyanisole, butylated hydroxytoluene (BHT), benzoates, methyl paraben, propyl paraben, proanthocyanidins, mannitol, and ethylenediamine tetraacetic acid (EDTA).

In certain embodiments, the anti-oxidant is tocopherol.

Cryoprotectants

In certain embodiments, the stabilized membrane and/or the external crosslinked shell further comprises a cryoprotectant. A cryoprotectant is a substance that is used to protect a material from freezing damage biological tissue from freezing damage. Cryoprotectants may also function by lowering the glass transition temperature of a material. In this way, the cryoprotectant prevents actual freezing, and the material maintains some flexibility in a glassy phase. Many cryoprotectants also function by forming hydrogen bonds with biological molecules as water molecules are displaced. Exemplary cryoprotectants include, but are not limited to, glycols (alcohols containing at least two hydroxyl groups, such as ethylene glycol, propylene glycol, and glycerol), dimethyl sulfoxide (DMSO), and sugars such as sucrose.

Gas Core

As generally understood from the present disclosure, the gas core of the particle contains one or more gases. The gas core is the gas encapsulated within the stabilized membrane. In certain embodiments, the gas core does not contain a fluorinated gas. In certain embodiments, the gas core does not contain a perfluorocarbon based liquid. In certain embodiments, the gas core does not contain a hemoglobin, e.g., a natural or synthetic hemoglobin.

In certain embodiments, the gas is a biological gas, e.g., a gas used for therapeutic purposes.

In this context, the gas must be pharmacologically acceptable, i.e., must be biocompatible and have minimal toxicity when released. Preferably the gas is able to diffuse through the envelope following administration. Exemplary gases include, but are not limited to, nitrogen, carbon dioxide, nitric oxide, helium, inhalational anesthetics (e.g., isoflurane), and neuroprotective gases (e.g., argon or xenon or hydrogen sulfide.

In other embodiments, the gas is not a biological gas, and is useful for non-therapeutic purposes.

The gas may be in the gas core alone or in combination with one or more other gases. For example, the gas core may contain a gas mixture containing oxygen and one or more additional gases. In certain embodiments, the gas is oxygen. In certain embodiment the gas is a mixture of oxygen and another gas. In certain embodiments, the gas contained within the particle may be a biological gas other than oxygen, including, but not limited to, nitric oxide, and inhalational anesthetics, such as isoflurane.

In certain embodiments, the volume of the gas core comprises about 10%, 20%, 30%, 40%, 50%, 60%, 70%, 80% 90%, 95%, 99%, 99.9% or 99.99% of gas, e.g., the volume of the gas core comprises between about 10% to about 99.99%, inclusive, of gas. In certain embodiments, the volume of the gas core is 50 to 60% of the overall volume of the suspension. In certain embodiments, lower volume percentages are preferred, e.g., between about 5% to about 50% gas. Particle suspensions containing less than 50% gas (by volume), may be useful when resuscitation is desired in trauma, or in microvascular flaps being treated with particles. In some embodiments, the gas content in a concentrated suspension is at least 10%, 20%, 30%, 40%, 50%, 60% (e.g., 70%, 80%, or 90%) by volume.

Pressurized Gas

The gas filled particles may be pressurized. In a pressurized gas particle the amount of gas per particle can be increased significantly. Pressurization techniques for making gas filled polymers that are pressurized are known in the art and for instance are described in patents such as U.S. Pat. No. 4,344,787.

Particle Size

As understood from the disclosure, particle and microparticle are used interchangeably herein. A microparticle has a particle diameter of between about 0.001 microns to about 500 microns. In certain embodiments, the particle has a diameter of about 0.02 microns to about 50 microns, e.g., about 0.05 microns to 40 microns, about 0.05 microns to 30 microns, about 0.05 microns to 20 microns, about 0.05 microns to 10 microns, about 0.05 microns to 6 microns, about 0.05 microns to 5 microns, about 0.05 microns to 4 microns, about 0.05 microns to 3 microns, about 0.05 microns to 1 micron, about 0.05 microns to 0.5 microns, 5 microns to 10 microns, 2 microns to 5 microns, 2 microns to 3 microns, 0.05 microns to 1 micron, or about 0.1 microns to 3 microns, inclusive.

In certain embodiments, 90% of the particles of a batch are within the above recited diameters (referred to as the "D90").

The overall diameter of the particle is selected to provide a high surface area to volume ratio, thereby favoring rapid transfer of the gas out of the particles.

For example, for delivery of oxygen to a patient, typically, the particle has diameters of about 20 microns or smaller, preferably the upper limit for the diameter of the particles ranges from 15 microns or smaller, or 10 microns or smaller in order to pass through the pulmonary capillary bed following intravenous injection. In certain embodiments, the diameter below which 90% of the particles share (D90) is between about 2 to about 3 microns, inclusive, for intravenous particles. In certain embodiments, the diameter below which 90% of the particles share (D90) is between about between about 0.001 microns and about 1 micron, inclusive, for inhalational particles.

The size of these particles can be determined using a suitable device, e.g., Accusizer® or Multisizer® III. Microscopy can be applied to directly visualize the particles in the concentrated suspension. Dynamic light scattering may be used for particles less than 2 microns. Accusizer using light obscuration may be used to examine larger particles.

Stabilized Membrane and Sheath Membrane

As generally understood from the present disclosure, the present invention provides particles which comprise a stabilized membrane which encapsulates a gas, and which further includes a sheath membrane.

In certain embodiments, the width of the stabilized membrane is between 1 and 100 nm thick, between 1 and 10 nm thick, or between 2 and 5 nm thick, inclusive. In certain embodiments, the stabilized membrane is a monolayer about 10 nm thick. A thin stabilized membrane affords a high permeability to oxygen, while preventing a direct gas-blood interface.

Likewise, in certain embodiments, the width of the membrane is between 1 and 100 nm thick, between 1 and 10 nm thick, or between 2 and 5 nm thick, inclusive. In certain embodiments, the membrane is a hydrogel or polymer about 10 nm thick.

In certain embodiments, the nature of the stabilized membrane and/or sheath membrane imparts a stability to the particle, wherein the shelf-life is greater than 6 months, e.g., greater than 7 months, 8 months, 9 months, 10 months, 11 months, or 12 months (1 year). In certain embodiments, the shelf-life of the particle is greater than 1 year, e.g., 1.5 years, 2 years, 2.5 years, or more.

Pharmaceutical Compositions and Suspensions

As generally understood from the present disclosure, the particles as described herein may be formulated as a pharmaceutical composition for administration or as a suspension (e.g., emulsion) for storage.

Pharmaceutical compositions and suspensions of the particle may comprise a pharmaceutically acceptable excipient, which, as used herein, includes any and all solvents, dispersion media, diluents, or other liquid vehicles, dispersion or suspension aids, surface active agents, isotonic agents, viscosity enhancing agents (e.g., thickening agents), preservatives, solid binders, lubricants and the like, as suited to the particular formulation desired. Remington's The Science and Practice of Pharmacy, 21st Edition, A. R. Gennaro, (Lippincott, Williams & Wilkins, Baltimore, Md., 2006; incorporated herein by reference) discloses various excipients used in formulating compositions and suspensions and known techniques for the preparation thereof. Except insofar as any conventional excipient is incompatible with a substance or its derivatives, such as by producing any undesirable biological effect or otherwise interacting in a deleterious manner with any other component(s) of the compositions or suspensions, its use is contemplated to be within the scope of this invention.

In some embodiments, the pharmaceutically acceptable excipient is at least 95%, 96%, 97%, 98%, 99%, or 100% pure. In some embodiments, the excipient is approved for use in humans and for veterinary use. In some embodiments, the excipient is approved by United States Food and Drug Administration. In some embodiments, the excipient is pharmaceutical grade. In some embodiments, the excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of the compositions and suspensions include, but are not limited to, inert diluents, dispersing agents, surface active agents and/or emulsifiers, disintegrating agents, preservatives, buffering agents, lubricating agents, and/or oils. Excipients such as coloring agents can be present in the compositions or suspensions, according to the judgment of the formulator.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc. and combinations thereof.

Exemplary dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, crosslinked poly(vinyl-pyrrolidone) (crospovidone), sodium carboxymethyl starch (sodium starch glycolate), carboxymethyl cellulose, crosslinked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary preservatives may include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, ascorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid. Exemplary alcohol preservatives include, but are not limited to, ethanol, polyethylene glycol, phenol, phenolic compounds, bisphenol, chlorobutanol, hydroxybenzoate, and phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus®, Phenonip®, methylparaben, Germall 115, Germaben II, Neolone™, Kathon™, and Euxyl®. In certain embodiments, the preservative is an antioxidant. In other embodiments, the preservative is a chelating agent.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc. and combinations thereof.

The compositions and suspensions as described herein should be generally isotonic with blood. Thus the compositions and suspensions may also contain small amounts of one or more isotonic agents. The isotonic agents are physiological solutions commonly used in medicine and they comprise water, aqueous saline solution, e.g. 0.9% NaCl, 2.6% glycerol solution, lactated Ringer's solution, and 5% dextrose solution, biologically compatible organic solvents (e.g., DMSO), and/or commercially available intravenous fluid or blood.

The compositions and suspensions may also be mixed with volume expanders, such as Hextend, hetastarch, albumin, 6% Hydroxyethyl Starch in 0.9% Sodium Chloride Infusion (Voluven), etc. The compositions and suspensions can also be mixed with blood (e.g. packed red blood cells) or hemoglobin-based oxygen carriers. Additionally, the compositions and suspensions can be mixed in a physiologic buffer (e.g. tris(hydroxymethyl) aminomethane, "THAM"). This is particularly useful in a clinical situation of impaired ventilation. In other embodiments, the compositions and suspensions can contain one or more cryoprotectants, e.g., glycols such as ethylene glycol, propylene glycol, and glycerol. The compositions or suspensions may further comprise an aqueous solution comprises a calcium salt for enhanced stability.

The particles may also be suspended in a medium (e.g., an aqueous and/or organic medium) comprising a viscosity enhancing agent. Such particles may also be prepared in such a medium, as further described herein. Exemplary viscosity enhancing agents for use as a component of a storage medium and/or a preparative medium include, but are not limited to, corn syrup (e.g., Clearsweet corn syrup (CS)); glycerin; cellulose derivatives (e.g., methylcellulose (MC); hydroxypropylmethylcellulose (HPMC); carboxymethylcellulose (CMC); microcrystalline cellulose (CC); ethyl cellulose; hydroxyethyl cellulose (HEC); hydroxypropyl cellulose (HPC); cellulose); gelatin; starch; hetastarch; poloxamers; pluronics; sodium CMC; sorbitol; acacia; povidone; carbopol; polycarbophil; chitosan; alginate; chitosan glutamate; hyaluronic acid; elastin; hyaluronan; maltodextrin DE; deoxyglycocholate (GDC); polymethacrylic acid; glycols (e.g., polymethylene glycol; polyethylene glycol); cyclodextrins (e.g., sulfobutylether B cyclodextrin); sodium tauro-dihydrofusidate (STDHF); and N-trimethyl chitosan chloride (TMC). In certain embodiments, the viscosity enhancing agent is corn syrup (e.g., Clearsweet corn syrup (CS)) or glycerin.

In certain embodiments, the particles are suspended in a medium (e.g., an aqueous and/or organic medium) comprises between about 5% to about 90% by weight of one or more viscosity enhancing agents, e.g., between about 5% to about 85%, between about 5% to about 80%, between about 5% to about 75%, between about 5% to about 70%, between about 5% to about 65%, between about 5% to about 60%, between about 5% to about 55%, between about 5% to about 50%, between about 5% to about 45%, between about 5% to about 40%, between about 10% to about 80%, between about 15% to about 80%, between about 20% to about 80%, between about 25% to about 80%, between about 30% to about 80%, between about 35% to about 80%, between about 40% to about 80%, between about 45% to about 80%, between about 50% to about 80%, or between about 25% to about 75%, inclusive.

As generally understood from the above, the medium (e.g., an aqueous medium and/or organic medium) which comprises one or more viscosity enhancing agents is a viscous medium. A viscous medium is defined as a fluid whose viscosity is sufficiently large to make viscous forces.

In certain embodiments, the gas-filled microparticle compositions and suspensions described above can be formulated in a manner suitable for topical administration, e.g., as a liquid and semi-liquid preparation that can be absorbed by the skin. Examples of a liquid and semi-liquid preparation include, but are not limited to, topical solutions, liniments, lotions, creams, ointments, pastes, gels, and emugels.

In certain embodiments, the particle and/or pharmaceutical composition comprising the particle further includes a therapeutic agent, e.g., which can be, but are not limited to, hydrophilic or hydrophobic drugs, lipid-soluble drugs, nucleotide acid-based drugs such as siRNAs or microRNAs, protein drugs such as antibodies, or free radical scavengers. In certain embodiments, the compositions and suspensions are co-formulated with one or more additional therapeutic agents for co-delivery of the gas or gas mixture inside the microparticles and the one or more agents, which can be, but are not limited to, hydrophilic or hydrophobic drugs, lipid-soluble drugs, nucleotide acid-based drugs such as siRNAs or microRNAs, protein drugs such as antibodies, or free radical scavengers. In certain embodiments, the therapeutic agent is encapsulated in the core of the particle. Alternatively, in certain embodiments, the particle comprises a therapeutic agent attached to the outer surface of the particle, e.g., by covalent attachment or by non-covalent association with the membrane.

Any of the particle-containing suspension described herein can be either in suspension form or in dry powder form (e.g., obtained via spray drying or by lyophilization). When in dry powder form, the suspension can be mixed with a solution such as saline immediately before use.

The gas-filled particle compositions or suspensions described above can be used for gas delivery shortly after their preparation. If needed, they can be stored under suitable conditions (e.g., refrigerated conditions) before administration.

Additional methods of preparing these suspensions, dry particles and powers, and filling the particles with gas are described herein. See, for example, the methods of preparation and the Examples.

Further contemplated are kits or pharmaceutical packs comprising a particle and instructions for use. In certain embodiments, the kit comprises a container housing a particle, a container housing a pressurized aqueous phase mixture, and instructions for mixing the particle and the aqueous phase. In certain embodiments, the container housing the particle and the container housing the aqueous phase are separate compartments within a single container.

Methods of Treatment and Use

As generally understood from the present disclosure, provided are methods of delivering a gas to a subject in need thereof, the method comprising administering to the subject a pharmaceutical composition comprising a particle as described herein and a pharmaceutically acceptable excipient. The gas-filled particles described herein can be used to deliver a gas into a subject, thereby treating various diseases and conditions. The gas-filled particles may be administered to any subject, tissue or organ in need thereof, i.e., in need of the gas to be delivered, e.g., by intravenous, intraosseous, or intraarterial injection; alternatively it can be topically applied as a powder or wetted, or inhaled, ingested or applied topically to a body cavity, such as the pleura, the pericardium or the peritoneum or administered periotenal or retroperitoneal. The particles may be administered alone or in combination with other treatments as an adjunctive therapy. Depending upon the need of a subject, the particle can be designed such that they release the gas or gas mixture immediately following administration (e.g., <10 milliseconds to 1 minute). Alternatively, the particles can be designed to provide sustained release of the gas or gas mixture, and/or to persist in vivo until they reach the target tissue, where the membrane collapses to release the gas or gas mixture.

The term "treating" as used herein refers to the application or administration of a composition including one or more active agents to a subject, who has a target disease or disorder, a symptom of the disease/disorder, or a predisposition toward the disease/disorder, with the purpose to cure, heal, alleviate, relieve, alter, remedy, ameliorate, improve, or affect the disease/disorder, the symptoms of the disease/disorder, or the predisposition toward the disease/disorder.

A "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds.

In certain embodiments, the subject is or is suspected of experiencing local or systemic hypoxia. In certain embodiments, the subject has or is suspected of having a disease or disorder selected from the group consisting of congenital physical or physiologic disease, transient ischemic attack, stroke, acute trauma, cardiac arrest, exposure to a toxic agent, heart disease, hemorrhagic shock, pulmonary disease, acute respiratory distress syndrome, infection, and multi-organ dysfunction syndrome.

An "effective amount" is the amount of the particles that alone, or together with one or more additional therapeutic agents, produces the desired response, e.g. increase in the local or systemic level of a desired gas such as oxygen in a subject or increases the tissue PO2 in a particular target organ. In the case of treating a particular disease or condition, the desired response can be inhibiting the progression of the disease/condition. This may involve only slowing the progression of the disease/condition temporarily, although more preferably, it involves halting the progression of the disease/condition permanently. This can be monitored by routine methods. The desired response to treatment of the disease or condition also can be delaying the onset or even reducing the risk of the onset of the disease or condition. An effective amount will depend, of course, on the particular disease/condition being treated, the severity of the disease/condition, the size of the patient, the volume of distribution of the drug, the individual patient parameters including age, physical condition, size, gender and weight, the duration of the treatment, the nature of concurrent therapy (if any), the specific route of administration and like factors within the knowledge and expertise of a health practitioner. These factors are well known to those of ordinary skill in the art and can be addressed with no more than routine experimentation. It is generally preferred that a moderate dose of the particles be used, that is, the highest safe dose according to sound medical judgment, taking into account that following a hypoxic injury, for example, an excessive or even normal oxygen tension may be harmful during the recovery period.

Therapeutic Applications of Gas-Filled Particles

Suspensions containing oxygen-filled particles as described herein can be used to restore the oxygen level in a patient experiencing or being suspected of experiencing local or systemic hypoxia via any of the methods described above. Thus, they have broad therapeutic utilities, including treatment of traumatic brain injury, cardiac arrest (via either intraarterial infusion or intravenous infusions), promotion of wound healing, topical augmentation of oxygen delivery (as topically administered to a body cavity or enterally administered) and preservation of organs during transplant.

After the gas-filled particles are delivered into a subject, the gas core reaches an equilibrium across the membrane between the gas core and the surrounding plasma, which may include desaturated hemoglobin. When the gas core contains oxygen, it binds rapidly to hemoglobin, which provides an "oxygen sink." This strongly favors a tendency of oxygen to leave the particle's core rather than remain within it. When particles reach capillaries intact, they may oxygen may equilibrate directly with surrounding tissues without interposed hemoglobin as an oxygen carrier.

Fully saturated whole blood with physiologic hemoglobin contains 16-20 mL oxygen per dL. Particle suspensions can be manufactured to contain between 40 and 70 mL oxygen per dL of suspension. Thus, the injection of one dL of suspension can deliver about 40-70 mL of oxygen directly to a tissue or organ in need of immediate oxygenation. In certain embodiments, oxygen is delivered at an infusion rate of 10 to 400 mL/minute to the subject.

The particles may be administered in an effective amount and at suitable rate for increasing or maintaining the $PO_2$ in a subject following administration. Typically, the particles are administered in an effective amount and at suitable rate to deliver an effective amount of oxygen to a subject to ischemic tissues or to desaturated blood in a time ranging from 0.5 to 30 seconds following administration, wherein the amount of oxygen that is delivered is effective to restore $PO_2$ levels to normal levels or prevent or alleviate hypoxic injury. In certain embodiments, the particles provide sustained release of oxygen; such particles may be used, for example, to deliver oxygen or other gas to the brain and other tissues.

Cerebral Protectant During Childbirth

An effective amount of suspension containing oxygen- or other gas-filled particles and optionally other therapeutic agents can be administered into the epidural, subdural, or subarachnoid (or nearby) spaces during intrapartum distress so as to maintain sufficient oxygen supply to the neonate, thereby reducing the risk of cerebral damage during childbirth.

Provide Oxygen Supplementation Via the Enteral Route

Oxygen-filled particles and, optionally, lipid nutrients, carbohydrates, or other nutrients found in blood (e.g., glucose and other blood components), can be delivered via the enteral route, e.g., to a site in the abdominal cavity, such as the intestine or the peritoneum, to provide an alternate source of intestinal oxygenation and prevents or mitigates intestinal ischemia, which may contribute to necrotizing enterocolitis, a leading cause of pediatric morbidity and mortality in preterm infants. This may also decrease the burden of anaerobic bacteria in the bowel, decreasing the risk of bacterial translocation and sepsis. This can also benefit prematurely born infants as it may decrease toxicity to premature lungs, prevents retinopathy of prematurity, and also provides lipid nutrition at the same time. In addition, it may be used in adults such as COPD patients, who require supplemental oxygen for some reason. It may also provide an alternative method of providing supplemental oxygen to critically ill patients such as ARDS patients, in whom increasing oxygen delivery through the lungs may be prohibitively injurious.

Preservation of Organ and Blood In Vitro

Low blood oxygen tensions within stored blood may contribute to the blood storage defect, causing cells within the plasma to generate lactate and toxins, which may decrease the therapeutic value of transfused blood and diminish its shelf life. Oxygen-filled particles may be added to a blood sample periodically to prolong in vitro blood storage. In an explanted organ, a suspension containing oxygen-filled particles can be delivered into a blood vessel in an organ to provide oxygen supply, thereby ameliorating tissue damage due to hypoxia. This is particularly useful in preserving organs to be used in transplantation. In addition, oxygen-filled particles can be added to a blood sample periodically to prolong in vitro blood storage.

Promote Wound Healing

Delivery of oxygen-filled particles to a wound site or a site nearby a wound can provide a continuous supply of oxygen to the wounded tissue, which is essential to the healing process. Thus, this approach benefits healing of a wound, such as that associated with a disease or disorder (e.g., diabetes, peripheral vascular disease, or atherosclerosis). In some embodiments, the suspension is prepared as a topical formulation for treating external wounds. The wound may be, for instance, a burn. The invention also contemplates bandages or would healing devices comprising the particles of the invention.

Improve Efficacy of Tumor Radio Therapy and Reduce Side Effects Caused Thereby

Tumor radio therapy often damages non-cancerous tissues nearby a tumor site. Applying an effective amount of oxygen-filled particles delivered locally or systemically can reduce such damage by increasing the oxygen content of a local tumor environment. In addition, it also can increase the effects of ionizing radiation delivered to the tumor, thereby improving efficacy of a radio therapy. In some embodiments, the particles are delivered directly to a tumor site. In others, the particles are administered to a site nearby a tumor.

Ameliorate Sickle Cell Crisis

Sickle cell crisis refers to several independent acute conditions occurring in patients with sickle cell anemia, including acute chest syndrome (a potentially lethal condition in which red blood cells sickle within the lungs and lead to necrosis, infection and hypoxemia), vasoocculsive crisis (i.e., obstruction in circulation caused by sickled red blood cells, leading to ischemic injuries), aplastic crisis (acute worsening of the baseline anemia in a patient, causing pallor, tachycardia, and fatigue), splenic sequestration crisis (acute, painful enlargements of the spleen), and hyper haemolytic crisis (acute accelerated drops in haemoglobin level). Administering an effective amount of oxygen-filled particles to a sickle cell anemia patient or a subject suspected of having the disease can reduce sickle cell crisis, in particular, vaso-occlusive crisis, in part because the sickle crisis is perpetuated by local and regional hypoxemia.

Improve Anti-Infective Activity of Immune Cells

Oxygen-filled particles can be preferentially taken up by lymphocytes of varying types, including macrophages so as to raise intracellular oxygen tension. This may potentiate lymphocyte killing of microbial agents by enabling superoxide dismutase and the production of intracellular free radicals for microbicidal activity without causing resistance.

Treatment of Anaerobic Infections

Administration of oxygen-filled microparticles via the topical, intravenous, intraarterial, intradermal, intramuscular, enteral or other route may provide a potent mechanism to counter anaerobic infections. This mechanism may be particularly attractive due to its alternative mechanism of action—this is unlikely to be countered by typical bacterial resistance mechanisms.

Minimize Organ Injury During Cardiopulmonary Bypass in Adults, Children, and Neonates During cardiopulmonary bypass operations, the heart must be cross-clamped (i.e. no oxygen delivery to the myocardium) and cooling/protective agents reduce myocardial oxygen consumption. Additionally, some portions of the surgery in neonates and children utilize deep hypothermic circulatory arrest in which all of the blood is removed from the body and all cannulas removed. Use of oxygen-filled particles to add a small amount of oxygen supply on a continuous basis to organs or to the blood used to deliver the cold cardioplegia solution would better protect the heart, brain and other organs and mitigate post-cardiac bypass injury. The majority of the oxygen-filled particles is gas, which could be consumed by the myocardium, leaving only a lipid shell and a small amount of carrier, if any. This is important because a large volume of perfusate cannot be used due to obscuration of the surgical field. This may provide a way to keep a clean surgical field while still providing oxygen to the myocardium, with or without hemoglobin as an intermediary.

For example, in one aspect, provided is a method of delivering a gas to a subject during cardiopulmonary bypass surgery, comprising administering to the subject during the surgery a pharmaceutical composition comprising a gas-filled particle. In certain embodiments, the pharmaceutical composition is administered to the blood of the subject. In certain embodiments, the pharmaceutical composition is administered to the blood upstream of a filtration device.

Oxygenate Venous Blood in Myocardial Infarction Patients

During a heart attack (myocardial infarction), an arterial thrombus prevents perfusion and therefore oxygen delivery to a selected region of myocardium. Perfusing the right atrium (through an intravenous injection) with highly oxygenated blood, via delivery of oxygen-filled particles, and providing a high coronary sinus pressure via a high right atrial pressure can back-perfuse a region of ischemic myocardium via the coronary sinus and venous plexus of the heart. The majority of the volume of the injectate (i.e., gas) will be consumed and disappear, allowing a continuous infusion into a dead-end space (i.e. a venous plexus feeding a region of myocardium previously fed by a thrombosed coronary artery, whether partially or completely obstructed. The thin-walled atrium may directly absorb oxygen from the oxygen-rich right atrial blood. In practice, using oxygen-filled particles can be an easy way to perfuse the heart with oxygen rich blood during acute coronary syndrome. For example, the oxygen-filled particles can be delivered using an occlusive balloon catheter blown up in the coronary sinus with a power-injection of oxygen-rich suspension into the coronary sinus such that the suspension could flow retrograde throughout the heart, including the region affected by the coronary thrombus (because there would be no clot on the venous side).

Cardiopulmonary Bypass Surgery

During cardiopulmonary bypass surgery the blood of a patient is circulated through a filtration device. The particles of the invention may be delivered directly to the patient or to the blood as it is being circulated outside of the body. In some embodiments the particles are administered upstream of a filtration device. An advantage of this embodiment is that the gas can be delivered to the blood and then the particles are removed by filtration before the blood is returned to the body.

Reduce Cardiac Arrhythmia During Coronary Angiography

Cardiac arrhythmia, even fatal arrhythmia, is a common adverse effect during coronary angiography in both adults and children for diagnostic or therapeutic purposes. Using an oxygen-filled particle suspension (e.g., of approximately 20 mL/dL oxygen) optionally mixed with a contrast agent allows for sustained oxygen delivery to sick myocardium during a selected injection of a coronary artery and prevents a substantial number of adverse events and deaths from these risky procedures.

Replace Blood During Bloody Procedures or in Early Resuscitation in Trauma

Oxygen-filled particles capable of translocating oxygen directly to mitochondria can be used as "blood replacement" during bloody procedures or in the early resuscitation in trauma. This would of course be a temporizing procedure such that the 'blood' lost via a bleeding source (e.g. the back during a spinal fusion, other arteries during many bloody procedures) would contain mostly non-blood components. The majority or all of the blood could be removed at the beginning of an operation and the body can be perfused with a suspension of the oxygen-filled particles (which may further contain a buffer for the absorption of carbon dioxide, energy substrates such as glucose, and clotting factors such as platelets, FFP and cryoprecipitate) during the operation. Once the bloody portion of the procedure is near the end, the blood could be replaced, and the perfusate of oxygen-filled particles could quickly go away due to absorption of oxygen gas and renal filtration (or mechanical ultrafiltration) of the diluent. When necessary, suspensions containing ~90-95 mL of oxygen gas per dL of suspension may be used given the prolonged time (hours) of providing for the body's entire oxygen consumption.

Cyanotic Congenital Heart Disease

A unique feature of congenital heart disease is partial or complete mixing of saturated and desaturated blood. In perioperative states, systemic desaturation can lead to significant cerebral and myocardial dysfunction. For example, frequently subjects with hypoplastic left heart syndrome require extracorporeal life support in the perioperative period primarily to prevent death due to hypoxemia and the concomitant myocardial dysfunction. ELSO. Extracorporeal Life Support Registry Report, International Summary; 2008 January, 2008.

Particles containing oxygen may be administered intravenously in an effective amount to raise mixed venous oxygen content, systemic arterial oxygen content, and improve myocardial function in subjects in a perioperative states. Thus the particles can be administered in place of a more invasive use of extracorporeal life support device.

Traumatic Brain Injury

Infusion of oxygen-bearing particles into the cerebral circulation may decrease neuronal death at the ischemic penumbra. Given the improved oxygen content of particle suspensions over that of whole blood, subjects with impaired cerebral blood flow, e.g. in traumatic brain injury or intracranial hypertension, directed administration of oxygenated particles into a carotid artery would increase the oxygen content (Ca $O_2$) of blood flow directed to the brain, and may balance the decrease in flow with an improvement in oxygen content.

Treat Pulmonary Hypertension

Perfusion of the venous system, and therefore the pulmonary arteries and arterioles, with 'blood' rich in oxygen, nitric oxide, or other gaseous vasodilators can more effectively relax the pulmonary arterioles (putatively a major contributor to the pathology of pulmonary hypertension). This would be most effective during a pulmonary hypertensive crisis, a potentially fatal event in which high pulmonary pressures cause a decrease in blood flow to the left heart and decreased cardiac output. Accordingly, a venous injection of a suspension containing oxygen-filled particles can quickly reverse the process. This approach could be more effective than delivering oxygen to the lungs via inhalation because of its exposure to the pulmonary arterioles, which are the farthest point in the circulation from the pulmonary capillaries.

Pulmonary Embolus or Hypertension

In near-fatal pulmonary embolus a defect could be created in the atrial septum to permit the flow of venous blood across the atrial septum to allow filling of the left heart (a Rashkind balloon atrial septostomy) from the right heart, bypassing the lungs temporarily. In this setting, a suspension containing oxygen-filled particles can be used to oxygenate blood, thereby permitting time and clinical stability for a surgical thrombectomy, catheter based interventions or medical therapies to be applied to the clot.

Carbon Monoxide Poisoning

Subjects (including patients, soldiers) with severe carbon monoxide poisoning are currently treated with hyperbaric oxygen. This is an expensive and scarce resource, and is impractical for unstable patients due to the technical constraints of the hyperbaric chamber itself. The oxygen-filled particles described herein can be used to create hyperbaric oxygen conditions (i.e. the oxygen content of the blood under hyperbaric conditions is 22-24 mL/dL versus 20 at atmospheric pressure; additionally, pressurized oxygen microparticles could be used to raise the PaO2 of blood to above 700 mmHg). More specifically, use of an oxygen-filled particle suspension containing, for example, 60-80 mL oxygen/dL of suspension, can displace carbon monoxide from hemoglobin and restore normal hemoglobin function as occurs in the hyperbaric chamber. This would obviate the need for a hyperbaric chamber, allow for the cotemporaneous treatment of multiple subjects with carbon monoxide poisoning (e.g. terrorist attacks, house fires, soldiers), the treatment of ICU patients with CO poisoning, and permit the rapid reversal of CO poisoning at or near the point of injury (e.g. at the scene of a fire).

Reduce Injury Caused by Low Systemic Blood Oxygen Saturation

There are many congenital heart lesions in which desaturated blood (from the body) and oxygenated blood (from the lungs) mix in the heart. In some instances, e.g., immediately after a Norwood operation or unrepaired D-transposition of the great arteries, the degree of mixing or the degree of pulmonary blood flow causes the systemic oxygen saturations to be extremely low such that the body develops acidosis and organ injury. In these subjects, raising the oxygen tension of the systemic venous return by even a small amount would raise the systemic oxygen saturations significantly (due to mixing). This would avert a substantial number of subjects who currently are placed on ECMO for even a few days for this reason.

Resuscitation in Obstructed Systemic-Pulmonary Shunts

Several congenital heart lesions (e.g. hypoplastic left heart syndrome) are initially treated with a small tube graft from the innominate artery or the right ventricle to the pulmonary artery. The acute obstruction of these shunts (usually a B-T shunt) causes death within minutes and is an important cause of interstage mortality for these children. The availability to oxygenate the venous blood in these subjects, using the oxygen-filled particles described herein, would allow even a paramedic to effectively resuscitate a subject in need with oxygenated blood. This could also prevent death in a substantial number of hospitalized subjects in hospitals with or without the ability to rapidly place a subject onto ECMO.

Delivery of Oxygen-Filled Particles to Fetuses, Neonates and Infants

The gas filled particles may be administered to a fetus, neonate, or infant in need of additional oxygen. The gas filled particles may be administered to low birth weight infants or premature infants. In one embodiment, the particles filled with oxygen are administered in an effective amount to ensure that the fetus, neonate, or infant is receiving sufficient oxygen, particularly to ensure that the brain of the fetus, neonate or infant receives sufficient oxygen for development and maintenance of normal function.

If a mother is experiencing preeclampsia, the baby must be born. Optionally, the gas filled particles can be administered to the baby, mother, or both in effective amount to deliver an effective amount of oxygen to maintain normal bodily functions when the mother is experiencing preeclampsia.

Neonates with hypoxic ischemic brain injury at the time of birth often suffer from extensive brain injury, manifested as cerebral palsy. This may occur due to even brief periods of hypoxia during the peripartum period. In clinical situations where this is appreciated prior to delivery, such as a nuchal cord or placental abruption, injection of gas filled particles into the umbilical circulation or into the dural space may avert critical hypoxia and may ameliorate some forms of hypoxic ischemic brain injury in this setting.

Newborns with congenital heart disease can have diseases that cause profound cyanosis and organ injury. For example, newborn subjects with D-transposition of the great arteries receive systemic arterial blood flow from the right ventricle, blood flow which is not exposed to the lungs at all. In subjects with inadequate mixing at the atrial level, profound cyanosis can cause organ injury and death. These subjects could be stabilized and transported to definitive care by oxygenating the venous return via infusion of oxygen-filled particles. Subjects with obstructed pulmonary venous return, representing the only true pediatric congenital heart emergency, could be stabilized by creation of an atrial septal defect and oxygenation of venous return as discussed above.

Provide Inotropic Support

Myocardium extracts a higher proportion of oxygen from the blood than any other organs. In post-cardiac bypass or post-myocardial infarction patients (exhibiting tissue edema and mitochondrial dysfunction), a catheter placed into the coronary root may allow delivery of oxygen-filled particles, thereby supersaturating the coronary blood flow and provide a novel route of inotropic support different from all current inotropic methods, all of which rely on the beta receptor. This approach could provide an effective inotropic supplement, especially to those patients with downregulated beta receptors.

Treatment of Intestinal Ischemia

The particles of the invention are also useful for the enteral or periotenal or retroperitoneal administration of oxygen to patients at risk of intestinal ischemia, including but not limited to premature infants at risk for necritizing enterocolitis or adults with mesenteric ischemia.

Calculate Cardiac Output

Cardiac output is defined as the flow rate of blood through the heart and vasculature. It is possible that injection of a small volume of gas could be detected based on a change in oxygen saturation (by injecting oxygen filled particles into the veins of patients with a saturation below 98%, or alternatively, by infusing carbon dioxide, nitrogen or carbon monoxide, or other gas), and detecting the time it took to detect the change by standard pulse oximeter. Alternatively, one could utilize ultrasound to determine the time it took particles to travel from injection to the arterial system. This may be useful as a bedside tool to determine cardiac output, and would be useful even in children with cyanotic congenital heart defects.

Multi-Organ Dysfunction Syndrome

Use of an oxygen-filled particle suspension with high oxygen concentration can be used to achieve extremely high oxygen tensions at the capillary level with or without hemoglobin. This would enhance the uptake of oxygen by dysfunctional mitochondria or through an inflamed endothelium.

Acute Respiratory Distress Syndrome (ARDS)

Refractory hypoxemia is the hallmark of acute lung injury and ARDS. Profound hypoxemia accounts for 10% of the mortality of this common disorder. Meade et al, "Ventilation strategy using low tidal volumes, recruitment maneuvers, and high positive end-expiratory pressure for acute lung injury and acute respiratory distress syndrome: a randomized controlled trial." JAMA, 299(6):637-45 (2008). Particles containing oxygen may be administered intravenously in an effective amount to alleviate the hypoxemia associated with severe intrapulmonary shunting and decrease the mortality and morbidity of ARDS.

Alternatively, nanoparticle or microparticles could be nebulized (with or without pressurization of the gas within it) and administered inhalationally to a patient. The particle may diffuse into pulmonary edema fluid and raise the oxygen tension of the fluid in the alveolar space, causing an increase in systemic oxygenation.

Hemorrhagic Shock

In acute hemorrhage, resuscitative trauma therapy focuses upon restoration of circulating blood volume and oxygen carrying capacity. In states of hypovolemic shock, such as resulting from severe blood loss, the oxygen extraction ratio of peripheral tissues is increased. The result is further desaturation of blood returning to the right heart. Models of blunt chest trauma and hemorrhagic shock have suggested that right ventricular (RV) dysfunction impedes resuscitation efforts.

In late hemorrhagic shock, myocardial ischemia causes impaired contractility. Volume resuscitation of an ischemic, dysfunctional right ventricle may lead to increased RV end-diastolic volume, causing septal shift into the left ventricle (LV), and decreased LV end-diastolic volume.

The oxygen-filled particles can be injected at an appropriate concentration and rate to deliver oxygen directly to the myocardium in a time period ranging from 3 to 10 second following injection. For example, if the oxygen-filled particles contains from 40 to 70 mL oxygen per dL of suspension, the injection of one dL of suspension could deliver approximately 40-70 mL of oxygen directly to the myocardium. Optionally, the oxygen-filled particles may contain a specialized resuscitation fluid, such as synthetic colloid (e.g. Hextend™) or hemoglobin-based oxygen carrier (HBOC) as the carrier.

Neurological Disease

Further contemplated is a method of delivering a gas to the brain of a subject suffering from a neurological disease. The subject may be delivered a neuroprotective gas such as a noble gas, e.g. argon. The particles may be designed to deliver the gas to the blood which will be delivered to the area of the brain. The gas can then pass through the blood brain barrier. Alternatively or additionally the particles may be designed such that they will cross the blood brain barrier. For instance the particles may be nanometer sized.

Organs

The particle of the invention may be delivered topically to a variety of organs including skin and internal organs.

Additional Therapeutic Methods Contemplated

Further contemplated is a method of delivering a gas to an organ of a subject, comprising topically administering to the organ of the subject a pharmaceutical composition comprising a gas-filled particle, wherein the pharmaceutical composition is topically administered directly to the organ. In certain embodiments, the organ is skin and a skin disorder or wound is treated. In certain embodiments, the wound is a burn. Further contemplated is a method of delivering a gas to a subject having a neurological disease, comprising administering to the subject a pharmaceutical composition comprising a gas-filled particle in an effective amount to deliver the gas to the brain of the subject. In certain embodiments, the gas filled particles have an average particle size of less than one micron. In certain embodiments, the gas is a noble gas such as argon.

Delivery of a gas other than oxygen can confer various therapeutic benefits. For example, isoflorane-filled particles can be delivered to a subject having or suspected of having asthma for treating the disease. In another example, particles filled with an insoluble gas (e.g., nitrogen or a noble gas) can be used as a volume expander. Particularly, particles having a size of 1-5 microns do not pass through gap junctions and thereby serve as an excellent volume expander. Moreover, gaseous sedatives can be delivered via gas-filled particles to achieve a quick effect.

In addition to therapeutic applications, gas-filled particles can also be used for non-therapeutic purposes, e.g., as MRI contrast agents, fuel additives, or research tools for defining the volume of oxygen exposed to an environment.

In addition to stabilizing the particles, it is possible that this technique may extend the utility of these particles to having alternative uses. Specifically, particles which persist in the bloodstream following oxygen transfer may be useful as dual purpose agents in trauma resuscitation. They may be useful as a volume expander in military applications because they are lightweight and, if properly designed, can be manufactured not to be able to leave the bloodstream and into the interstitial space following injection.

Non-Medical Uses of Oxygen-Filled Particles

Oxygen filled particles could be used to enhance the oxygen tension and oxygen content of fossil fuels, and improve the efficiency of combustion processes. This may enhance fuel economy, and be used to make any such process more efficient, powerful and/or cost-effective.

Administration

The compositions containing particle suspensions may be administered locally or systemically, depending on the condition to be treated. The compositions are typically administered via injection. In some embodiments the compositions can be administered as continuous infusions. In some embodiments the compositions are administered intravenously, intraosseously, or intraarterially. In others, the compositions are administered directly to the tissue or organ in need of treatment. In other embodiments the particles can be administered inhalationally, topically (to the pleural or peritoneal cavity, to the skin, to a burn, to a wound, to the fascia, to the muscles, to the intestines or other organs), enterally (orally, sublingually, enterally, rectally).

In certain embodiments, the pharmaceutical composition is administered to the subject by intravenous, intramuscular, intraosseous, or intraarterial injection. In certain embodiments, the pharmaceutical composition is administered to the subject topically, orally, enterally, sublingually, intranasally, or by inhalation. In certain embodiments, topical delivery is delivery to pleural, skin, peritoneum, or facia.

In one embodiment, the particle suspensions are stable in storage for prolonged periods of time, and may be withdrawn and directly injected without further alterations of the solution.

In another embodiment, the particles may be stored as a powder and reconstituted at the point of use with a pharmaceutical compound.

In another embodiment, the particles may be stored as a powder and applied topically to enterally as a powder or as viscous slurry.

In another embodiment, the particles may be formed just prior to administration, e.g. within seconds or minutes of injection, by a suitable device. The methods disclosed herein allow for rapid production of oxygen-containing particles for use in clinical settings or in the field.

The volume of the gas-filled particle suspension to be administered is a function of a number of factors including, the method of administration, the gas percentage of the particle suspension, and the age, sex, weight, oxygen or carbon dioxide tension, blood pressure, systemic venous return, pulmonary vascular resistance, and physical condition of the patient to be treated.

The whole body oxygen consumption of an adult at rest is approximately 200 mL oxygen per minute. Thus, in the setting of an acute airway obstruction, for example, infusion of 200 mL/minute of oxygen would prevent critical ischemic injury. For example, particle suspensions containing 70 mL/dL of suspension can be administered at 285 mL/minute to transfer 200 mL/minute of oxygen in vivo. Since most of the suspension contains oxygen gas, most of the volume decreases following administration and release of the gas. Additionally, when used in the setting of an acute resuscitation or in organ-targeted oxygen delivery, volumes of co-infusate may be much lower, For example, a 10 mL bolus of 50% (volume gas/volume suspension) particles in adults may provide a suitable amount of oxygen to improve the survival of the organ.

In another example, to administer 200 mL/min of oxygen gas, an emulsion containing 70 volume % gas at 10 ATM would be infused at 28.5 mL/min to deliver 8.5 mL/min of aqueous phase and 20 mL/min of gas phase at 10 ATM, or 200 mL/min of aqueous phase. For the same emulsion at 70 vol % and 20 ATM, the volume of the aqueous phase to be infused would be 4.2 mL/min, which would still provide 200 mL/min of oxygen gas at STP.

The particles are preferably designed to release the gas encapsulated therein quickly following administration in vivo. Typical release times range from 0.5 seconds to 1 minute, with shorter time periods, such as from 0.5 to 30 seconds, more preferably from 0.5 to 10 seconds, being preferred for acute resuscitations and resuscitations of the heart and with longer time periods being preferred for delivery of oxygen to the brain.

In some embodiments, the particles are designed to persist in vivo until they reach hypoxic tissue, at which time they will release the encapsulated oxygen and the particle with collapse. The particle does not persist in vivo for a sufficient time to carry carbon dioxide or other gases to the lungs. The particles generally release the encapsulated gas and the gas is absorbed by hemoglobin prior to the first circulation into the pulmonary vasculature. In a healthy adult subject with a normal cardiac output, the release of the encapsulated gas typically occurs from 4 to 5 seconds following injection, or faster.

The suspension is delivered into a subject at a suitable flow rate depending upon the subject's need. For example, when the subject needs oxygen supply, a suspension containing oxygen-filled particles can be delivered to that subject at a flow rate of 10 mL/min up to 400 mL/min (e.g., 50-300 mL/min or 100-200 mL/min). The flow-rate can also be adjusted based on the subject's oxygen consumption, oxygen saturation, skin and mucous membrane color, age, sex, weight, oxygen or carbon dioxide tension, blood pressure, systemic venous return, pulmonary vascular resistance, and/or physical conditions of the patient to be treated.

Methods of Preparation

The gas-filled particles described herein can be prepared by any conventional methods, including shear homogenization (see Dressaire et al., *Science* 320(5880):1198-1201, 2008), sonication (see Suslick et al., *Philosophical Transactions of the Royal Society of London Series a-Mathematical Physical and Engineering Sciences* 357(1751):335-353, 1999; Unger et al., *Investigative Radiology*, 33(12):886-892, 1998; and Zhao et al., *Ultrasound in Medicine and Biology*, 31(9):1237-1243, 2005), extrusion (see Meure et al., *AAPS PharmSciTech,* 9(3):798-809, 2008), spraying (see Pancholi et al., *J. Drug Target.* 16(6):494-501, 2008), mixing such as double emulsions (see Kaya et al., *Ultrasound in Medicine and Biology.* 35(10):1748-1755, 2009), hot melt encapsulation, and drying (e.g., by spray drying, and/or lyophilization) to obtain particles for administration. See also Meure et al.,

*AAPS PharmSciTech* 9(3):798-809, 2008. The process of "spray drying" refers to a process wherein a solution is atomized to form a fine mist and dried by direct contact with hot carrier gases. In the case of crosslinking the stabilized membrane and/or sheath membrane, additional steps are required for crosslinking. One preferred method of spray drying includes a 3-fluid nozzle.

For example, a process for preparing gas-filled particles includes at least two steps: (i) mixing one or more materials as described above in a medium (e.g., an organic solvent, an aqueous solution, a medium comprising a viscosity enhancing agent, or mixture thereof) to form a pre-suspension, and (ii) dispersing one or more gases into the pre-suspension to form gas-filled particles via, e.g., adsorption to the gas/lipid interface of entrained gas bodies. See, e.g., U.S. Pat. No. 7,105,151. Step (ii) can be performed under high energy conditions, e.g., intense shaking, high shear homogenization, or sonication. See, e.g., US 2009/0191244 and Swanson et al., Langmuir, 26(20):15726-15729, 2010. Acoustic emulsification (i.e. sonication) may be used to agitate the precursor solution and form the particles. Sonication generates particles rapidly and reproducibly within just a few seconds. In sonication, the sonicator horn is typically placed at the suspension-gas interface. The precursor suspension is sonicated for a sufficient time period at a sufficient power to produce the particles. Particles created in this way follow a heterogeneous size distribution. The largest particles are the most buoyant and rise to the top of the suspension, while less buoyant, smaller particles remain motile in the sonicated suspension. This allows for separation based on different migration rates in a gravitational field. In certain embodiments, high energy conditions are by high shear homogenization or sonication. The steps may further comprise crosslinking or polymerization to provide the desired particle.

For example, in one aspect, provided is a method of preparing a particle encapsulating a gas, the method comprising:
(i) mixing one or more materials in a medium to form a pre-suspension; and
(ii) dispersing one or more gases into the pre-suspension to form gas-filled particles comprising a stabilized membrane in order to provide a stabilized membrane.

In this particular aspect, the one or more materials comprise a stabilizing agent.

In another aspect, provided is a method of preparing a particle encapsulating a gas, the method comprising:
(i) mixing one or more materials in a medium to form a pre-suspension, wherein at least one material comprises a covalent or non-covalent crosslinkable group;
(ii) dispersing one or more gases into the pre-suspension to form gas-filled particles comprising a stabilized membrane; and
(iii) subjecting the gas-filled particle to polymerization or crosslinking conditions in order to provide a covalent or non-covalent crosslinked stabilized membrane.

In this particular aspect, the one or more materials does not necessarily comprise a stabilizing agent.

In another aspect, provided is a method of preparing a particle encapsulating a gas, the method comprising:
(i) mixing one or more materials in a medium to form a pre-suspension;
(ii) dispersing one or more gases into the pre-suspension to form gas-filled particles comprising a stabilized membrane; and
(iii) contacting the gas-filled particle with a material which comprises a covalent or non-covalent crosslinkable group, wherein the material encapsulates the membrane as a covalent or non-covalent crosslinked sheath membrane upon subjecting the mixture to polymerization or crosslinking conditions.

In this particular aspect, the one or more materials does not necessarily comprise a stabilizing agent.

One method for making the particles is a double emulsion method, i.e. water-oil-water. For example a polymer may be dissolved in oil which is mixed with water to form droplets. The droplets are added to water to form empty membranes or honeycomb structures. Thus, in some instances the hollow particles of the invention are spherically shaped or honeycomb structures. The particle size, thickness of the membrane and honeycomb or spherical nature of the particles can be adjusted by manipulating the parameters of the methods of the invention. For instance, particle size can be altered by manipulation of homogenization parameters. Thickness of the membrane can be altered by adjusting viscosity, osmotic gradient and/or precipitation speed. Detailed examples for manipulating these and other parameters to fine tune the preparation of the particles to achieve different properties are set forth in the examples below.

One method for making the particles is a double emulsion method, i.e. water-oil-water. For example a polymer may be dissolved in oil which is mixed with water to form droplets. The droplets are added to water to form empty membranes or honeycomb structures. Thus, in some instances the hollow particles of the invention are spherically shaped or honeycomb structures. The particle size, thickness of the membrane and honeycomb or spherical nature of the particles can be adjusted by manipulating the parameters of the methods of the invention. For instance, particle size can be altered by manipulation of homogenization parameters. Thickness of the membrane can be altered by adjusting viscosity, osmotic gradient and/or precipitation speed. Detailed examples for manipulating these and other parameters to fine tune the preparation of the particles to achieve different properties are set forth in the examples below.

In certain embodiments, the method may comprise a crosslinked membrane encapsulated by a crosslinked shell, i.e., by subjecting the gas-filled particle to polymerization or covalent or non-covalent crosslinking conditions in order to provide a covalent or non-covalent crosslinked stabilized membrane, and then contacting this gas-filled particle with another material, which upon subjecting the mixture to polymerization or covalent or non-covalent crosslinking conditions, encapsulates the membrane as a covalent or non-covalent crosslinked membrane. Alternatively, the shell is crosslinked, but not the membrane. Alternatively, the membrane is crosslinked, but not the shell.

The particles thus produced, suspended in the medium used in step (i), can be concentrated, dried (e.g., lyophilized, spray dried), and/or subjected to size selection by methods known in the art, such as differential centrifugation as described in US 2009/0191244 to produce dried particles or highly concentrated suspensions of particles. Dried particles, stored as a powder, may be a way to achieve longer shelf life, and can be reconstituted by addition of a medium, such as an organic solvent, an aqueous solution, a medium comprising a viscosity enhancing agent, or mixture thereof.

In certain embodiments, the gas of the particle is replaced with another gas, e.g., by applying a stream of the desired gas to, or pulling a vacuum on, the particle to remove the encapsulated gas, then filling the hollow particle with the desired gas.

As understood from the present disclosure, the particles may be also prepared in a medium (e.g., an aqueous medium) comprising one or more viscosity enhancing agents. The inventors contemplate preparing particles in such a medium stabilizes the particle by decreasing the particle size and/or by preventing the particle from interacting with neighboring particles.

Particles and suspensions may be further be stored under inert conditions (e.g., under a blanket of argon) or under a blanket of another gas as describe herein (e.g., oxygen, carbon dioxide, carbon monoxide, nitrogen, nitric oxide, nitrous oxide, an inhalational anesthetic, hydrogen sulfide, helium, or xenon, or a mixture thereof). In certain embodiments, the particles or suspensions are stored in an oxygen-tight container, optionally under high gas pressure. Exemplary pressurization techniques for making gas filled particles under high pressure are described in U.S. Pat. No. 4,344,787, incorporated herein by reference. In certain embodiments, the gas is at 1 atmosphere, and is not pressurized. In certain embodiments, the gas is pressurized to greater than 1 atmosphere, e.g., between about 2 to about 25 atmospheres. In certain embodiments, the gas is pressurized at greater than 1 atmosphere and is delivered at an infusion rate of up to 10 ml per minute to the subject. Alternatively, in certain embodiments, the gas is not pressurized and is delivered at an infusion rate of up to 400 ml per minute to the subject.

Optionally, in another aspect, the invention relates to methods of preparing hollow particles filled with gas. The particles may be formed, for instance around a core component, to create a hollow structure, wherein the core component is removed to form a hollow particle.

Exemplary methods of making hollow particles are described in U.S. Pat. Nos. 3,528,809, 3,674,461, 3,954,678, 4,059,423, 4,111,713, 4,279,632, 4,303,431, 4,303,603, 4,303,732, 4,303,736, 4,344,787, 4,671,909, 8,361,611, 7,730,746, EP1311376, U.S. Pat. Nos. 6,720,007, 3,975,194, 4,133,854, 5,611,344, 5,837,221, 5,853,698, each of which is incorporated herein by reference. The inventors of the present invention contemplate any of the materials as heretofore described may be used to make such hollow particles, and specifically contemplate hollow particles made from PGLA.

For example, in one aspect, provided is a method of preparing a particle encapsulating a core component, the method comprising mixing one or more materials with a core component to form a pre-suspension comprising particles encapsulating the core component around a stabilized membrane.

As is understood herein, the core component may be a volatile component or core. A volatile component or core refers to a material that can be removed from the dried particle to produce a hollow center, by for instance freeze drying. Exemplary volatile components include, but are not limited to, inorganics such as ammonia and its corresponding volatile salts (e.g., ammonium bicarbonate, ammonium acetate, ammonium chloride, ammonium benzoate, ammomium carbonate) and water. Exemplary non-volatile components which can also be included, are salts, buffers, acids, bases, and the like, which upon removal of the volatile component are left as a residue on or in the hollow particle.

The volatile component may further be considered a pore forming agent. Pore forming agents can be included, for example, in an amount of between 0.01% and 75% weight to volume, to increase pore formation. For example, in solvent evaporation, a pore forming agent such as a volatile salt, for example, ammonium carbonate, ammonium bicarbonate, ammonium acetate, ammonium chloride, or ammonium benzoate or other lyophilizable salt, is first dissolved in a medium such as water. The solution containing the pore forming agent is then emulsified with the solution to create droplets of the pore forming agent in the material. After the particle is formed by any of the method described herein, the suspension of particles may be spray dried or taken through a solvent evaporation/extraction process.

Solvent evaporation is described by E. Mathiowitz, et al., J. Scanning Microscopy, 4, 329 (1990); L. R. Beck, et al., Fertil. Steril., 31, 545 (1979); and S. Benita, et al., J. Pharm. Sci., 73, 1721 (1984), the teachings of which are incorporated herein. In an exemplary solvent evaporation method using a pore forming agent, a material is dissolved in a volatile organic solvent such as methylene chloride. A pore forming agent as a solid or in an aqueous solution may be added to the solution. The mixture is sonicated or homogenised and the resulting dispersion or emulsion is added to an aqueous solution that contains a surface active agent such as TWEEN20, TWEEN80, PEG or poly(vinyl alcohol) and homogenised to form an emulsion. The resulting emulsion is stirred until most of the organic solvent evaporates, leaving microspheres.

Hot-melt microencapsulation is described by E. Mathiowitz, et al., Reactive Polymers., 6, 275 (1987), the teachings of which are incorporated herein. In an exemplary hot-melt microencapsulation method using a pore forming agent, the material is first melted and then mixed with the solid particles of the pore forming agent. The mixture is suspended in a non-miscible solvent (like silicon oil), and, while stirring continuously, heated to 5 C above the melting point of the material. Once the emulsion is stabilized, it is cooled until the particles solidify. The resulting particles are washed by decantation with a polymer non-solvent such as petroleum ether to give a free-flowing powder.

In an exemplary spray drying method using a pore forming agent, microparticles can be produced by spray drying by dissolving a material in an appropriate solvent, dispersing a pore forming agent into the solution, and then spray drying the solution to form particles. Using spray drying apparatus available in the art, the polymer solution may be delivered through the inlet port of the spray drier, passed through a tube within the drier and then atomized through the outlet port. The temperature may be varied depending on the gas or material used. The temperature of the inlet and outlet ports can be controlled to produce the desired products. The size of the particulates is a function of the nozzle used to spray the solution, nozzle pressure, the flow rate, the material used, the material concentration, the type of solvent and the temperature of spraying (both inlet and outlet temperature) and the molecular weight. Generally, the higher the molecular weight, the larger the capsule size, assuming the concentration is the same. Typical process parameters for spray drying are as follows: concentration of the material in the medium=0.005-0.10 g/ml, inlet temperature=30°-200° C., outlet temperature=20°-100° C., flow rate=5-200 ml/min., and nozzle diameter=0.2-4 mm ID. Particles ranging in diameter between one and ten microns can be obtained with a morphology which depends on the selection of the material, concentration, molecular weight and spray flow.

The particles may be made by a method using an aqueous core that is then freeze dried to yield the final hollow particle. For example this may be accomplished using a 3-fluid nozzle in a spray drying method. See also US 2011/021280, incorporated herein by reference, which describes spray drying using a 3-fluid nozzle.

Upon formation of the particle, the core component of the medium is removed, e.g., in vacuo and/or by drying, e.g., by lyophilization and/or by spray drying, to provide a hollow, dried particle. Such a hollow dried particle may later be reconstituted by addition of another medium, such as an organic solvent, an aqueous solution, a medium comprising a viscosity enhancing agent, or mixture thereof. Such a particle may later be filled with a gas.

For example, in one specific aspect, provided is a method of preparing a gas-filled particle comprising drying a particle comprising a core component to produce a hollow dried particle and dispersing one or more gases into the hollow dried particle to form a gas-filled particle, wherein the one or more gases is not a fluorinated gas, perfluorocarbon based liquid, or hemoglobin. In certain embodiments, the drying step is spray drying. In certain embodiments, the core component comprises ammonium carbonate. In certain embodiments, the core component comprises water. In certain embodiments, the method further comprises pressurizing the gas.

EXEMPLIFICATION

In order that the invention described herein may be more fully understood, the following examples are set forth. The examples described in this application are offered to illustrate the compounds, pharmaceutical compositions, and methods provided herein and are not to be construed in any way as limiting their scope.

In prior work, an experiment was conducted wherein human blood was placed in a beaker and desaturated to an $SO_2$ of 65% using nitrogen and carbon dioxide. Temperature was set at 37 C and pH was between 7.25 and 7.45. Following a quantification of hemoglobin, the amount of oxygen gas needed to increase the oxyhemoglobin saturation to 100% was calculated, and translated into a volume of OMPs. This quantity of OMP was added to the blood sample, and oxyhemoglobin saturation was continuously measured using a spectrophotometric oximeter probe. All of the top 5 OMPs transferred their entire oxygen payload to blood within 5 seconds of contact.

Sprague Dawley rats (weight range 315-380 grams) were then anesthetized using inhalational Isoflurane and then systemically heparinized. Following adequate anesthesia, the heart was excised and cannulated within 3 minutes for perfusion with modified, oxygenated Krebs-Hensylate buffer (KHB) in a constant pressure perfusion system (P=85 mmHg). A left ventricular vent was placed, followed by a left ventricular pressure balloon. Hearts were then treated according to one of three treatment groups (n=6 hearts per group). All perfusates were passed through a 5 micron filter: (1) Positive controls were perfused with oxygenated ($PO_2$>650 mmHg, $PCO_2$ 20 mmHg) KHB for a 30 minute stabilization period followed by a 30 minute observation period; (2) Negative controls were perfused with de-oxygenated KHB ($PO_2$ 5-10 mmHg, $PCO_2$ 20 mmHg) for the stabilization and observation periods; and (3) Experimental animals were perfused with KHB that had been deoxygenated to $PO_2$ of <5 mmHg, then treated with OMPs. The $PO_2$ of the perfusate in this group was approximately 300-400 mmHg.

During the observation phase, the following endpoints were measured: heart rate, pulse pressure, left ventricular systolic pressure and rate of systolic and diastolic acceleration (dP/dT and -dP/dT, markers of systolic and diastolic performance, respectively). Finally, hearts were snap-frozen for quantification of ATP and preserved using ETC buffer for observation of endothelial health. Left ventricular systolic pressure (LVSP), pulse pressure, heart rate, and positive and negative myocardial acceleration were found similar between normoxic and LOM-treated hearts, and were significantly improved compared to hypoxic hearts. Further, coronary vascular resistance was similar in OMP-treated and positive control groups, suggesting that OMPs are able to directly deliver oxygen to myocardium without causing microvascular obstruction.

Snap frozen tissues were preserved using a Wollenburger clamp, followed by immediate immersion in liquid nitrogen. Samples were stored at -80 C until assessment of ATP levels by HPLC. ATP levels in hypoxic hearts were significantly lower compared to either OMP-treated or positive control hearts. No differences in ATP levels between OMP-treated and positive control hearts were found. Together, the results of these experiments are very encouraging in several respects: (1) the emulsion was filtered, (2) OMP-treated hearts did not exhibit any decrement in coronary flow rate in a constant pressure perfusion system, indicating that coronary vascular resistance was not negatively impacted, and (3) OMPs appear to diffuse oxygen to surrounding fluid efficiently (such as human plasma), permitting transfer of oxygen directly to tissues in an asanguinous environment.

With these data, the efficacy of these OMPs to prolong life in a lethal model of hemorrhagic shock was tested. 9 animal experiments in this study were completed. The first 5 animals were control animals, in which the capacity to anesthetize and instrument the animals, record the data in real time, and fine-tuned the lethality of the procedure was demonstrated. Instrumentation included placement of a tracheal tube, central arterial and venous lines, and placement of a pulmonary arterial catheter with the capacity to follow continuous cardiac output measurements. Following baseline observations, animals hemorrhaged at 100 mL/minute until the mean arterial blood pressure was 35 mmHg, followed by a 10 minute observation period. Thereafter, the tracheal tube was clamped and the animals were paralyzed, emulating the hypoxic injury which commonly occurs on the battlefield following severe chest trauma. The three animals treated in this way all exhibited a loss of circulation within 5 minutes of the onset of hypoxia.

Pilot experiments were conducted next including the treatment of hypoxic, hemorrhaging swine using OMPs in this same model. The endpoints measured were to include survival time (ideally, extending 5 minutes to 1 hour of survival time), arterial oxyhemoglobin saturations and arterial pH and lactate levels. Four swine were treated by hand injections of 100 mL aliquots of LOMs per minute, finding that the pulmonary artery saturation, the arterial saturations both increased to the 80 s from a baseline of 50 s. Unfortunately, however, none of the four swine exhibited a survival longer than 5 minutes (not statistically different than controls) despite a resolution of hypoxemia. Additionally, necropsy of all of the animals demonstrated a distended pulmonary artery (pulmonary artery pressures never increased above normal, although the animals were quite hypotensive during the injections), an empty left atrium, and evidence of free gas within the inferior vena cava. Importantly, this phenomenon had never been noted in prior experiments in which OMPs were infused at significantly lower infusion rates and using a syringe pump instead of hand injections.

Although OMPs which are composed of self-assembling phospholipids are able to be manufactured in bulk easily, are reasonably stable in storage over time, and exhibit a favorable oxygen release profile, they are more susceptible to degradation under high shear conditions than stabilized particles. Following a pressure injection through a catheter, for example, they may break down and release free gas into the vasculature.

The invention involves in some aspects the manufacture of gas-filled particles which are stabilizing using one of many approaches: (a) microparticles stabilized by a coating, with or without crosslinking of the coating, (b) microparticles stabilized by internal crosslinked shell ("stabilized membrane"), (c) particles stabilized in a viscous medium (in the presence of a viscosity enhancing agent), and (d) polymer-based microparticles.

Example 1

Microparticles Stabilized by an Alginate Membrane

A particle comprising ionically crosslinked membrane of alginate surrounding a stabilized membrane comprising lipidic material was developed.

To prepare alginate-lipid precursor, 0.5 g of alginic acid to 100 mL of 1×PBS stirring at 600 rpm on stir plate. The solution was then agitate for 30 seconds at 4,000 rpm using a high-shear mixer (Silverson L5MA). 2.0 g 1,2-Distearoyl-sn-glycero-3-phosphocholine (DSPC) and 1.0 g cholesterol were added to the alginate-PBS.

The lipid-alginate precursor was transferred to a 140 mL plastic syringe used as a holding container to create a low volume production system. The air-tight syringe was then purged with oxygen gas. Using an infusion pump (2 LPM), the emulsion was infused into the Silverson Verso which mixed the emulsion at 7,500 rpm with 0.25 LPM oxygen gas. The process was continued for 10 minutes. In this experiment, no OMPs were formed, and large amounts of gas were trapped in the circulating fluid (visible in clear tubing of mini-verso system), but not encapsulated. Gentle shaking of the 140 mL syringe popped all the particles and no net volume increase was noted.

It was hypothesized that there was insufficient alginate to create a coating, and therefore increased the percentage of alginate from 0.005 weight % to 1 weight %. Additionally, it was hypothesized that alginate interfered with the self-assembly of the OMPs. Therefore, the OMPs were manufactured prior to the addition of alginate.

For this experiment, particles from 1,2-distearoyl-sn-glycero-3-phosphocholine (DSPC) and cholesterol (1:1 mol ratio) by using an inline homogenizer, followed by concentration by centrifugation, and dilution with plasma-lyte were manufactured. 50 mL aliquots of concentrated particles were placed into 140 mL syringes and added various volumes of 1% alginate solution to each. The emulsion was hand-mixed via gentle inversions for 10 minutes, then centrifuged for 10 min at 1,000 rpm. This resulted in intact particles which were then attempted to crosslink through the addition of 40 mL of 1M $CaCl_2$ to each syringe and shook vigorously. The emulsions were centrifuged for 10 min at 1,000 rpm and collected final cakes in glass test tubes.

Figure 2:
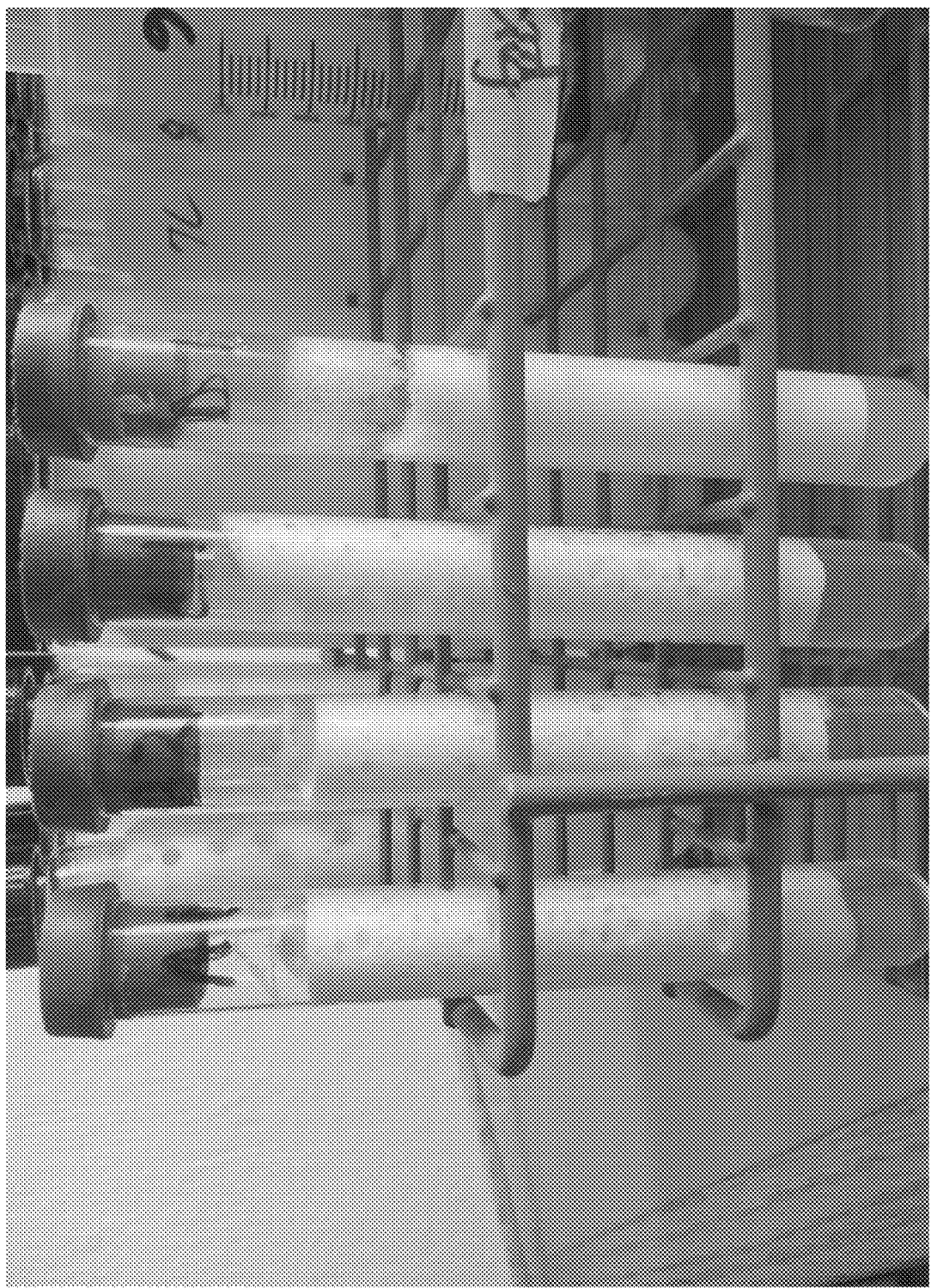
FIG. 2 depicts DSPC/cholesterol particles with alginate membrane at a 1:1 ratio (Tube A), a 2:1 ratio (Tube B), and a 10:1 ratio (Tube C). Tube D contains particles formed using DSPC and cholesterol in a 1:1 ratio alone, without alginate.

FIG. 2 depicts DSPC/cholesterol OMPS concentrate and sodium alginate OMPs in a 1:1 ratio (Tube A), a 2:1 ratio (Tube B), and a 10:1 ratio (Tube C). Tube A was mixed with the highest concentration of sodium alginate. Tube D is the OMPs using DSPC and cholesterol in a 1:1 ratio alone, without sodium alginate. As shown in FIG. 2, after 2 weeks in storage at room temperature, Tube D lost substantial volume and significant amounts of lipid, as indicated by the turbid fluid at the bottom of the test tube. Tube A had the lowest amount of lost microparticles.

A=50 mL cake/50 mL alginate solution→40 mL $CaCl_2$ solution; B=50 mL cake/25 mL alginate solution→40 mL $CaCl_2$ solution; C=50 mL cake/5 mL alginate solution→40 mL $CaCl_2$ solution.

Figure 3:
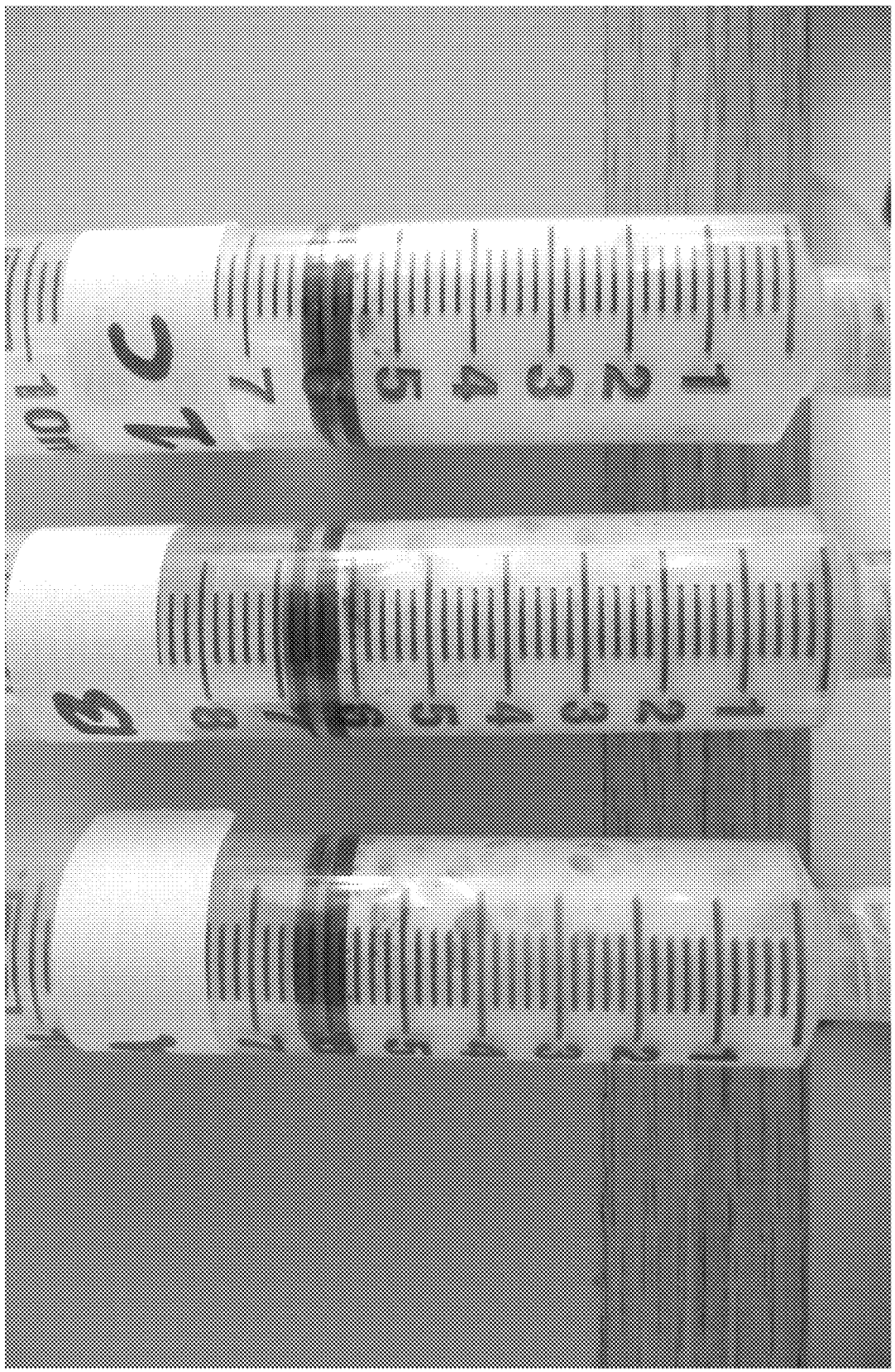
FIG. 3 depicts DSPC/cholesterol particles with alginate membrane at 1:1 ratio (Tube A), 2:1 ratio (Tube B), and a 10:1 ratio (Tube C) following 5 months of storage at room temperature.

Although there was some loss of particles following the sequential additions of alginate and again with addition of $CaCl_2$ solution, the process resulted in intact particle emulsions which could be observed over time. Therefore, as a screening test, 10 mL aliquots of each emulsion (A-C as above) for a 5 month period were observed. See FIGS. 2 and 3. As shown in FIG. 3, all three emulsions experienced some product loss (30-40%) over the 5 month period at room temperature. However, these results represent an improvement in shelf stability over non-stabilized lipids.

Example 2

Microparticles Stabilized by a Poly(Allylamine) (PAH) Membrane

Poly(allylamine) hydrochloride (PAH), a cationic polyelectropolye has been used to create carbon nanotubes and porphyrin under mildly acidic conditions. See, e.g., Andrade et al., *ChemPhysChem* 13, 3622-3631 (2012). Addition of PAH significantly increased the lifetime of microbubbles (on the order of hours, however) without affecting size distribution. A layer-by-layer (LbL) approach for adding polyectrolytes may electrostatically stabilize microbubbles. DSPC, may attract PAH, a cationic polyectrolyte. See, e.g., Howard et al., *International Journal of Molecular Sciences* 11, 754-761 (2010).

A 90 mL suspension containing 2 g DSPC and 1 g cholesterol and $H_2O$ was prepared and run in the mini verso system (140 mL syringe vessel, 7,500 rpm, 1.35 LPM roller pump, 0.5 LPM oxygen headspace and inflow, 4 C water bath). After 1 minute a solution of PAH and $H_2O$ (0.335 mL PAH, 10 mL H2O) was injected into the 140 mL syringe. Contents were mixed in verso for additional time and centrifuged at 500 g for 1 minute, then imaged at 40×.

Figure 4:
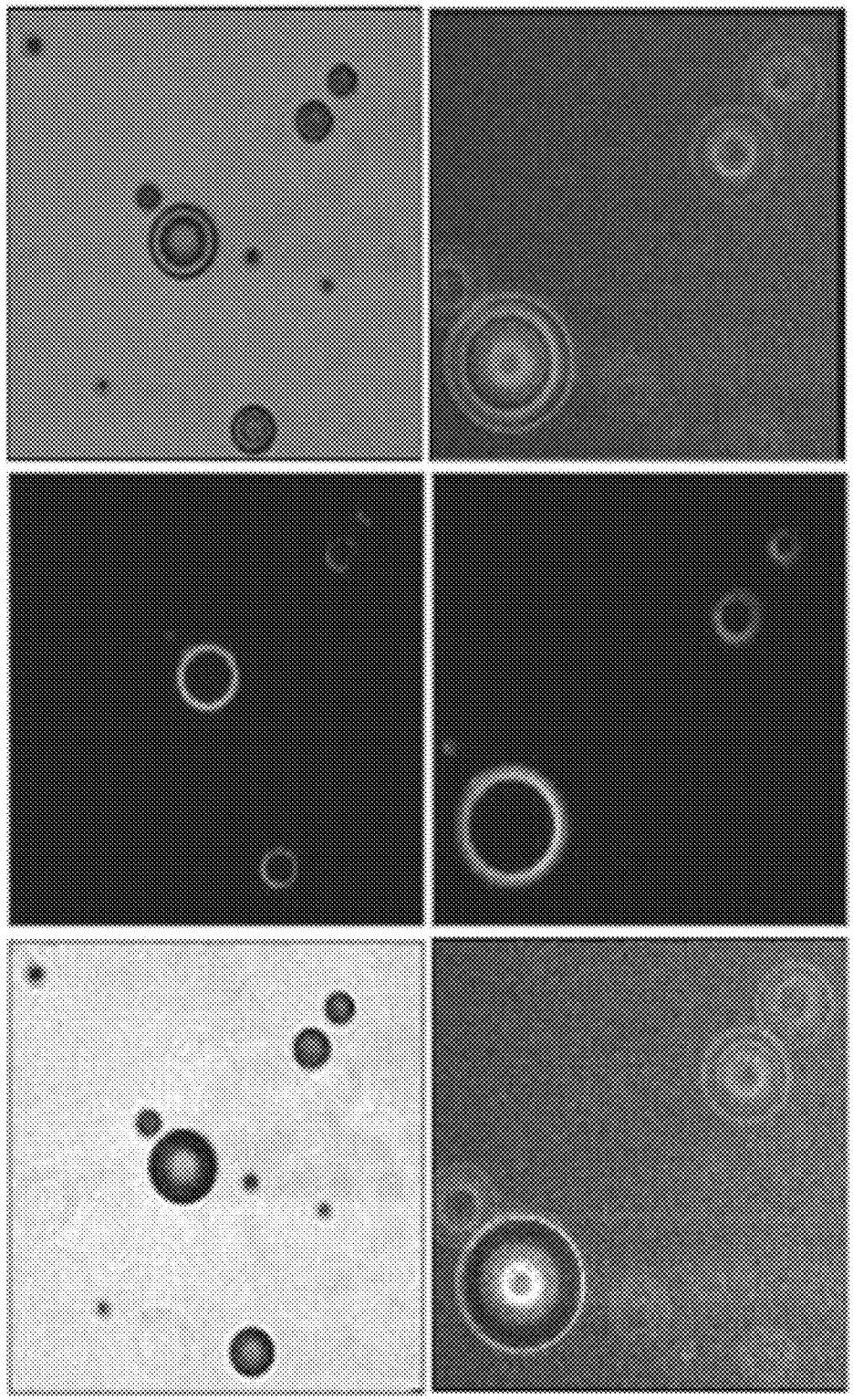
FIG. 4 depicts p articles composed of DSPC and cholesterol coated with poly(allylamine) hydrochloride (PAH). Panels to the right show fluorescently labeled PAH coating the DPSC monolayer.

The emulsion appeared to have large particles/foam before centrifuging, but resulted in a clean 'cake' following centrifugation. As shown in FIG. 4, particles were ~5 microns in diameter and were clearly coated by the fluorescently labeled PAH.

Example 3

Microparticles Stabilized by Internal Crosslinking of Triple Bonds within the Stabilized Membrane Acetylenes contain triple bonds that can polymerize under the influence of heat or UV-light irradiation. Polymers containing diacetylenes undergo 1,4-addition of the conjugated triple bonds within the main chain forming stable chains with low water-adsorption and good adhesion. Polydiacetylene lipids are also biocompatible and elastic, both of which are tremendously beneficial for the purposes of intravenous oxygen delivery. Varying mole fractions of diacetylene or UV exposure time can fine tune surface properties.

The following samples were prepared within scintillation vials: (1) 11.8 mg acetylene, 1.18 mL pure $H_2O$, (2) 6.7 mg acetylene, 5.5 mg diacetylene with 1.22 mL pure $H_2O$ and (3) 10.7 mg diacetylene and 1.07 mL pure $H_2O$. In a low-light environment, each vial was sonicated at the air-liquid interface for 30 seconds at maximal power.

The resulting solutions were crosslinked as follows: nitrogen was bubbled into the scintillation vial a 1 LPM for 5 minutes, then placed under an enclosed 254 nm UV lamp for 1 hour. The crosslinked solution was subsequently sonicated to break up aggregates.

In order to determine the stability of the particles (and to confirm that they were crosslinked), formed particle emulsions were divided into two groups: one sample was exposed to a detergent known to intercalate into lipid interfaces (Triton X, Sigma Aldrich), and another left as a control. When this detergent was added to non-crosslinked DSPC/cholesterol OMPs, for example, they were all destroyed within minutes.

Figure 5B:
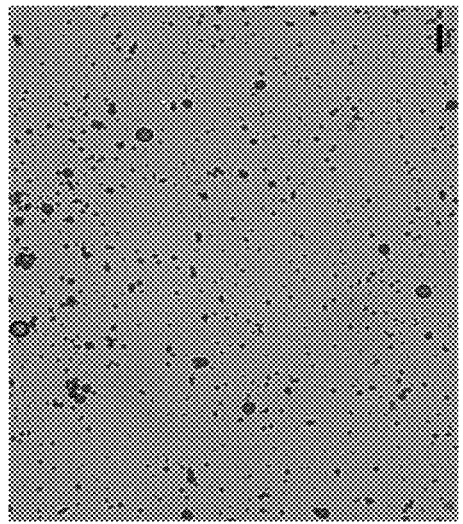
FIGS. 5A-5D depict depicts particles composed of UV light-crosslinked diacetylene (purchased from Avanti Lipids). There is a purple hue observable in the crosslinked solution (FIG. 5A), and the polydisperse size distribution without aggregation (FIG. 5B). There was no difference in number of particles prior to (FIG. 5C) and following (FIG. 5D, bottom) prolonged exposure to a detergent known to break down uncrosslinked lipid microparticles. Scale bars, 10 microns.
Figure 5D:
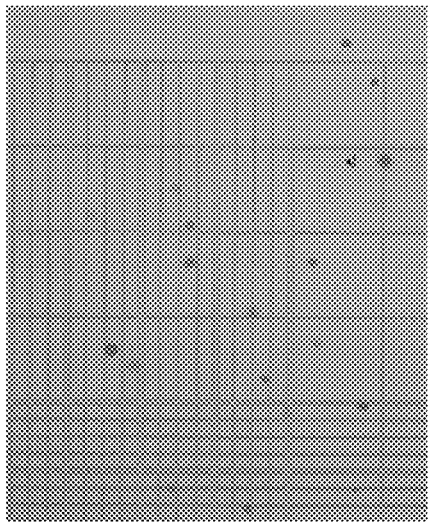
Figure 5A:
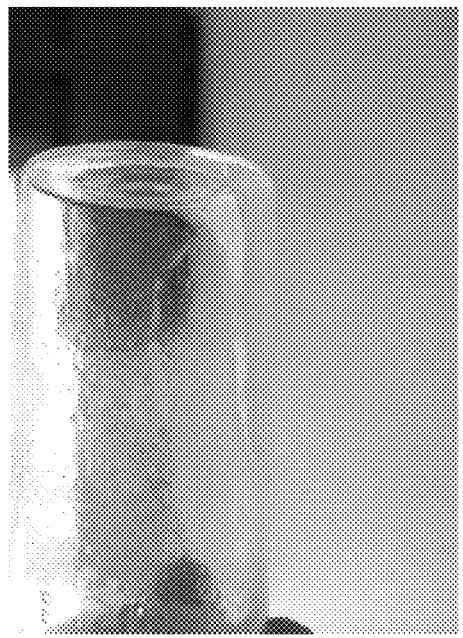
Figure 5C:
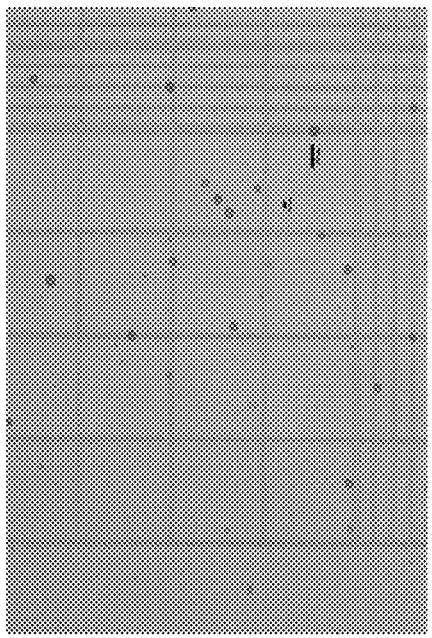

Solutions 1 and 2 above (100% acetylene) formed a cloudy mixture but few microparticles were seen under the microscope following sonication. Solution 3, however, appeared to have a pink-purple hue following 1 hour of exposure to the UV lamp (FIG. 5A), suggesting that the crosslinking process was successful. The process yielded polydisperse, size limited microparticles which were all smaller than 10 microns (FIG. 5B). There was no difference in the number of particles exposed to Triton X for 48 hours and controls (FIGS. 5C and 5D), another indication that crosslinking was successful.

The major benefit to this approach is that the microparticles are stabilized and have a structure which is likely to yield enhanced stability during handling and injection.

Microparticles Stabilized by Crosslinking of Acrylamides

Acrylamide contains a series of double bonds across its length that, in the presence of radical initiators such as AIBN or TEMED, bond to other acrylamide molecules to form a polyacrylamide mesh or gel.[12] This process is utilized to form polyacrylamide gels for gel electrophoresis.[13] No prior literature exists regarding acrylamide or polyacrylamide forming particles or microbubbles in the absence of a lipid.

To test this process, a 14 mL solution of 30% acrylamide and 8 wt % bis-acrylamide was prepared. 28 mL of pure $H_2O$ was added for a total of 42 mL. The solution was sonicated at the air/liquid interface, resulting in a change in solution to a white color and a significant increase in volume, suggesting that a foam had been formed. To this, 100 uL TEMED was added, an accelerant used to catalyze the polymerization of acrylamide and sonicated for 10 minutes.

Figure 10:
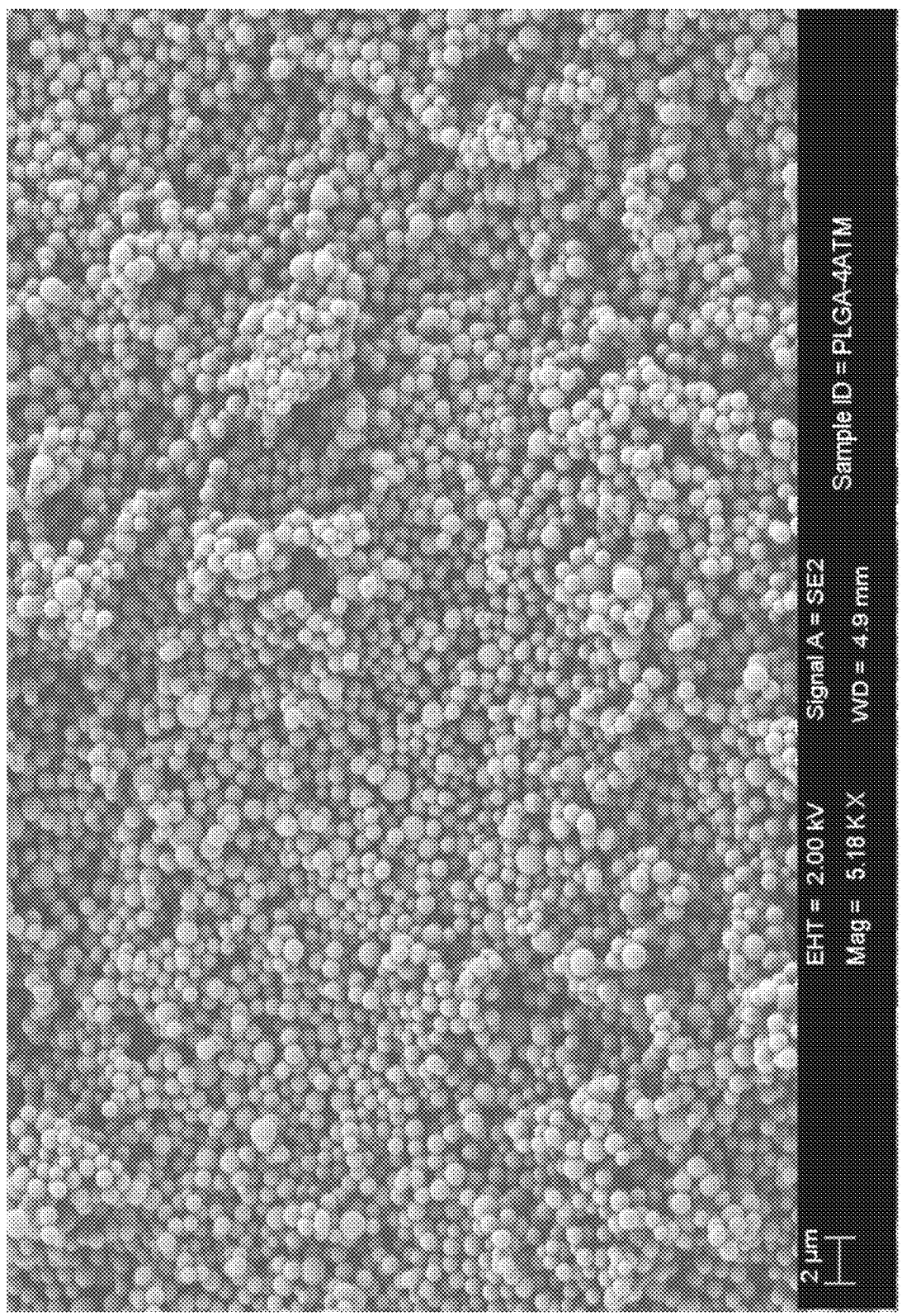
FIG. 10 shows PLGA-based microparticles manufactured by lyophilization of droplets formed using an water-oil-water double immersion technique. Following creation, these particles were pressurized to 4 atmospheres and then released over a 20 minute period.

Following this process, acrylamide bubbles were formed. However, the bubbles created under these particular conditions were somewhat unstable, visibly breaking down within minutes following the addition of TEMED (FIG. 10).

Methacrylated-BSA Particles

Background.

Bovine serum albumin (BSA) is a protein known to form air or liquid-filled microspheres with an average diameter of 2-3 um when manufactured via ultrasound sonication.[6,7] BSA contains cysteine residues which can form S—S crosslinked bonds when oxidized radical initiators TEMED and APS.[7] Methacrylic acid, a precursor to methacrylate, may also crosslink via TEMED and APS radical initiators, a gelation process that can be mediated in a wide range via reaction temperature and initiator concentration.[8] Conjugated of BSA and methacrylate can form particles that may then be initiated with TEMED and APS, forming an exceptionally strong shell.

Methods.

Methacrylated BSA was sonicated at maximal power for 2 minutes at air/liquid interface. One sample of methacrylated BSA had an acidic pH and one had a pH of 10. 100 ul TEMED and 100 UL APS were added to basic bubbles to chemically crosslink them. Results. These bubbles formed. However, the bubbles created under these particular conditions were destroyed rapidly as experienced with acrylamide. After adding TEMED and APS, a gel formed, but all bubbles were destroyed.

Example 4

Particles Stabilized in a Viscous Medium (a) 25 wt % Cargill Clearsweet 63/43 Corn Syrup 5 g non-GMP DSPC were placed into a 250 mL beaker and 91.25 g pure $H_2O$, were mixed on the stir plate (400 rpm). 62.5 g of Cargill clear sweet 63/43 corn syrup and 91.25 g of pure H2O were mixed in a separate 250 mL beaker and stirred until completely dissolved (400 rpm). The two mixtures were combined into a 500 mL beaker and mixed with the L5MA at the air/liquid interface at 3,500 rpm for 5 minutes. The speed was increased to 7,500 rpm and solution mixed for an additional 8 minutes, heating the solution. Fluid was drawn up in 140 mL syringes and centrifuged for 10 minutes at 1,000 rpm. It was found that the particles formed very well. After centrifuging the syringe separated into 3 layers. The bottom layer appeared to be cloudy water, a second viscous syrup-like layer presumed to be corn syrup with small particles embedded and a top lighter cake, which was collected. The total yield was approximately 250 mL of 80 volume % particles. Average particle size appeared to be the same size as DSPC/Chol particles via light microscopy. Particles stored for 4.5 months are of high quality.

Figure 6A:
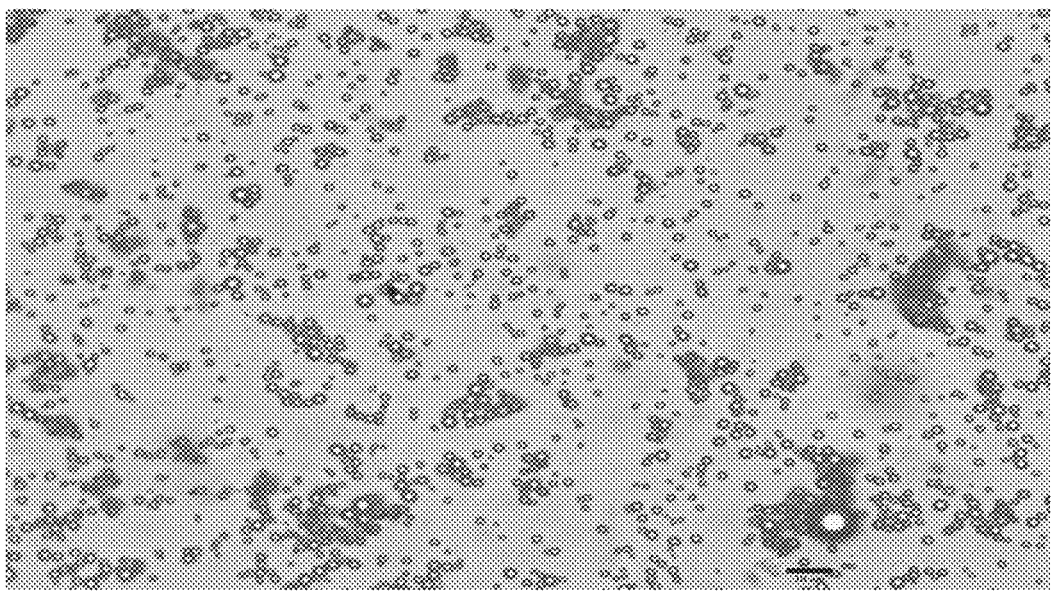
FIGS. 6A-6C depict particles manufactured under high viscosity conditions utilizing 25% and 50% corn syrup exhibited a polydisperse acceptable size distribution (FIG. 6A depicts 50% corn syrup results; top, scale bar 10 microns). The bulk particle emulsions were homogenous following manufacture (FIG. 6B) and exhibited modest product loss following storage at 4 C for 4.5 months (FIG. 6C).
Figure 6B:
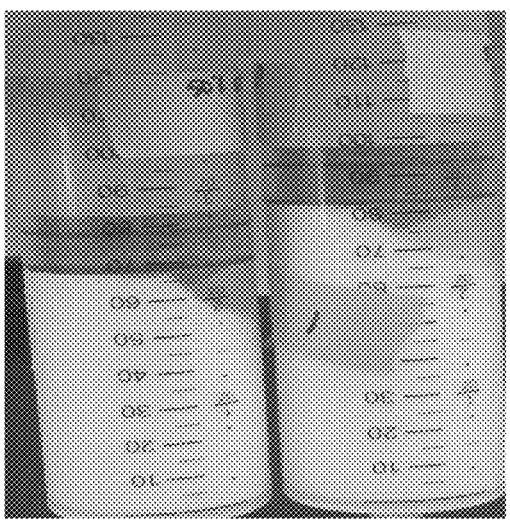
Figure 6C:
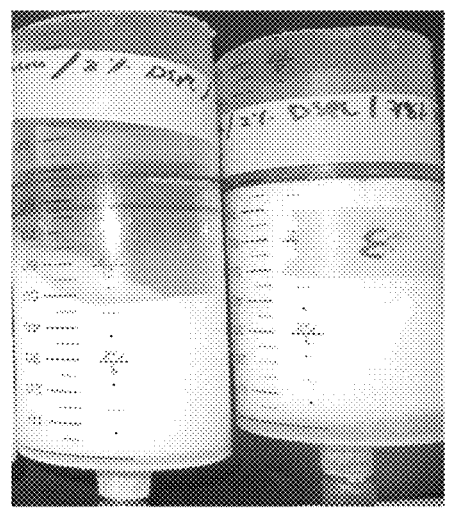

(b) 50 wt % Cargill Clearsweet 63/43 Corn Syrup 5 g non-GMP DSPC were placed into a 250 mL beaker and 60 g pure H2O, were mixed on the stir plate (400 rpm). 125 g of Cargill clear sweet 63/43 corn syrup and 60 g of pure H2O were mixed in a separate 250 mL beaker and stirred until completely dissolved (400 rpm). The two mixtures were combined into a 500 mL beaker and mixed with the L5MA at the air/liquid interface at 3,500 rpm for 5 minutes. The speed was increased to 7,500 rpm and solution mixed for an additional 8 minutes, heating the solution to ~55 C. When the solution became hot, it was briefly placed on ice to cool. Milky white fluid was drawn up in 140 mL syringes and centrifuged for 10 minutes at 1,500 rpm due to viscosity. In this experiment, the particles formed very well. After centrifuging the syringe separated into 3 layers. The bottom layer appeared to be cloudy water, a second viscous syrupy layer presumed to be corn syrup with small particles embedded and a top lighter cake, which was collected (FIG. 6A). The total yield was approximately 250 mL of 80 volume % particles. Average particle size appeared smaller than non-viscous DSPC/Chol particles via light microscopy (FIG. 6B). Particles after 4.5 months at 4 C demonstrates acceptable particle loss and a high quality, homogenous emulsion (FIG. 6C).

(c) Design of Experiments Using Corn Syrup Formulations

Given these positive results, a custom design of experiments was created to determine the optimal formulation of particles in corn syrup. Concentrations of DSPC, cholesterol, corn syrup, and water were systematically varied. DSPC was varied from 1-2 mass %, cholesterol 0-1 mass %, corn syrup 0-75 mass %, and water 22-98 mass %. Endpoints included the number of oxygen microparticles (quantified by light microscopy and a slide micrometer) and particle size 30 days after manufacture (assessed by dynamic light scattering).

Briefly, corn syrup and water were mixed in a 600 mL glass beaker and stirred at 400 rpm at 40° C. until completely dissolved. The homogenous solution was vacuum filtered through a 0.22 micron filter and hand-mixed with GMP DSPC/cholesterol as dictated by the design. The mixture was placed under a pure oxygen headspace and homogenized at 7,500 rpm with a high-shear homogenizer.

The homogenizer rotor remains submerged in the suspension for 2 minutes, causing the suspension to heat to 55° C. At 2 minutes the rotor is brought to the air-liquid interface and homogenized for 3 minutes, causing the total fluid volume to double as gas is encapsulated in lipid microparticles. The resulting viscous fluid was drawn into 100 mL syringes containing 50 mL oxygenated diluent (plasma-lyte A). Following shaking, the emulsion was centrifuged (1,500 rpm for 10 minutes) and the resultant cake stored for 30 days at room temperature.

At 30 days, the total number of microparticles of each formulation was determined by the cake volume multiplied by the concentration of microparticles in the foam, which was determined as follows: 100 µl of foam and 1 mL pure $H_2O$ were vortexed in an Eppendorf tube and 10 µl placed on a hemocytometer for quantification by light microscopy. The number of particles in 1 mL of concentrated foam was calculated based on the average number of microparticles per grid (determined from counting particles on 5 grids) multiplied by the volume factor of the hemocytometer, and by the dilution factor of the suspension.

At 30 days, photomicrographs of diluted foam were taken and analyzed for particle size. ImageJ software was used to outline each particle in the photomicrograph and determine the microparticle area based on magnification after which the area of 33 microparticles was converted to diameter and the mean calculated for analysis.

Finally, the optimal particle emulsion was analyzed by scanning electron micrograph to determine the mechanism by which these microparticles were highly stable and size-limited. Samples were prepared as above, then frozen and transferred into MED 020 using VCT100 cryo transfer device. Samples were fractured at −150° C., then etched at −90° C. for 1 minute. Samples were then coated with 8 nm of platinum. The prepared samples were transferred into Zeiss Nvision using VCT 100. Samples were imaged using a Leica cryo stage with a temperature of −150° C. at 2 kV and a working distance of 2 mm.

Figure 7:
FIG. 7 depicts the optimized particles composed of DSPC only and made within 73% corn syrup demonstrated a smooth surface without holes or cracks on the microparticle surface. Also note the lack of debris seen using this manufacturing process.

It was found that increasing mass fractions of corn syrup resulted in lower mean particle size and a greater number of particles formed and preserved. Particles were formed from clearsweet corn syrup (Cargill, 63/43), DSPC, and water were mixed in a 75:2:23 ratio, 50:2:48 ratio, and a 25:2:73 ratio. Formulations containing the maximum fraction of corn syrup (75%) resulted in a mean particle diameter of 0.77 microns versus 5.42 microns for formulations containing no corn syrup. Similarly, maximum corn syrup fractions resulted in $3.67 \times 10^{10}$ particles per mL versus $2.8 \times 10^7$ particles per mL for formulations manufactured with the minimum fraction of corn syrup. The optimal formulation of lipid-oxygen microparticles based on the analysis was found to be 75 mass % corn syrup, 23.6 mass % water, and 1.4 mass % DSPC. Of note, in the presence of a high viscosity emulsion, the addition of cholesterol was not necessary for optimally stable microparticles. Scanning electron micrography (FIG. 7) demonstrated (a) a very clean emulsion without significant quantities of lipid debris, speaking to the efficacy of the cleaning process; (b) a very small size distribution of microparticles, mostly under 2-3 microns in diameter; (c) an absence of surface defects such as holes or cracks. This likely explains the significant stability found in these microparticle emulsions.

The benefits to this approach are the ease of formulation, the cleanliness of the resulting emulsion, and the stability of the particles. For example, the size distribution of these particles was significantly improved compared to manufacture in plasmalyte. The number % of particles exceeding 10 microns was 1.1% in corn syrup and ~9-11% in plasmalyte. The size difference is pronounced in the micrographs. The shelf life of particles formed from high viscosity corn syrup is also substantially better than in saline or plasmalyte.

Example 5

Poly(Lactic-Co-Glycolic Acid) (PLGA) Polymer Based Microparticles

PLGA is broken down by hydrolysis into lactic acid and glycolic acid, both of which can be metabolized easily in the liver. The thickness of the shell, its burst and crush strengths, and the diffusivity of the gas can be engineered through the thickness of the shell and the proportion of each moiety within the polymer itself.

PLGA microparticles were manufactured using an water-oil-water technique as follows. PLGA was dissolved in dichloromethane and corn syrup. This emulsion was then then sonicated in the presence of water, then again amalgamated with dichloromethane (an organic solvent). The emulsion was then snap frozen in liquid nitrogen and freeze dried over a 2 day period. This resulted in a narrow size distribution when assessed by light microscopy. Additionally, a fluorophore known as Dylight-488 was encapsulated within the PLGA microparticles to prove that the microparticles were in fact hollow structures.

Although polymer based particles could be created it was no clear that a thick, polymer based shell would be able to transfer oxygen gas efficiently to surrounding blood and tissues. In order to test whether the lyophilized particles could carry oxygen gas and transfer it to another fluid, a lyophilized pellet was washed with oxygen gas at 1 LPM for 10 minutes in a closed 50 mL conical tube. Sterile water (1 mL) was added to an eppendorf tube, and the baseline PO2 was monitored for 10 minutes under exposure to room air. Subsequently, 4 mg of either oxygenated water, DSPC particles made within 50 weight % corn syrup, or PLGA particles were added to the eppendorf tube, which was inverted gently until the emulsions were visibly mixed. The PO2s were then monitored for a 15 minute period. Finally, to formally characterize the size distribution of these particles, lyophylized PLGA microparticles were assessed by dynamic light scattering (Delsa Nano).

Figure 8:
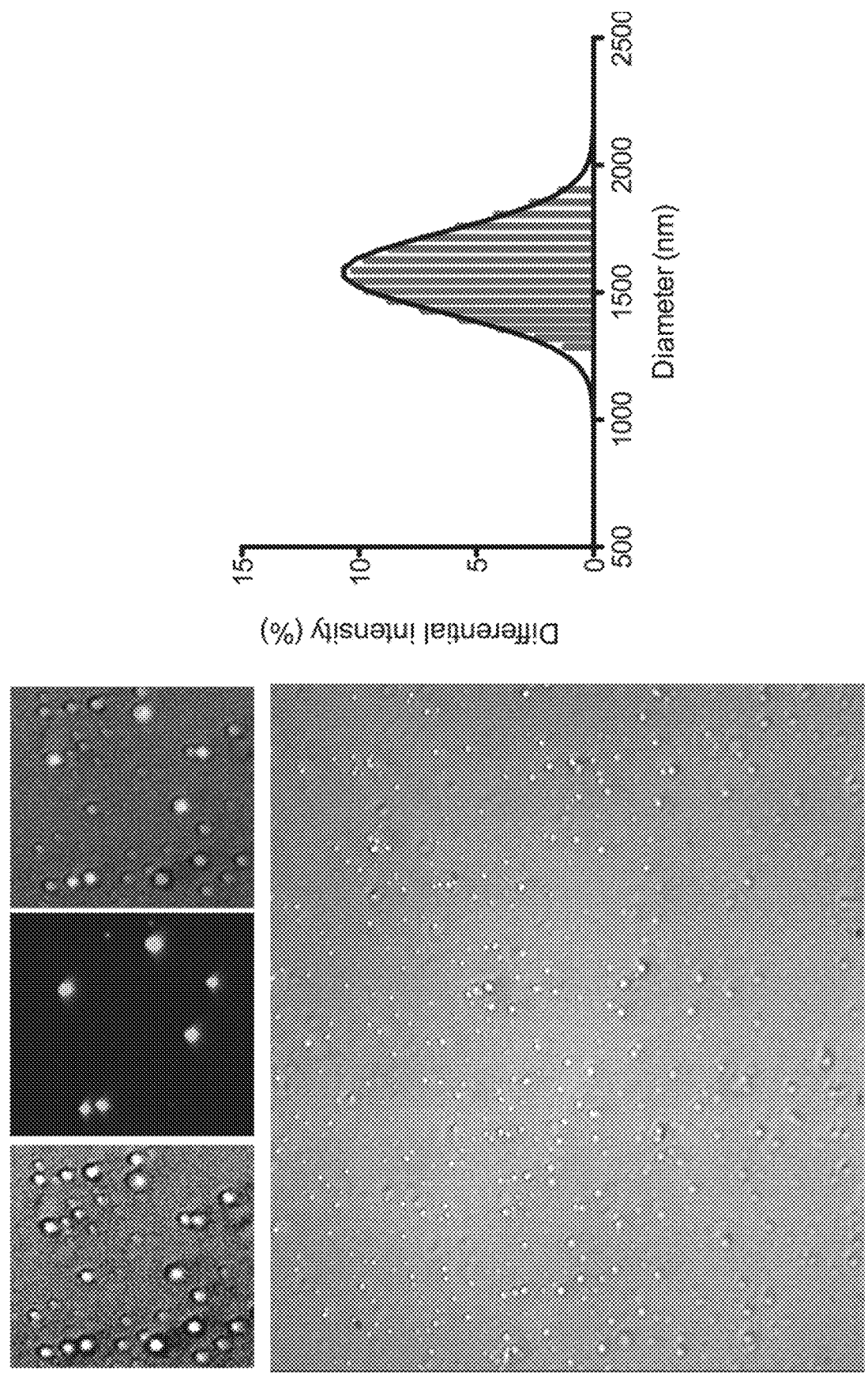
FIG. 8 depicts PLGA particles were less polydisperse other particles, and were able to contain a fluorophore within them. The size distribution of these microparticles was confirmed to be between 1 and 2 microns in diameter by dynamic light scattering analysis.

As shown in FIG. 8, PLGA formed using this water-oil-water double emulsion technique formed a beautifully clean emulsion of microparticles with a very narrow size distribution, including a maximal size of 2 microns. This represents a substantial improvement over lipid microbubbles. Polymer based particlex exhibit a stronger tensile strength than self-assembling microparticles.

Figure 9:
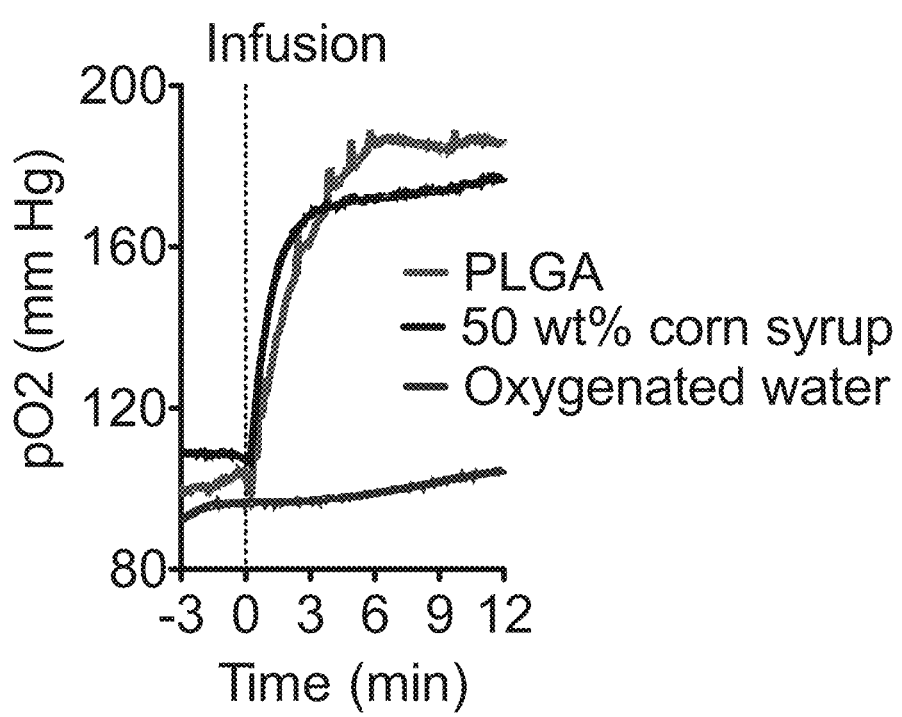
FIG. 9 depicts water at atmospheric pressure has a baseline PO2 of ~100 mmHg. When exposed to oxygenated water, this does not increase. However, when exposed to 4 mg of oxygenated PLGA microparticles, the increase in PO2 was approximately the same rate and quantity as when it was exposed to DSPC-cholesterol particles made in 50 weight % corn syrup.

These particles exhibited the same oxygen release profile in air-exposed water as did DSPC-cholesterol-corn syrup particles (FIG. 9), which do exhibit a very rapid oxygen release profile in vivo. FIG. 10 shows PLGA-based particles manufactured by lyophilization of droplets formed using an water-oil-water double immersion technique. Following creation, these particles were pressurized to 4 atmospheres and then released over a 20 minute period. There is no evidence on SEM of either crushing or bursting of the particles. The microparticles can be manufactured using a spray dryer, which is the mechanism by which many commercially available drugs are manufactured. This permits the use of these particles for small and large animal experiments.

General Method A for Preparing Particles

Oxygen microparticles (OMPs) were manufactured according to the following method: one or more microparticle components (e.g., lipids, cholesterol, PF127 etc.) are suspended in 1 liter of Plasma-Lyte A and agitated at 7,000 RPM for 3 minutes using a high-shear mixer (Silverson L5MA). The liquid suspension is transferred to a gas-tight vessel with a pure oxygen headspace and it is run with a constant infusion of oxygen gas (0.5 LPM) through a high-shear homogenizer (7,500 RPM, Silverson Verso™, Silverson Machines, Incorporated). Microparticles are cooled by a 4° C. heat-exchanger and returned to the vessel for serial concentration. Fluid is recycled for 10 minutes and removed for concentration by centrifugation (1,000 RPM for 10 minutes). Excess Plasma-Lyte A is expelled and OM concentrates are placed in 50 mL aliquots.

General Method B for Preparing an Ionically Crosslinked Membranes

The oxygen microparticles (OMPs) may be stabilized by contacting the pre-formed OM with one or more materials which may form ionic bonds to form an external ionically crosslinked shell surrounding the OM stabilized membrane. An example of such a material is a material which may form a hydrogel, such as alginate.

In one example, an alginate and 1× phosphate buffered saline solution (1% alginate by weight) are added to 50 mL of concentrated (90% gas by volume) oxygen microparticles (OMPs). Alginate solution and OMPs were mixed by gentle inversion for 10 minutes and concentrated by centrifugation (1,000 RPM for 10 minutes). Excess alginate-PBS solution was expelled and 40 mL of calcium chloride (1M) was mixed in with each syringe to ionically crosslink the alginate to form an external alginate hydrogel film stabilizing the OM. The OMPs may be concentrated via centrifugation (1,000 RPM for 10 minutes) and placed in gas-tight glass test tubes (10 mL) for further analysis.

General Method C for Preparing Non-Covalently Crosslinked Stabilized Membranes

The oxygen microparticles (OMPs) may be stabilized by adding one or more materials which may form ionic bonds as one of the microparticle components following General Method A. In this case, the OM stabilized membrane is stabilized not by an external polymer shell, but is stabilized by one or more ionically crosslinked materials within and throughout the OM stabilized membrane. An example of such a material is a material which may form a hydrogel, such as alginate.

In one example, the alginate and one or more additional microparticle components are mixed following General Method A. Crosslinking of the alginate with calcium chloride forms an ionically crosslinked OM.

General Method D for Preparing Covalently Crosslinked Membranes

The oxygen microparticles (OMPs) may be stabilized by contacting the pre-formed OM with a material which may covalently crosslink to form an external polymerized crosslinked shell, i.e., an membrane surrounding the OM stabilized membrane. An example of such a material may be an acrylate, for example PF127 modified with acrylate groups.

In one example, the pre-formed OM is mixed with a solution of the diacrylate (in which the acrylate assembles around the OMPS). Chemical crosslinking of the diacrylate is then initiated, and an external polymer shell stabilizing the OMPS. In one embodiment, radical formation may be induced by sonication in aqueous media. Other methods of polymerization include UV light initiation, and chemical initiation or crosslinking.

General Method D for Preparing Covalently Crosslinked Stabilized Membranes

The oxygen microparticles (OMPs) may be stabilized by adding one or more polymerizable materials as one of the microparticle components following General Method A. In this case, the OMPS stabilized membrane is stabilized not by an external polymer shell, but is stabilized by a crosslinked polymer within and throughout the OMPS stabilized membrane. An example of such a material may be an acrylate, for example PF127 modified with acrylate groups.

In one example, the acrylate and one or more additional microparticle components are mixed following General Method A. Crosslinking of the acrylate is then initiated to form a covalently crosslinked OMPS. In one embodiment, radical formation may be induced by sonication in aqueous media. Other methods of polymerization include UV light or chemical initiation, and/or chemical crosslinking, e.g., by Click chemistry.

General Method E for Preparing Stabilized Membranes with Stabilizing Agent

The oxygen microparticles (OMPs) may be stabilized by adding one or more stabilizing agents as a microparticle component following General Method A.

General Method F for Preparing Biopolymer Disulfide Stabilized Membranes

The oxygen microparticles (OMPs) may be stabilized by adding one or more biopolymers (e.g., proteins, sugars) which contain —SH moieties (e.g., such as cysteine) as a microparticle component following General Method A. Sonication produces superoxide which in turn reacts with two —SH groups to form a disulfide bond, chemically crosslinking the biopolymer around the oxygen core. One such biopolymer is the protein bovine serum albumin (BSA). Addition of oxidation reagents such as $H_2O_2$ can drive oxidation of disulfides while addition of reducing agents such as DTT can reduce them.

General Method G for Preparing Modified Biopolymer Stabilized Membranes

The oxygen microparticles (OMPs) may be stabilized by adding one or more biopolymers (e.g., proteins, sugars) functionalized with groups which may non-covalently react with other groups to form a covalent bond, as a microparticle component following General Method A. An example of a modified biopolymer is bovine serum albumin (BSA) or gelatin modified with reactive acrylate (e.g., methacrylate) groups.

BSA and gelatin may be methacrylated via the following procedure.

1 g of BSA and gelatin may be dissolved in 10 mL of PBS at 50 C. 1 mL of methacrylic anhydride may be added to the stirring mixture at a constant rate of 0.5 mL/min and the reaction may proceed for 24 hrs at 50 C. The reaction may be diluted with 40 mL of 40 C PBS and dialyzed with 12000-14000 MWCO dialysis tubing for 1 week against 40 C ddH2O to remove the methacrylic acid and other impurities, followed by freeze drying. The amount of lysine groups modified on the BSA or gelatin macromer may be determined by using 2,4,6-trinitrobenzenesulfonic acid as previously described. This may be confirmed with nuclear magnetic resonance spectroscopy This method may allow for the degree of lysine groups modified on the BSA/gelatin macromers to be controlled through limiting reactant (methacrylic anhydride) available to produce shells with various moduli. The range for degree of methacrylation may vary between 0% and 60%.

Production of microparticles may be achieved by dissolving the BSA/gelatin-methacrylate monomer into solution and sonicating in the presence of oxygen following General Method A. The stabilized membrane may be created by heating an albumin or gelatin solution to the point of denaturing and then exposing it to high intensity emulsification in the presence of oxygen. The denatured proteins adsorb to the free gas-liquid interface created during gas entrapment, while the cavitation-generated radicals will polymerize the methacrylate groups, creating a random network of adsorbed proteins that entraps the oxygen and gives the microparticle its rigidity.

B. Tables 1 and 2 comprise materials envisioned useful in preparation of the inventive particles.

TABLE 1

MATERIALS WITH UNSATURATED LIPID TAILS

| Class | Structure |
|---|---|
| Phospholipids with one tail | 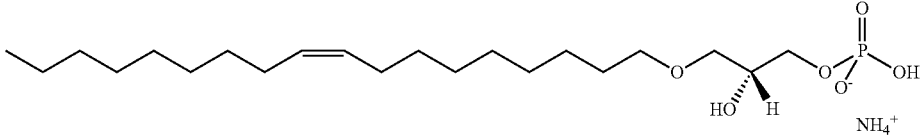 [SMILES: CCCCCCCC/C=C\CCCCCCCCOC[C@@H](O)COP(=O)([O-])O ; [NH4+]] |
| | 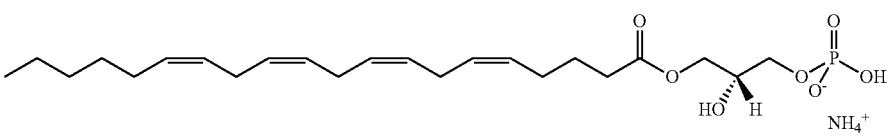 |
| | 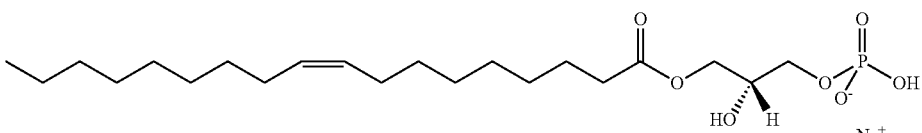 |
| | 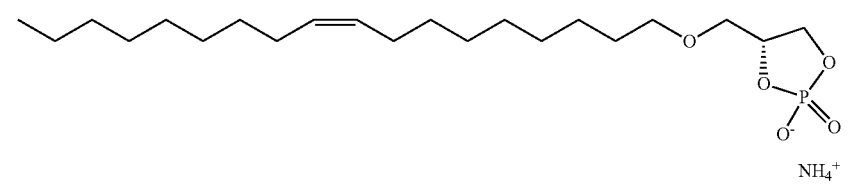 |
| | 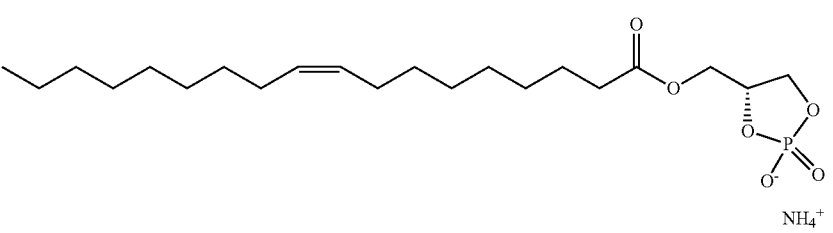 |
| | 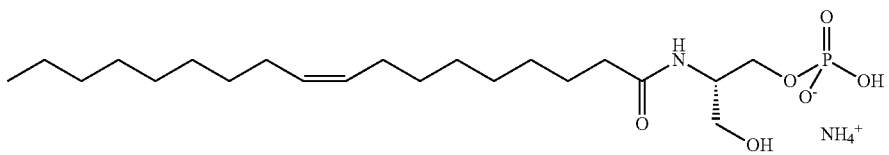 [SMILES: CCCCCCCC/C=C\CCCCCCCC(=O)N[C@@H](CO)COP(=O)([O-])O ; [NH4+]] |
| | 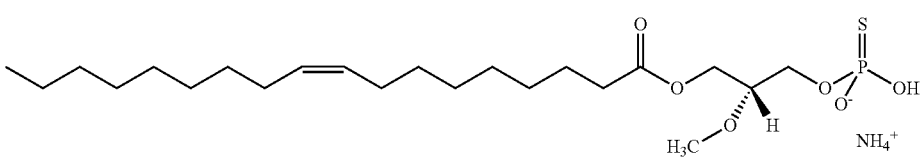 [SMILES: CCCCCCCC/C=C\CCCCCCCC(=O)OC[C@H](COP([O-])(O)=S)OC ; [NH4+]] |

TABLE 1-continued

MATERIALS WITH UNSATURATED LIPID TAILS

| Class | Structure |
|---|---|
| | (structures) |
| Phospholipids with double and/or triple bonds in one tail | (structure) |

TABLE 1-continued
MATERIALS WITH UNSATURATED LIPID TAILS
| Class | Structure |
|---|---|
| | 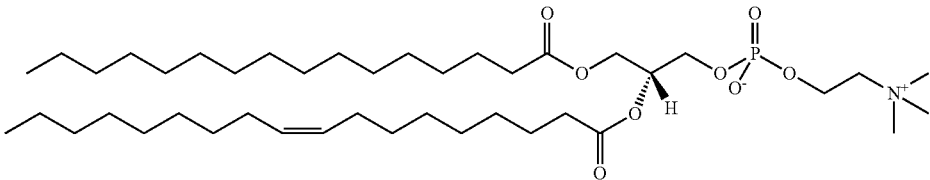 Structure of predominant species |
| | 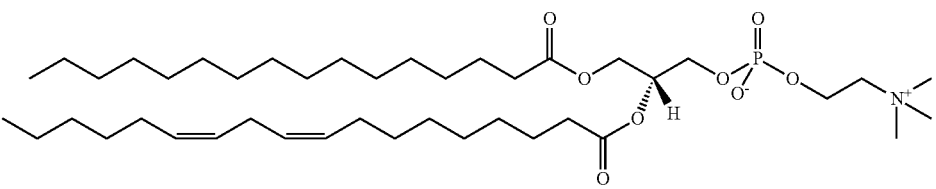 Structure of predominant species |
| | 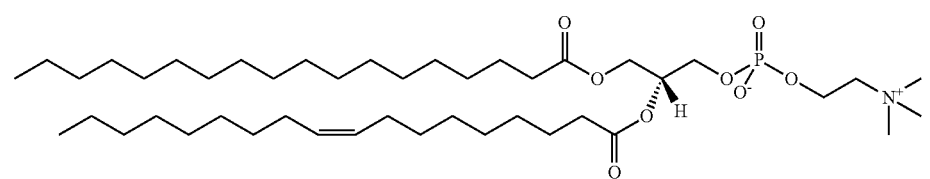 Structure of predominant species |
| | 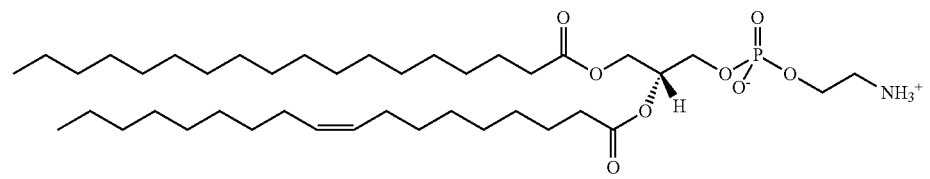 [SMILES: CCCCCCCC/C=C\CCCCCCCC(=O)O[C@H](COC(=O)CCCCCCCCCCCCCCCCC)COP(=O)([O-])OCC[NH3+]] |
| | 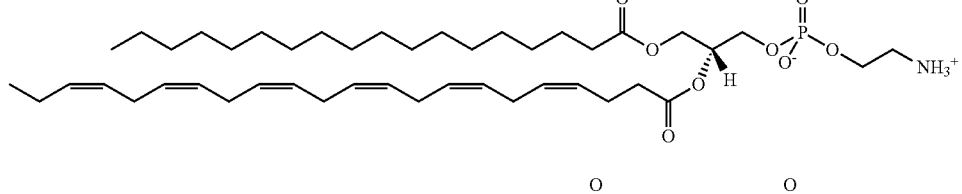 |
| | 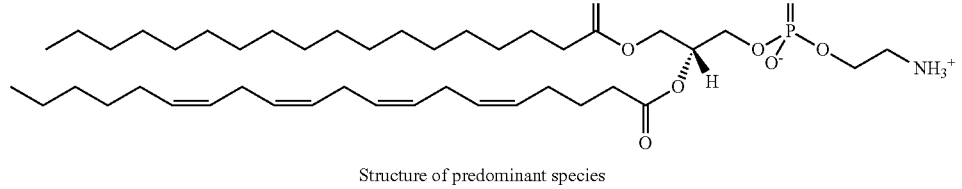 Structure of predominant species |
| | 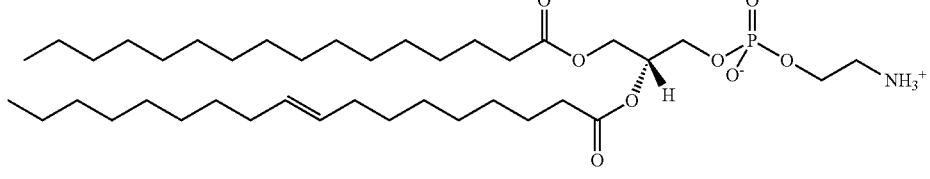 Structure of predominant species |

TABLE 1-continued
MATERIALS WITH UNSATURATED LIPID TAILS
| Class | Structure |
|---|---|
| | 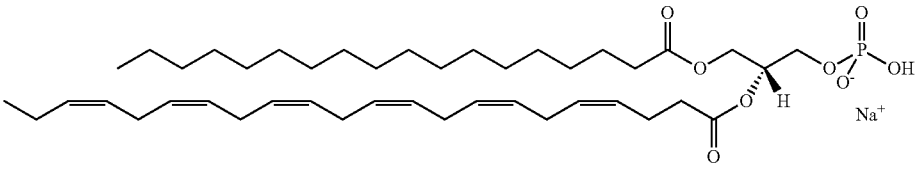 [SMILES: CC/C=C\C/C=C\C/C=C\C/C=C\C/C=C\C/C=C\CCC(=O)O[C@H](COC(=O)CCCCCCCCCCCCCCCCC)COP(=O)([O-])O ; [Na+]] |
| | 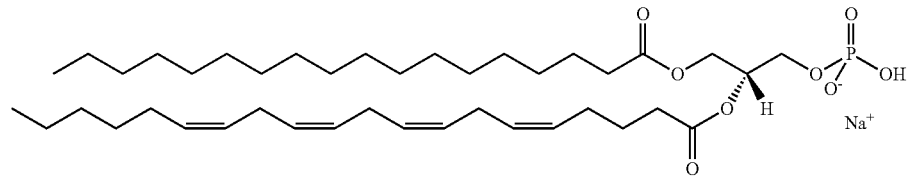 [SMILES: CCCCC/C=C\C/C=C\C/C=C\C/C=C\CCCC(=O)O[C@H](COC(=O)CCCCCCCCCCCCCCCCC)COP(=O)([O-])O ; [Na+]] |
| | 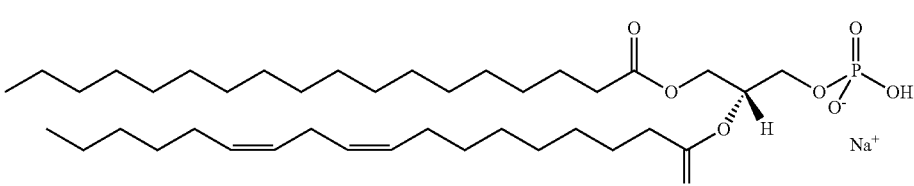 |
| | 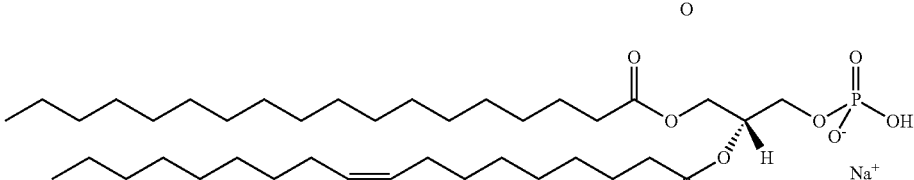 |
| | 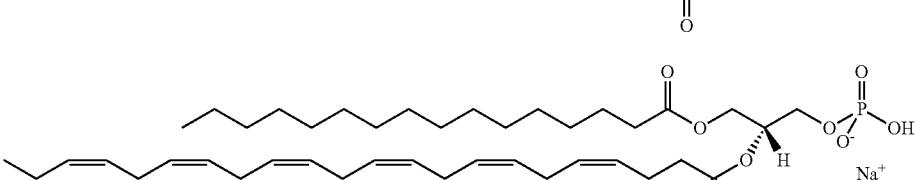 |
| | 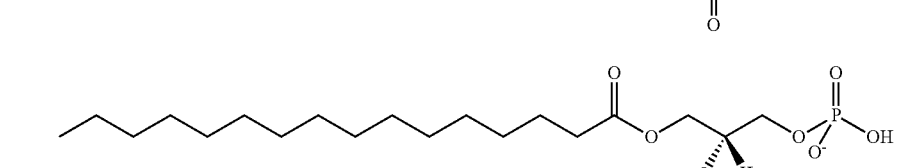 |
| | 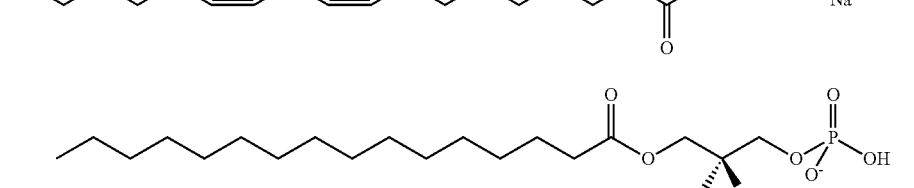 |
| | 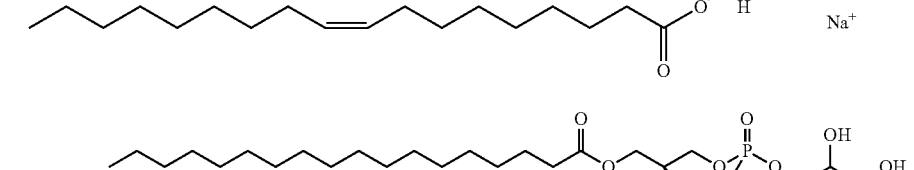 |

TABLE 1-continued
MATERIALS WITH UNSATURATED LIPID TAILS
| Class | Structure |
|---|---|
| | 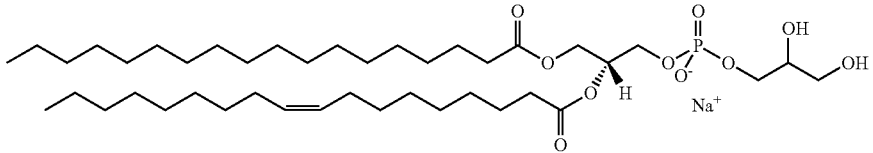 [SMILES: CCCCCCCC/C=C\CCCCCCCC(=O)O[C@H](COC(=O)CCCCCCCCCCCCCCCCC)COP(=O)([O-])OCC(O)CO ; [Na+]] |
| | 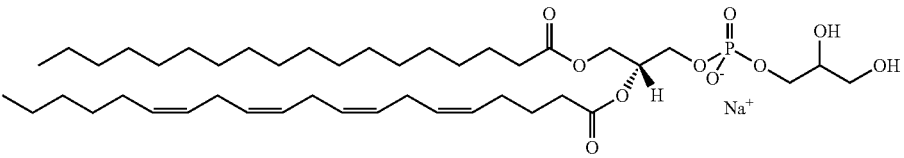 [SMILES: CCCCC/C=C\C/C=C\C/C=C\C/C=C\CCCC(=O)O[C@H](COC(=O)CCCCCCCCCCCCCCCCC)COP(=O)([O-])OCC(O)CO ; [Na+]] |
| | 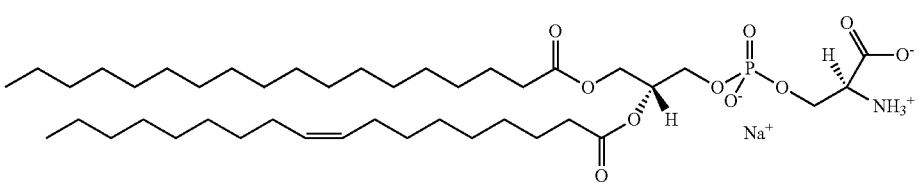 [SMILES: CCCCCCCC/C=C\CCCCCCCC(=O)O[C@H](COC(=O)CCCCCCCCCCCCCCCCC)COP(=O)([O-])OC[C@H]([NH3+])C(=O)[O-] ; [Na+]] |
| | 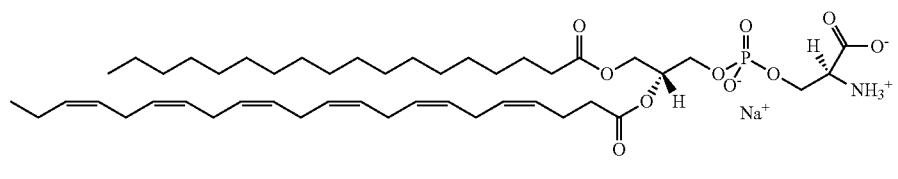 [SMILES: CC/C=C\C/C=C\C/C=C\C/C=C\C/C=C\C/C=C\CCC(=O)O[C@H](COC(=O)CCCCCCCCCCCCCCCCC)COP(=O)([O-])OC[C@H]([NH3+])C(=O)[O-] ; [Na+]] |
| | 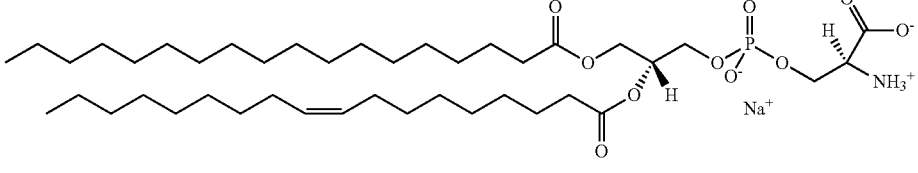 |
| | 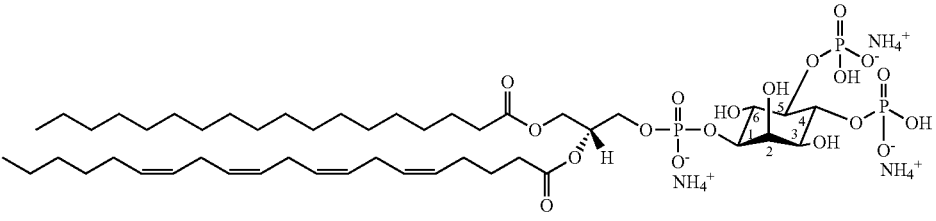
Structure of predominant species |
| | 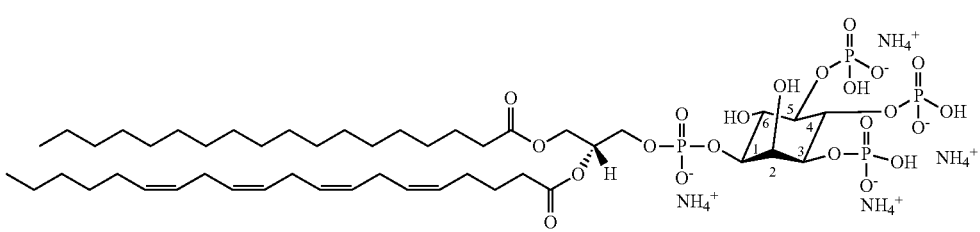 |
| | 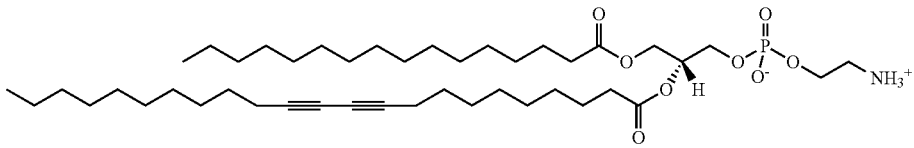 [SMILES: CCCCCCCCCCC#CC#CCCCCCCCCC(=O)O[C@H](COC(=O)CCCCCCCCCCCCCCC)COP(=O)([O-])OCC[NH3+]] |

TABLE 1-continued
MATERIALS WITH UNSATURATED LIPID TAILS
| Class | Structure |
|---|---|
| | 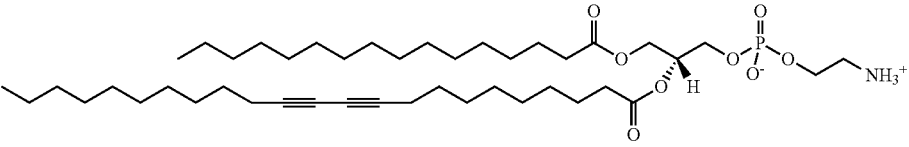 [SMILES: CCCCCCCCCCC#CC#CCCCCCCCCC(=O)O[C@H](COC(=O)CCCCCCCCCCCCCCC)COP(=O)([O-])OCC[NH3+]] |
| | 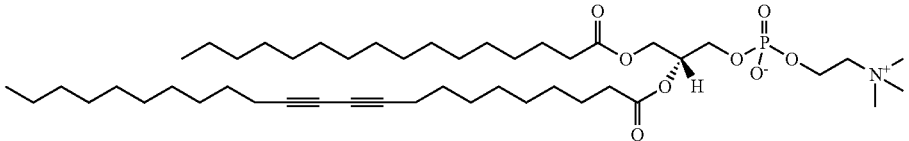 [SMILES: CCCCCCCCCCC#CC#CCCCCCCCCC(=O)O[C@H](COC(=O)CCCCCCCCCCCCCCC)COP(=O)([O-])OCC[N+](C)(C)C] |
| | 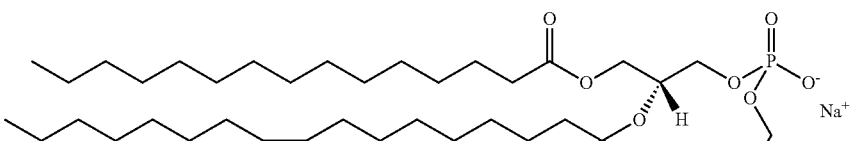
Structure of predominant species |
| Phospholipids with double and/or triple bonds in two tails | 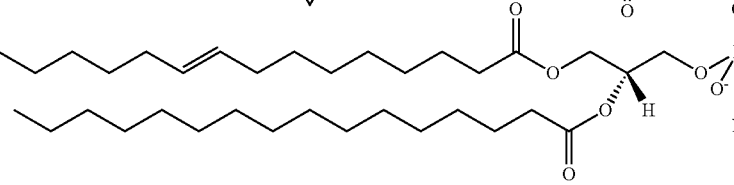 |
| | 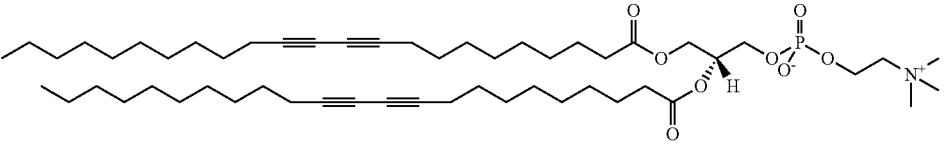 [SMILES: CCCCCCCCCCC#CC#CCCCCCCCCC(=O)OC[C@H](COP(=O)([O-])OCC[N+](C)(C)C)OC(=O)CCCCCCCCC#CC#CCCCCCCCCCC] |
| | 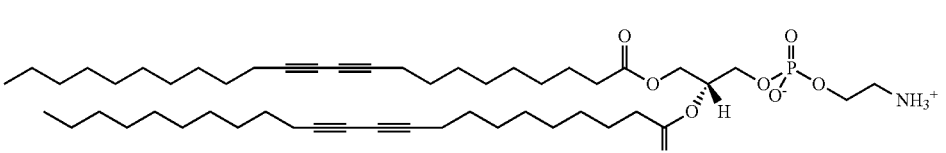
Structure of predominant species |
| | 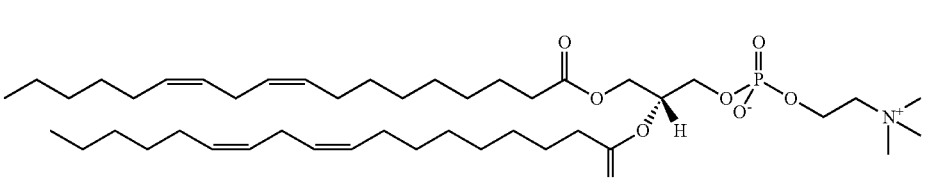 |

TABLE 1-continued
MATERIALS WITH UNSATURATED LIPID TAILS
| Class | Structure |
|---|---|
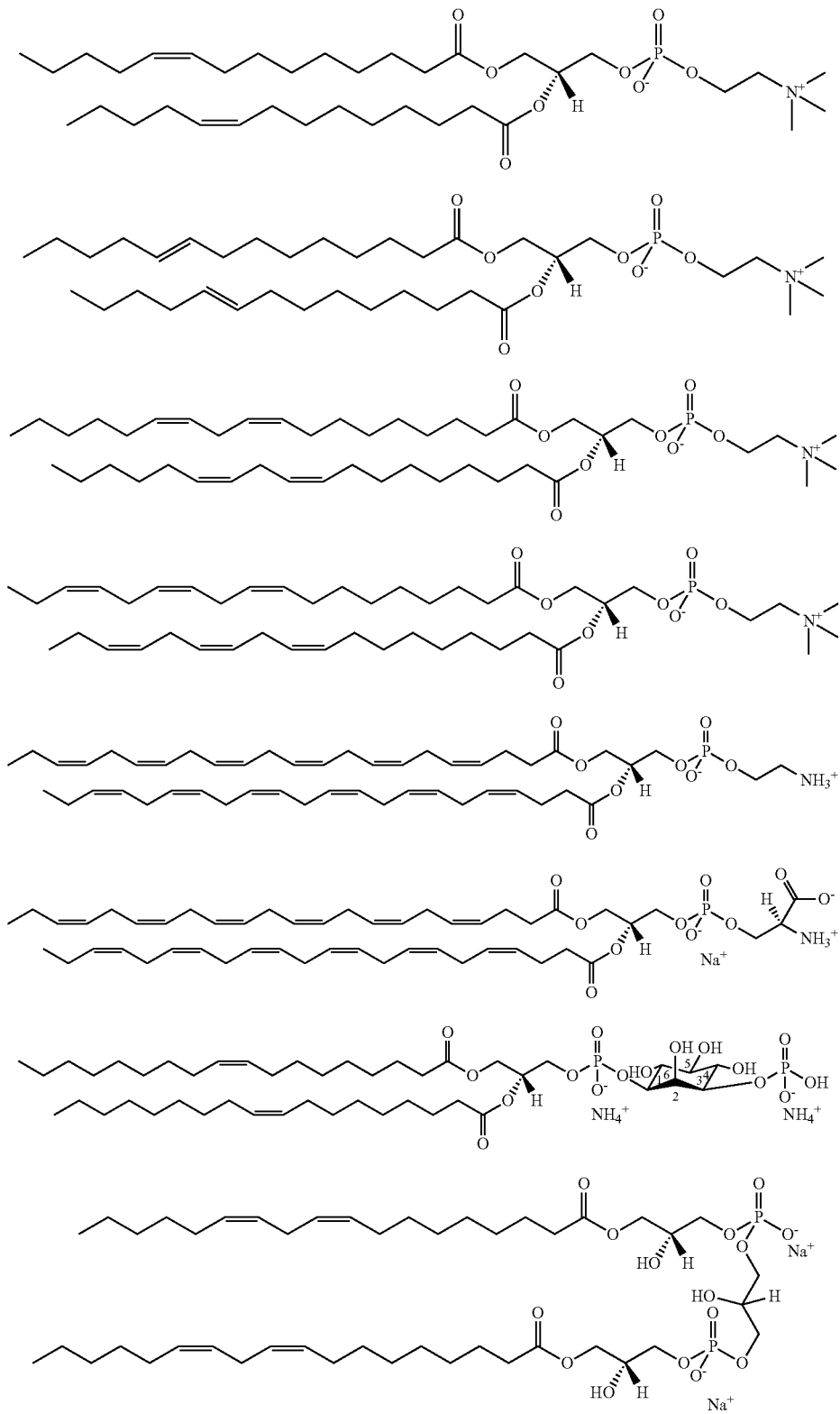
Structure of predominant species TABLE 1-continued
MATERIALS WITH UNSATURATED LIPID TAILS
| Class | Structure |
|---|---|
| | 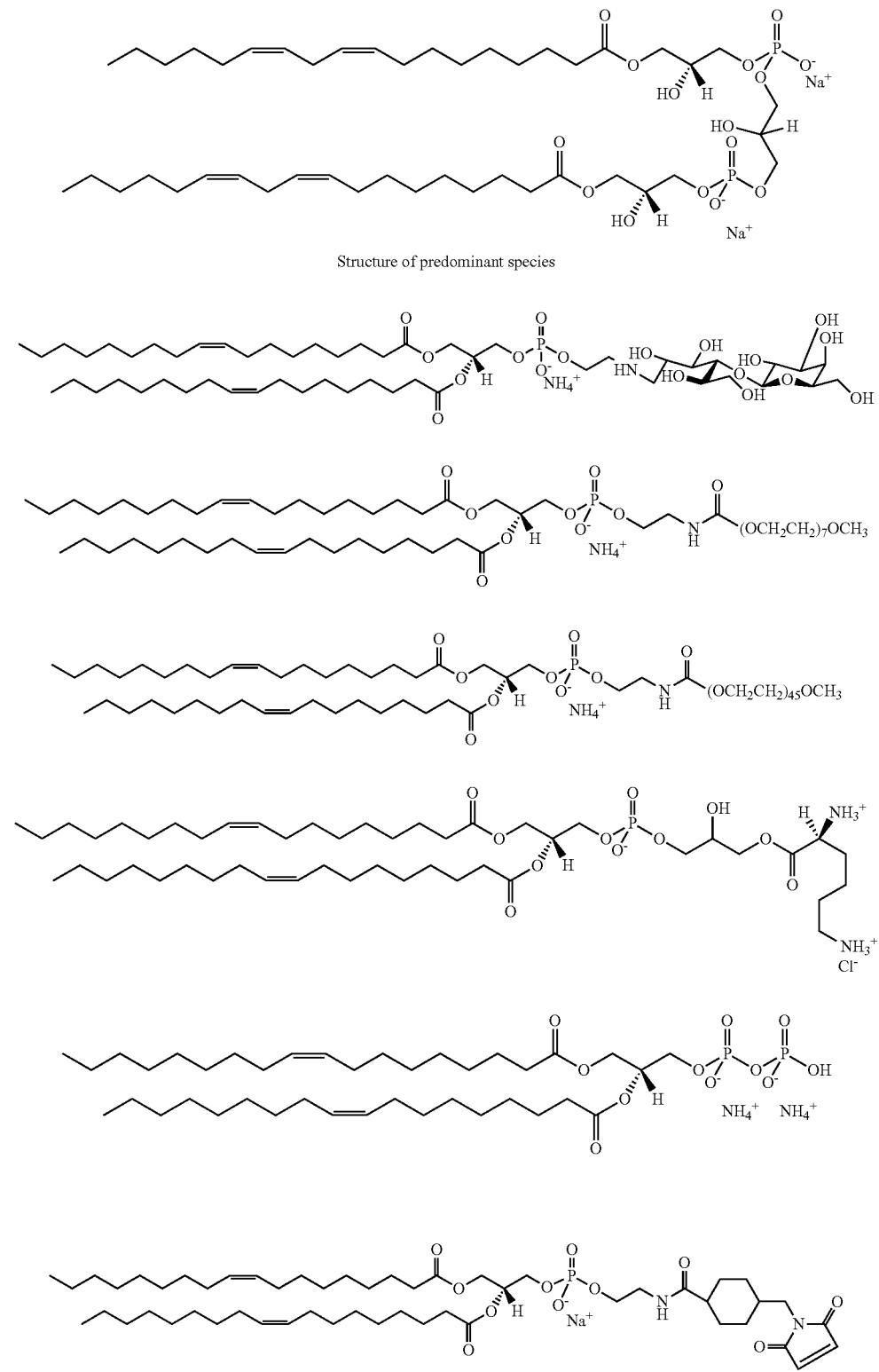 |
Structure of predominant species TABLE 1-continued
MATERIALS WITH UNSATURATED LIPID TAILS
| Class | Structure |
|---|---|
| Phospholipids with double and/or triple bonds in three or four tails | 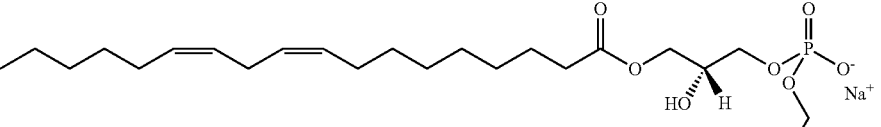<br>Structure of predominant species<br>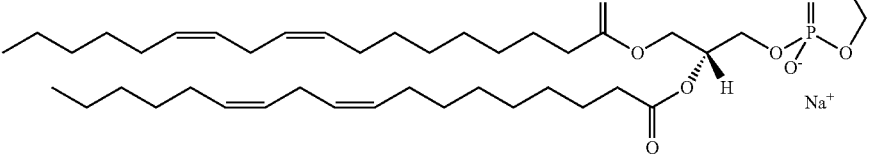<br>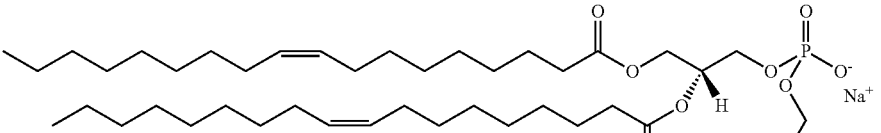<br>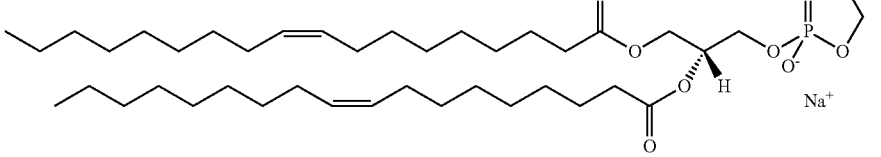 |
| Fatty acids, amides, esters | 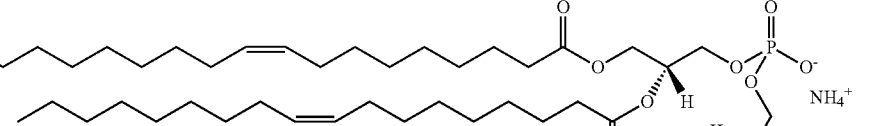 |

TABLE 1-continued
MATERIALS WITH UNSATURATED LIPID TAILS
| Class | Structure |
|---|---|
| | 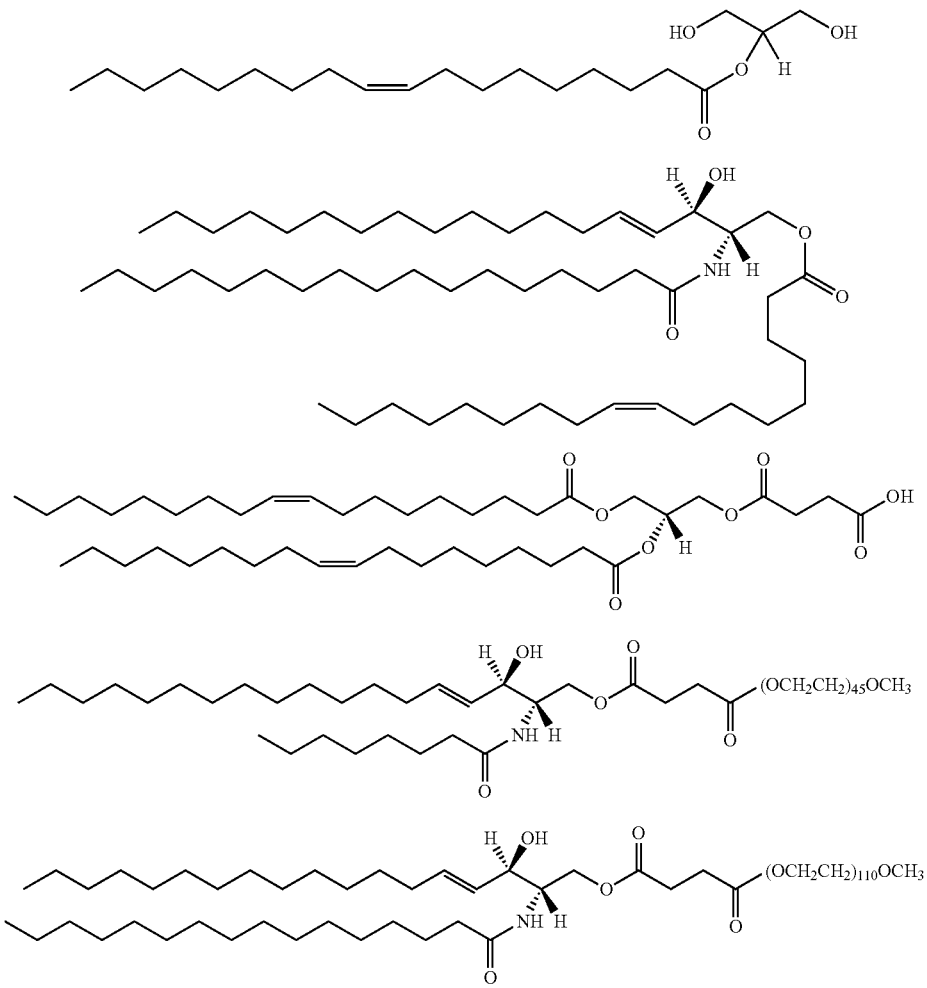 |
TABLE 2
MATERIALS WITH SATURATED LIPID TAILS
| Class | Structure |
|---|---|
| Saturated Phospholipids | 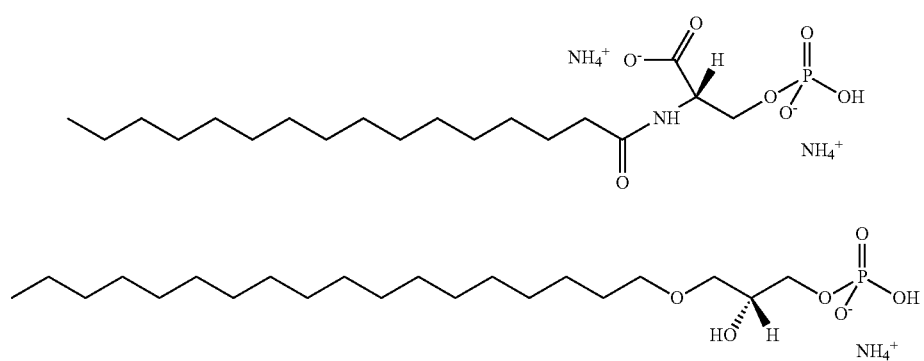 |

TABLE 2-continued
MATERIALS WITH SATURATED LIPID TAILS
| Class | Structure |
|---|---|
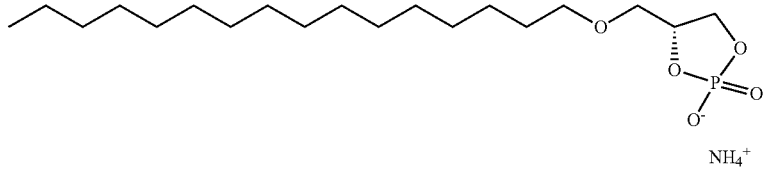
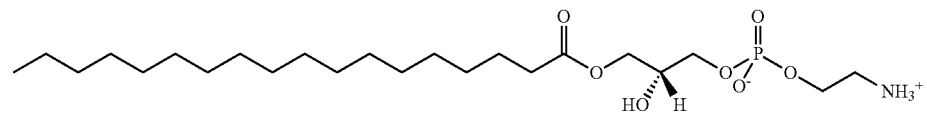
Structure of predominant species
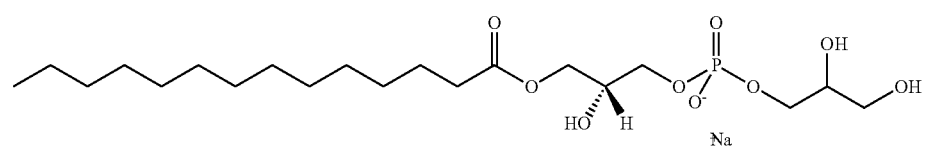 [SMILES: CCCCCCCCCCCCCC(=O)OC[C@@H](O)COP(=O)([O-])OCC(O)CO ; [Na+]]
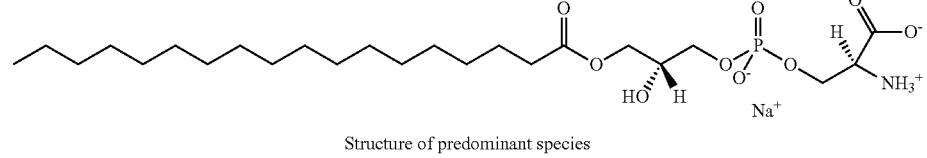
Structure of predominant species
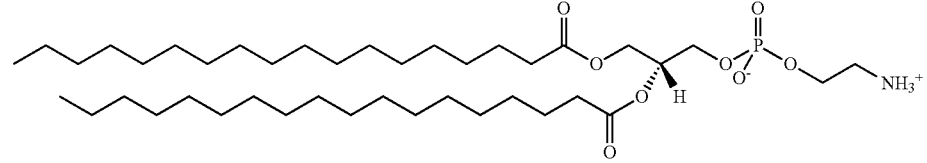
1,2-Distearoyl-sn-glycero-3-phosphocholine (DSPC)
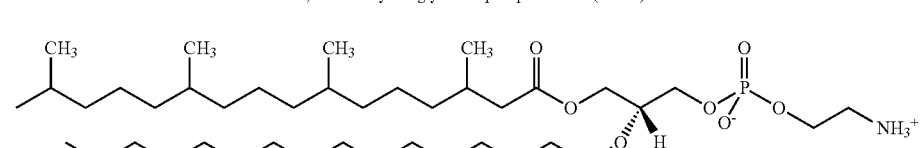
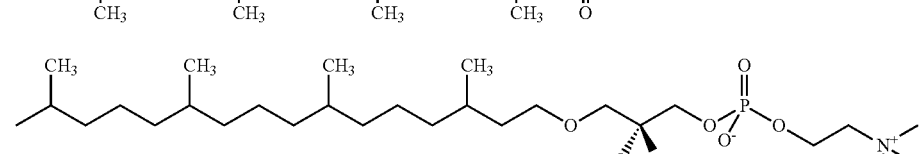
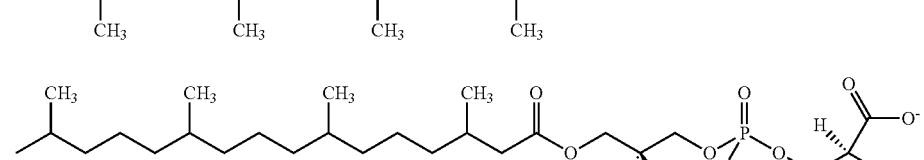

US 10,577,554 B2
TABLE 2-continued
MATERIALS WITH SATURATED LIPID TAILS
| Class | Structure |
|-------|-----------|
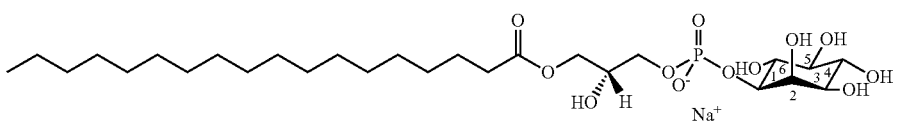
Structure of predominant species
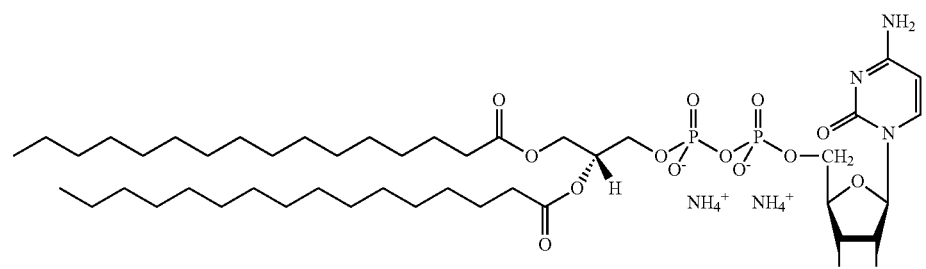
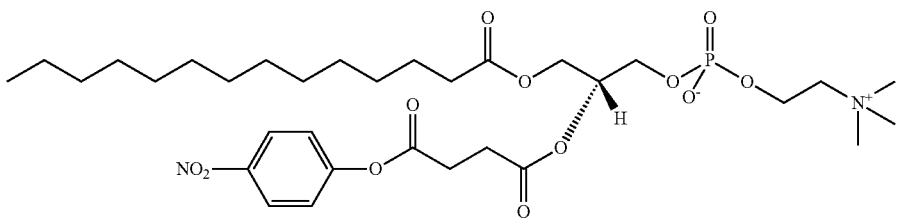 [SMILES: CCCCCCCCCCCCCC(=O)OC[C@H](COP(=O)([O-])OCC[N+](C)(C)C)OC(=O)CCC(=O)Oc1ccc([N+](=O)[O-])cc1]
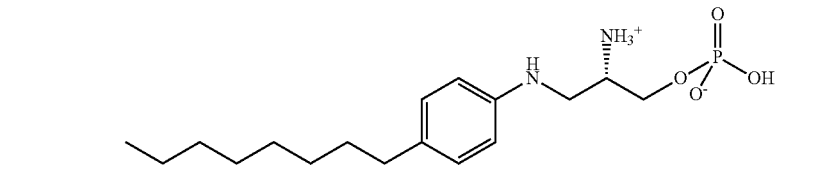 [SMILES: CCCCCCCCc1ccc(NC[C@H]([NH3+])COP(=O)([O-])O)cc1]
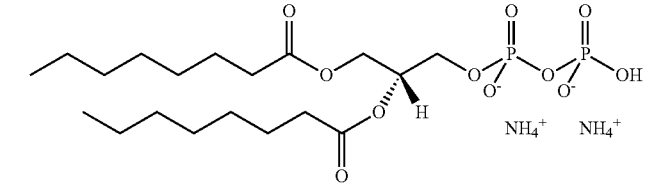 [SMILES: CCCCCCCC(=O)OC[C@H](COP(=O)([O-])OP(=O)([O-])O)OC(=O)CCCCCCC ; [NH4+] ; [NH4+]]
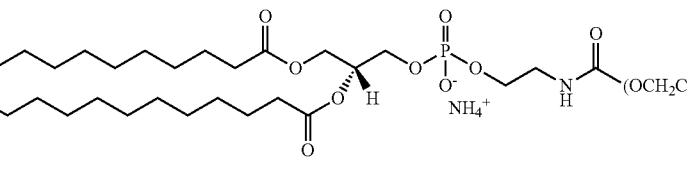
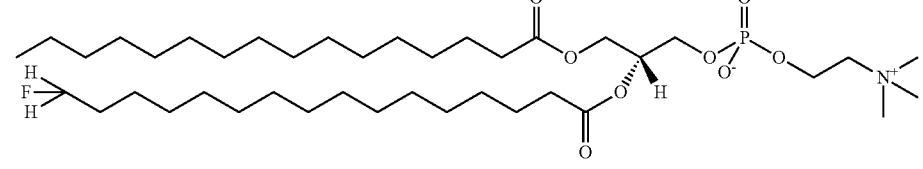

TABLE 2-continued

MATERIALS WITH SATURATED LIPID TAILS

| Class | Structure |
|---|---|
| Exemplary "Clickable" materials | (structures shown) |
| Fatty acids, esters, amides | (structures shown) |

Example 6

Buchi B-290 Spray Drying

PLGA and PAA/PAH in a Cosolvent Mixture

PLGA, a polymer, does not readily disperse in aqueous fluids necessary for intravenous injection. Poly(acrylic acid) (PAA) and poly(allylamine hydrochloride) (PAH) are high molecular weight polymers that confer dispersibility to hydrophobic shells. However, PAA and PAH are not soluble in dichloromethane (DCM), so a cosolvent system was used solubilize PAA and DCM in one homogenous solution. Methanol was chosen to dissolve PAA because it is miscible with DCM. DCM:Methanol was 2:1 by volume.

Spray drying formed a large fraction of hollow particles, however it was discovered that the hollow fraction was formed from PAA and the solid fraction from PLGA. After 2 hours in an aqueous solution, all PAA-based microparticles had dissolved. 0.1 wt % PAH was sufficient to disperse PLGA particles. However, PLGA-PAH particles were all solid.

Lactose—2F Nozzle

Carbohydrate alternatives were investigated should polymer toxicity be a concern. Lactose has been shown to produce hollow microparticles. Secondary coatings or sugar modification may be viable options for preventing lactose microparticles from dissolving in water/blood.

The maximum hollow fraction reached was 16% with this method and the ratio of internal:external diameter (a measure of relative shell thickness) was low, limiting void volume for gas delivery. However, the governing principle of inlet temperature and atomization were determined.

Lactose and Ammonium Carbonate—2F Nozzle

Ammonium carbonate, a volatile agent, was added to the aqueous lactose solution to increase the fraction of hollow particles. Ammonium carbonate is water-soluble and turns to gas at 58° C., creating gaseous pockets that can be entrapped by lactose as water evaporates.

Varying the fraction of lactose and ammonium carbonate as well as temperature and spray parameters produces a wide range of morphologies of hollow lactose microparticles. Large fractions of ammonium carbonate and high aspiration/flow form honeycomb particles which have low densities and high yields. However, honeycomb particles were often greater than 10 microns in diameter and some of the pores reach the outside shell. Generally, a higher weight % of lactose and slower flow rates allowed the ammonia and carbon dioxide gases to coalesce, forming a desired single pore structure. Lower atomization speeds led to particle agglomeration (incomplete separation of particles) during spraying. Agglomerates are sometimes >10 microns.

Lactose, Ammonium Carbonate, and PVA—2F Nozzle

Without sufficient viscosity of a large polymer such as PLGA, gaseous ammonium carbonate blew many lactose particles apart, resulting in debris and large sheets of sugar. Lactose debris decreased gas-carrying capability and yields. Polyvinyl alcohol (PVA) is a water-soluble polymer that increases the viscosity of the solution, allowing ammonium carbonate gas expansion that can be more successfully entrapped during spraying. A 2.0 mm nozzle and 0.7 mm nozzle were both tested.

Addition of PVA significantly reduced the amount of debris and unusable sheets of lactose. However, greater agglomeration during spraying was noted. Nevertheless, this technique produced a good fraction of hollow particles (~50%). Particles manufactured using the 2.0 mm nozzle had a higher yield and higher hollow fraction, but had a size regime too large for injection. Particles manufactured using the 0.7 mm nozzle (below) had a desirable size distribution (<10 microns in diameter). Lactose is a water-soluble sugar, so additional modification of the particles as described herein may be desrieable prior to gas-delivery.

Lactose Octaacetate, Ammonium Carbonate, (DSPC/PVA/NaCl) Emulsion—2F Nozzle

To prevent microparticles from dissolving in the blood stream while still preserving dispersibility, lactose was acetylated using an acid-catalyzed reaction. Briefly, the —OH groups on the lactose backbone are replaced with —OCH3 bonds in acetic acid. Addition of —OCH3 groups prevents the sugar from dissolving in blood which would result in free gas upon injection, while maintaining a fraction of —OH bonds allows the particles to disperse freely in water. Acetylated lactose becomes organo-soluble; mixed organic and aqueous solvent systems require a primary emulsion water/oil emulsion to spray. Lactose octaacetate is dissolved in DCM (oil phase) and water and ammonium carbonate are dissolved in water. The DCM:water ratio is 1:0.1 so when the two fluids are emulsified (by sonication or homogenization), small water droplets form within the oil phase. This primary emulsion can be stabilized by organo- or water-soluble lipids, polymers, or salts. The emulsion was fed to the spray dryer, evaporating and precipitating PLGA from the oil phase and entrapping water droplets. Tuning the emulsion size (through homogenization speed) to the droplet size (through feed rate, nozzle size, and atomization) is necessary for producing hollow particles.

The primary emulsion size to conditions was successfully matched using the 2.0 mm nozzle and produced a small fraction of hollow lactose-octaacetate particles that were enriched to near-100%. Lactose octaacetate is a fully-acetylated lactose molecule and was therefore not dispersible in water. Secondary modifications such as sonication in 1% PVA greatly improve dispersibility. Similar to lactose and ammonium carbonate formulations, the primary emulsion creates debris and bits of carbohydrate that are not formed particles and can be removed. A higher molecular weight sugar such as dextran may reduce debris.

Dextran and Ammonium Carbonate—2F Nozzle

Dextran is a higher molecular weight sugar and may better withstand the expansive force of volatilizing ammonium carbonate. An aqueous solution of dextran and ammonium carbonate was sprayed with the 2F nozzle according to the best manufacturing parameters determined with the lactose/ammonium carbonate particles.

The dextran and ammonium carbonate particles were incredibly fluffy, light, and large. Average particle size was ~50 microns and contained many small pockets of gas. The yield was very high—a 10 g sample produced >500 mL of powder. The higher feed rate (5 mL/min) caused minor agglomeration during spraying, further increasing 'particle' size.

PLGA and Ammonium Carbonate Emulsion (PVA)—2F Nozzle

PLGA, a high molecular weight polymer may act similar to dextran in preventing destruction by ammonium carbonate expansion. PLGA is also commonly used in w/o/w double emulsions and primary emulsion size may be modified by homogenization.

This method produced some hollow particles, but with very thick shells, rendering total gas volume not ideal for therapeutic gas delivery. Ammonium carbonate was discovered to be sufficient to stabilize the primary emulsion and PVA (or other additional stabilizers) are not necessary.

PLGA and Silicone Oil—3F Nozzle

Figure 11:
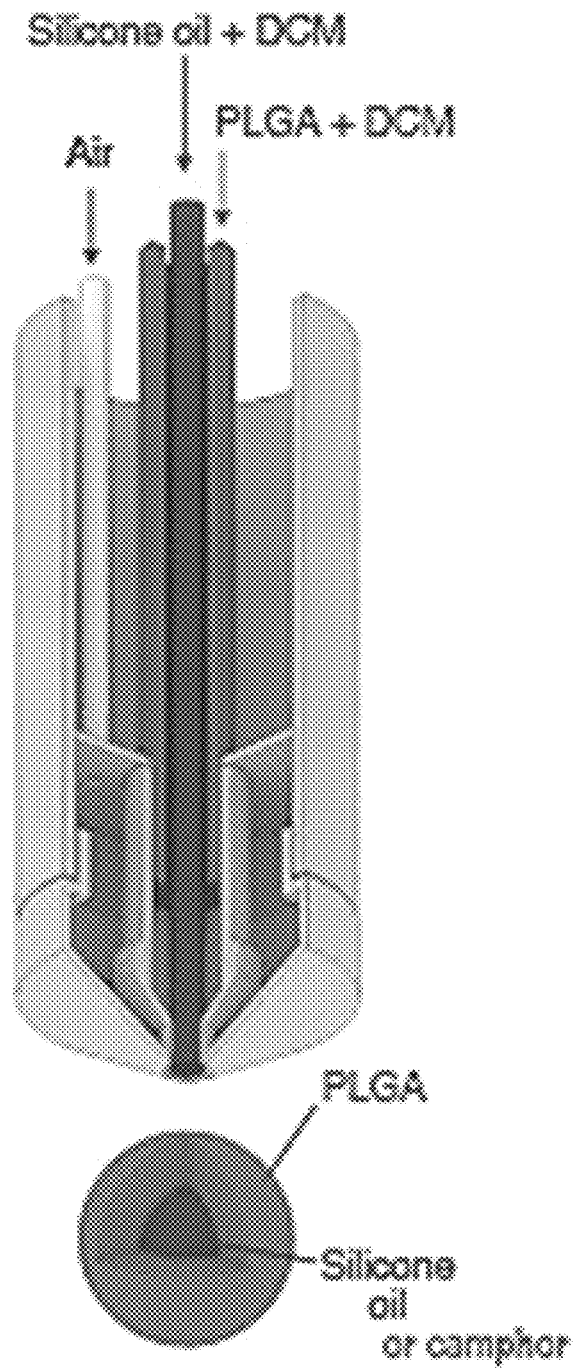
FIG. 11 shows an illustration of a 3F nozzle, a preferable method for microencapsulation of an oil or camphor pore.
Figure 12:
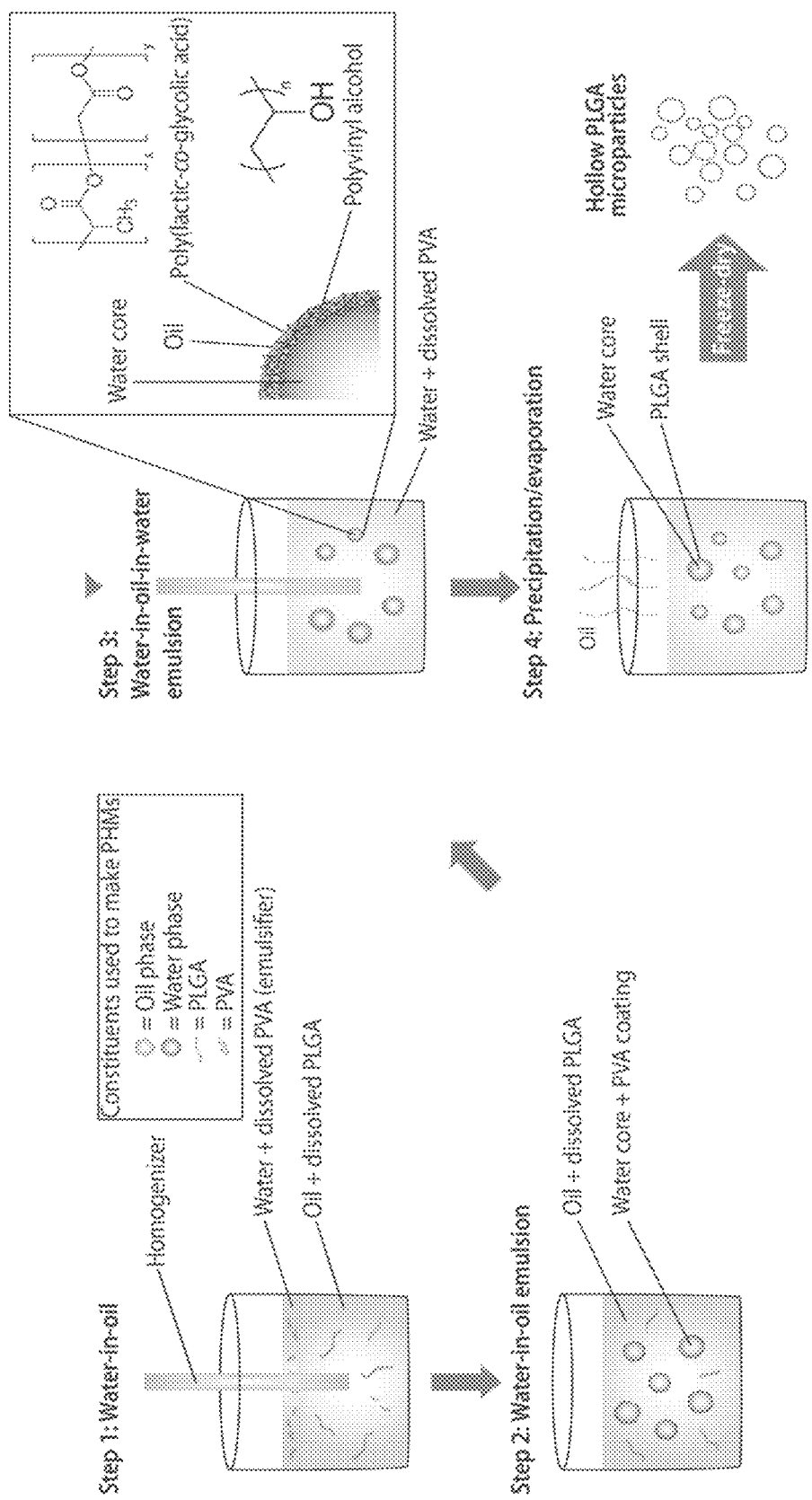
FIG. 12 shows a Water-oil-water (w/o/w) double emulsion technique used to manufacture PHMs. PLGA is dissolved in the oil phase and is added to an emulsifier (polyvinyl alcohol, PVA) dissolved in water (Step 1). When the two phases are homogenized (Step 2), water/PVA droplets form within the oil phase, which contains dissolved PLGA. In Step 3, a PLGA shell is formed around the central droplet by adding the emulsion to a large volume of water under continuous mixing conditions. This forces PLGA (and its oil phase) into a thin layer surrounding the aqueous droplet. The oil is then removed by evaporation (Step 4) and the water core is sublimed by freeze-drying (Step 5), creating dry, hollow core microparticles. These hollow shells are then back-filled with oxygen by simple diffusion of oxygen gas in a sealed container.
Figure 13B:
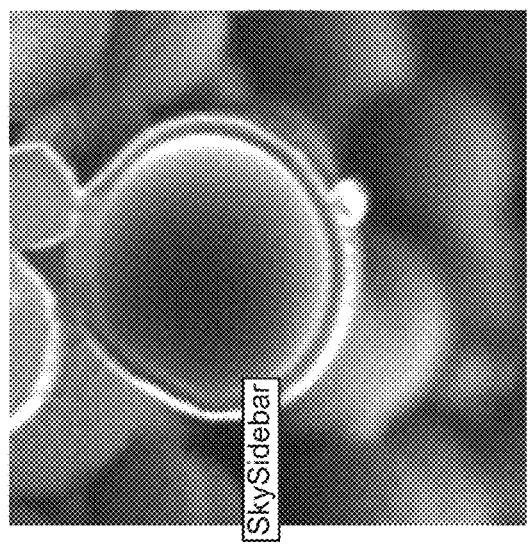
FIGS. 13A-13C show shows PLGA microparticles prepared by a water-oil-water technique and enriched by centrifugation to reach 100% hollow (indicated by a dark center.
Figure 13A:
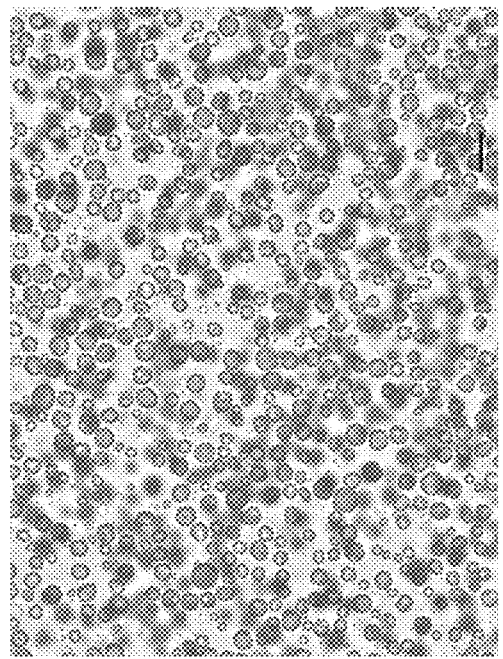
Figure 13C:
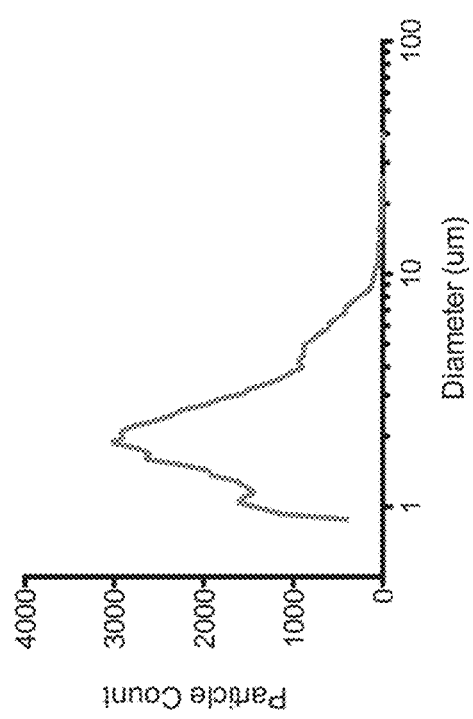
Figure 15:
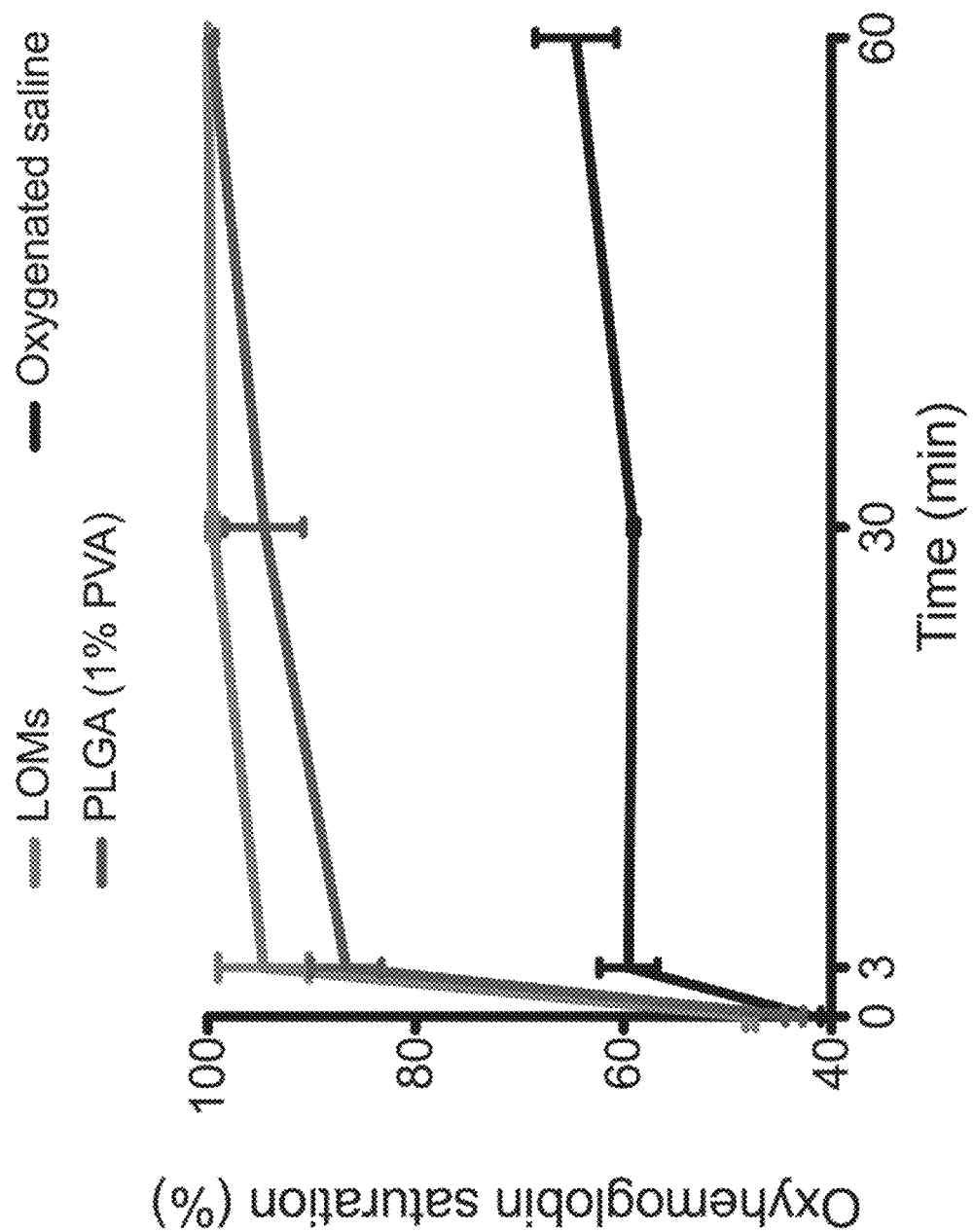
FIG. 15 shows the change in oxyhemoglobin saturation of human blood 3, 30, and 60 minutes after injection of PLGA POMs, LOMs, or oxygenated saline. LOMs delivered 90% of their oxygen payload by 3 minutes and 100% by 30 minutes. POMs delivered 76% of their oxygen payload by 3 minutes and 100% within 60 minutes. Doses of POMs and LOMs were calculated to deliver sufficient oxygen to reach 100% saturation.
Figure 16A:
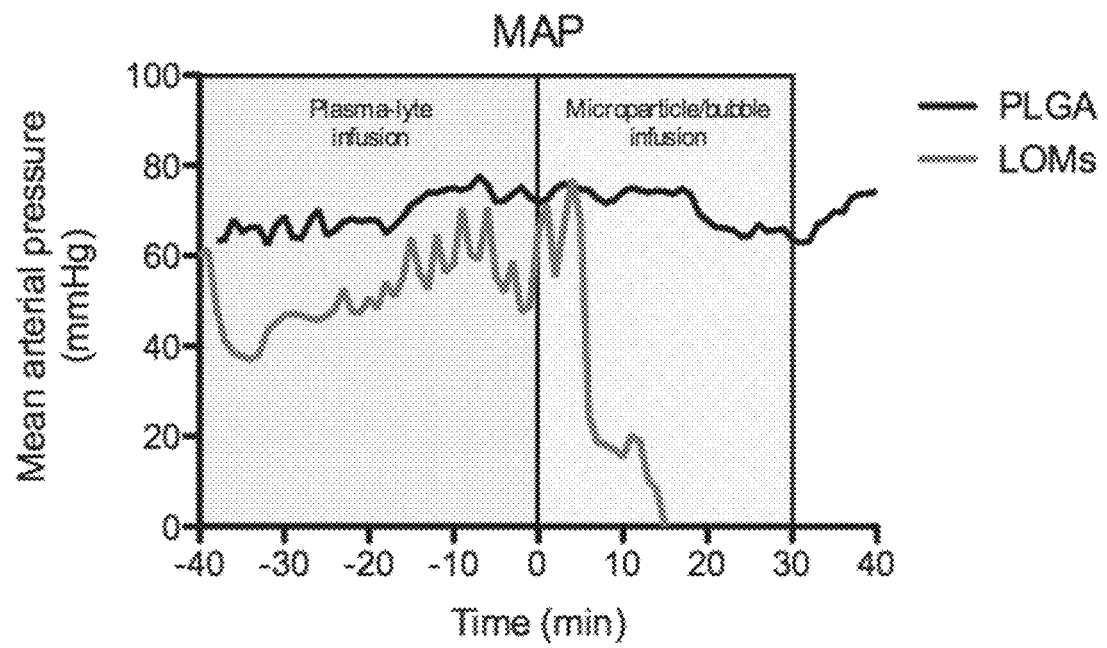
FIGS. 16A-16B show the mean arterial blood pressure (FIG. 16A) and heart rate (FIG. 16B) during an in vivo infusion of hollow PLGA microparticles and LOMs dispersed in plasma-lyte A following a control infusion of plasma-lyte alone. PLGA particles, strong enough to withstand shear during intravenous injection, did not cause any change in mean arterial blood pressure or heart rate during or after injection. Less stable LOMs likely sheared through the narrow catheter necessary for rodent models, causing the animal to suffer severe hypotension and an increase in hear rate before expiring.
Figure 16B:
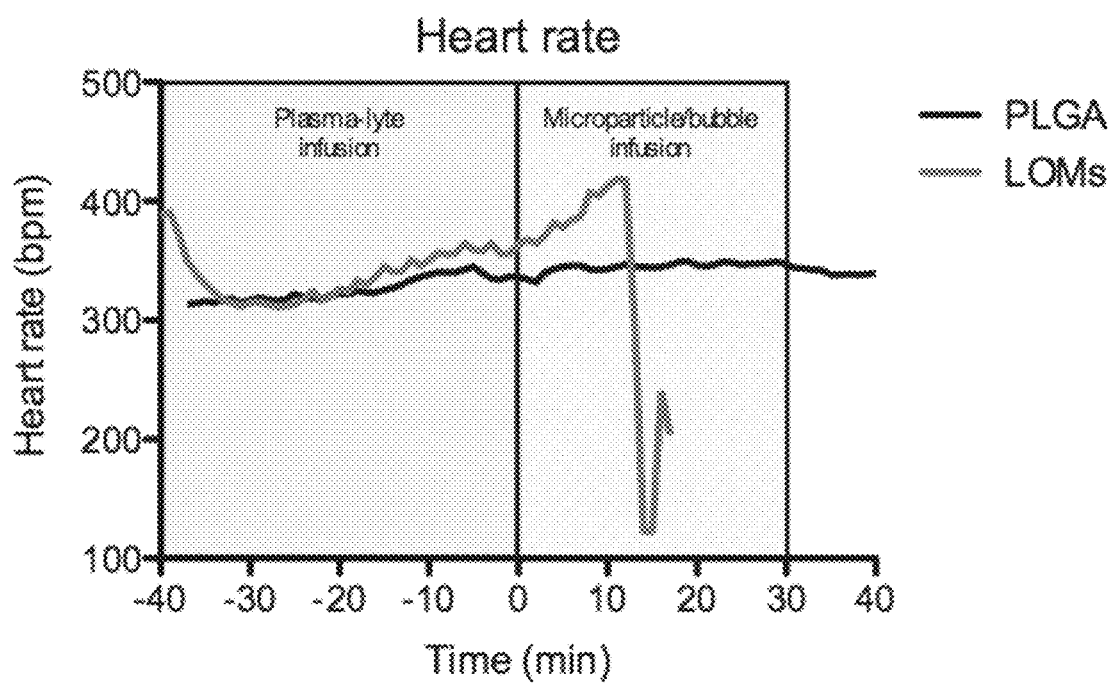

A 3F nozzle (FIG. 11) promotes formation of microcapsules rather than homogenous matrix-like particles by utilizing two concentric feeds for a solvent-shell solution (outer feed) and a solvent-core/poragen (inner feed). For this method, the outer feed contains PLGA dissolved in DCM and the inner feed contains silicone oil dissolved in DCM; the concentric feeds results in PLGA microcapsules with silicone oil cores. Spray-dried particles can be washed in heptane to remove oil, leaving a hollow center.

Preliminary experiments showed a fraction of hollow particles with a depressed donut-like morphology which limits internal volume and therefore oxygen carrying capacity. It is likely that this collapse occurred because the solvent evaporates rapidly while spraying. To obviate this challenge, the drying column temperature was lowered to room temperature and aspiration decreased. Lengthening the total drying time of particles successfully produced a larger fraction of hollow particles. Nearly 100% of silicone oil was removed from internal cores.

PLGA and Camphor—3F Nozzle

The 3 fluid nozzle produced hollow microparticles. Using an organo-soluble volatile agent (similar to ammonium carbonate) will make the process faster by eliminating additional poragen removal steps. Camphor is a commonly used organo-soluble volatile agent that is soluble in DCM.

Camphor slowly sublimes at room temperature when at atmospheric pressure. The slight heat generated by spray-drying combined with slightly lower vapor pressures within the spray dryer caused camphor to volatilize before DCM evaporated and precipitated a formed PLGA shell. Most particles formed were solid.

PLGA and Ammonium Carbonate—3F Nozzle

A 3 fluid nozzle which will allow organic and aqueous phases to be delivered separately, only mixing at the nozzle tip, eliminating the need for an emulsion and matching emulsion size to droplet size.

Preliminary results show formation of a small hollow fraction. Modification of manufacturing parameters should yield a higher fraction of hollow particles. Addition of PVA, PVP, or other dispersing agents to the outer feed solution is expected to obviate the need for additional processing.

Lactose Octaacetate and Ethanol/Methanol—Peclet Numer Spraying

The Peclet number dictates polymer/carbohydrate movement and orientation during spraying. Roughly it is equal to the evaporation of the solvent (E) divided by 8 times the diffusivity (D) of the polymer/carbohydrate within that solvent. Peclet numbers less than one (i.e. slow evaporation and high diffusivity) are known to yield solid microparticles during spraying. Briefly, the polymer orients around the outside of the droplet as it leaves the nozzle due to concentration gradients. When the solvent evaporation is slow and the polymer is able to easily move within the solvent (diffusivity is high), the polymer collapses in on itself and forms a solid particle. Peclet numbers much greater than one (i.e. rapid evaporation and low diffusivity) will 'lock' the polymer when it is oriented on the outside of the droplet, resulting in porous, low-density particles. Lactose octaacetate has low diffusivity in ethanol and methanol and therefore may be spray dried in a hollow conformation when the solvents are evaporated rapidly.

Example 7

Water-in-Oil-in-Water Emulsions—L5MA

PLGA Stabilized by PVA

Our worked has demonstrated that PLGA and water w/o/w provided a high encapsulation efficiency, and therefore a great fraction of hollow particles. Briefly, PLGA was dissolved in an organic solvent and emulsified with water containing an emulsion-stabilizing agent, polyvinyl alcohol (PVA). This primary emulsion was transferred to a large volume of water and homogenized further, causing the PLGA and organic phase to coat water droplets formed in the primary emulsion. The organic solvent was evaporated and the water core lyophilized to create a hollow center (FIG. 12). During homogenization of the secondary emulsion, PLGA particles were coated in PVA which aid dispersibility in water.

This method has produced a high fraction of hollow, thin-shelled PLGA microparticles. They can be concentrated to reach near 100% hollow microparticles. They are composed of a desirable size regime and particle size can be easily tuned using primary and secondary emulsion speeds. PVA, a hydrophilic polymer, was used to stabilize the primary emulsion and to coat the particles during the secondary emulsion. This hydrophilic polymer caused some particles to swell slightly and to fill with fluid. The swelling can be titrated by adjusting the fraction of PVA on and within the shell.

PLGA Stabilized by F-127

The w/o/w double emulsion technique above was modified to utilize an amphiphilic block copolymer, F-127. Reducing the hydrophilicity of the stabilizing agent will lower the drive for water to enter the core of the particle, allowing them to stay gas-filled for longer periods of time (such as in a syringe). All manufacturing and processing parameters remained the same as above. 1% PVA was still utilized in the secondary emulsion to coat the particles and confer dispersibility.

F-127 successfully stabilized the primary emulsion in a beaker, but when used in the w/o/w technique, it likely did not encapsulate water. Oil-phase only microparticles were produced containing DCM, F-127, and PLGA. Shortly after manufacture, the PLGA and F-127 began to separate forming a doublet. However, F-127 is water-soluble and began to dissolve. As DCM evaporated and F-127 dissolved into the water phase, particles obtained a bowl-shape and did not contain a water core under these conditions.

Example 8

In Vitro and In Vivo Characterization of PLGA Particles Manufactured by a w/o/w Emulsion Hollow PLGA Microparticle In Vitro Characterization Current methods produce a population of ~50% hollow particles (indicated by a dark central pore under light microscopy; FIG. 13B) that can be enriched by centrifugation to 100% hollow (FIG. 13A). These microparticles have a thin shell (~300 nm, center) and a very desirable size distribution (FIG. 13C). An average particle size of 4 μm provides substantial void volume for gas while allowing particles to easily pass through capillaries. Homogenization speed was identified during the primary and secondary emulsions as a key parameter in determining shell thickness and particle size, a phenomenon consistent with literature.

A tap densitometer packs down particles in powder form to determine the density of hollow microparticles. The density of hollow PLGA particles was compared to the density of a similar size distribution of solid PLGA microparticles and the difference in densities used to calculate volume fraction of gas. The average density of hollow PLGA microparticles was found to be 0.134 g/mL (±0.024, SD) and the average fraction of oxygen found to be 71.4% (±5.13, SD). Rheological testing determined that a 55 vol % slurry demonstrates an ideal rheological profile for injection into the blood stream. It was noted that hollow particles filled with water after about 10 minutes causing the slurry viscosity to increase over time (FIG. 14A). Cross-sectional scanning electron microscopy revealed a large web of PVA in the internal core of some particles (FIG. 14B); fluid-filling is likely caused due to the hydrophilicity of PVA. As fluid volume enters the particle core, the fluid phase of the slurry decreases and the slurry turns to paste within 45 minutes. Alternative polymers and lipids have been tested for their ability to stabilize the primary emulsion without incorporating into the core. Balancing PLGA wt % and processing parameters produces particles of varying shell thicknesses, strong enough to withstand negative pressure during lyophilization as described in more detail below.

Hollow PLGA microparticles were passively filled with oxygen gas, diluted to 55 volume % oxygen, and injected into deoxygenated human blood with gentle mixing. The change in oxyhemoglobin saturation of blood was measured by a blood glass analyzer at 3, 30, and 60 minutes post-injection. PLGA particles released 76% of their oxygen payload by the first time point (3 min) and 100% of their oxygen payload by 60 minutes (FIG. 15).

Preliminary in vivo experiments were completed in anesthetized rats under normoxic conditions to determine the hemodynamic effects of injecting hollow PLGA microparticles compared to injecting an equivalent number of LOMs. Animals demonstrated no adverse effects and importantly, no change in arterial blood pressure or heart rate after an injection over 30 minutes (FIG. 16). Upon necropsy, a sample of blood was showed intact particles flowing freely under the microscope.

Example 9

Honeycomb Microparticles for Gas Delivery

Methods: Synthesis; General Preparation of Porous Microparticles.

Honeycomb microparticles have been fabricated extensively in the literature using a variety of techniques. (Rosca, I. D., Watari, F. & Uo, M. Microparticle formation and its mechanism in single and double emulsion solvent evaporation. *Journal of Controlled Release* 99, 271-280(2004), Straub, J. A. et al. Porous PLGA microparticles: AI-700, an intravenously administered ultrasound contrast agent for use in echocardiography. *Journal of Controlled Release* 108, 21-32 (2005), Kim, M. R., Lee, S., Park, J.-K. & Cho, K. Y. Golf ball-shaped PLGA microparticles with internal pores fabricated by simple O/W emulsion. *Chem. Commun.* 46, 7433 (2010), Duncanson, W. J. et al. Monodisperse Gas-Filled Microparticles from Reactions in Double Emulsions. *Langmuir* 28, 6742-6745 (2012), Yu, X. et al. Biodegradable Polymer Microcapsules Fabrication through a Template-FreeApproach. *Langmuir* 27, 10265-10273 2011), Schugens, C. H. et al. Effect of the emulsion stability on the morphology and porosity of semicrystalline poly 1-lactide microparticles prepared by w/o/w double emulsionevaporation. *Journal of Controlled Release* 32, 161-176, Crotts, G. & Park, T. G. Preparation of porous and nonporous biodegradable polymeric hollow microspheres. *Journal of Controlled Release* 35, 93-105.)

Here we utilized the double emulsion evaporation/precipitation method. However, other methods may be used. PLGA was weighed out, placed into a scintillation vial, and dissolved by addition of methylene chloride to the desired concentration (typically 5 wt/vol %). This solution was then poured into an aqueous solution containing PVA (0.1-2 wt/vol %). Sometimes this solution contains a salt such as sodium chloride or ammonium carbonate (0.5 wt %). The water to organic phase ratio varies from 0.05 to 0.5. The water-in-oil emulsion was subsequently sonified at room temperature and immediately poured into a second aqueous solution containing PVA (and sometimes a salt), and homogenized for an additional five minutes. Particles were allowed to harden by the evaporation/precipitation method. Once hardened, particles were collected by centrifugation (3500×g for five minutes), washed five times with distilled water, and freeze dried to yield a white powder.

Screening Design of Experiments (sDOE)

Figure 17:
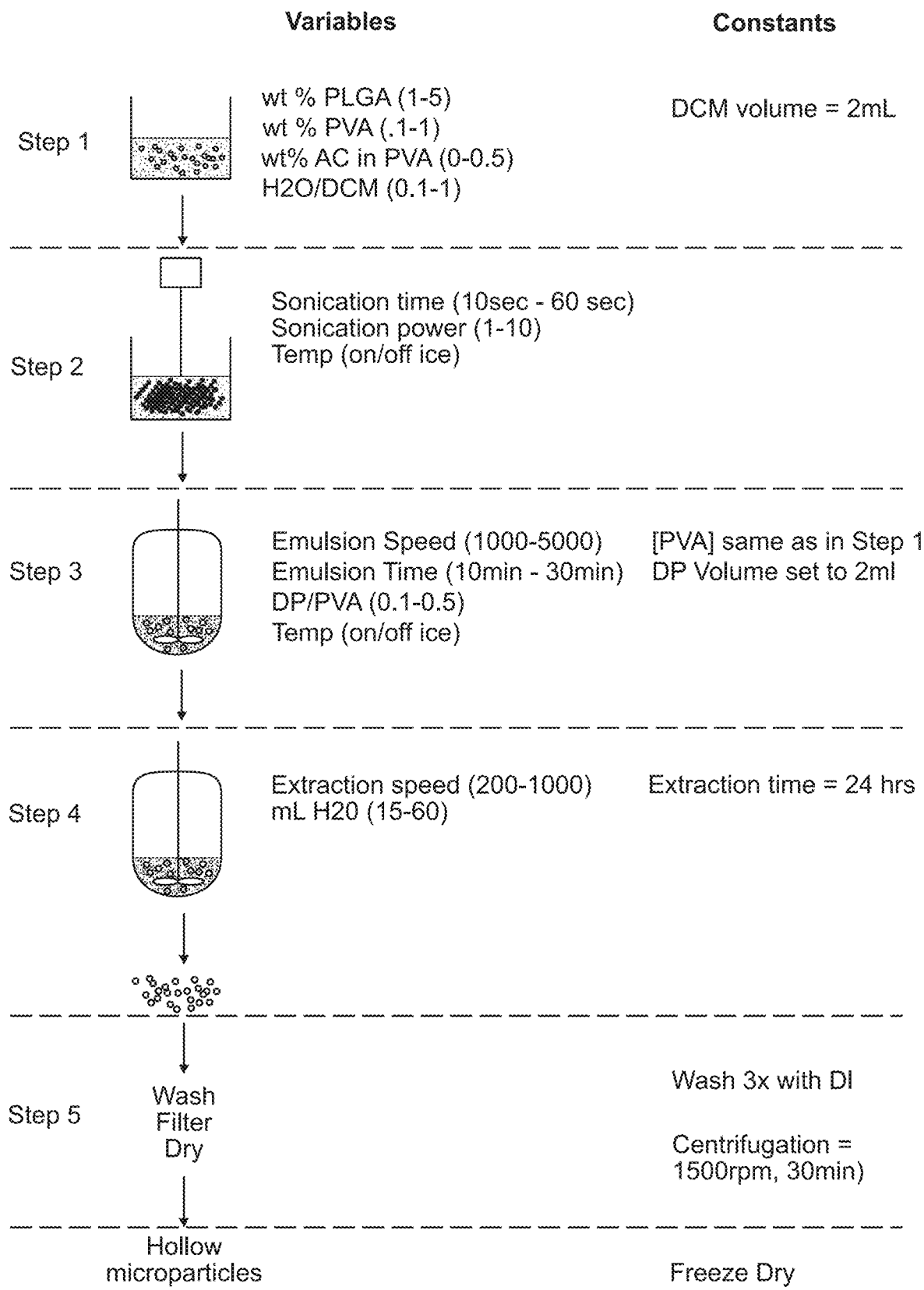
FIG. 17. Schematic representation of manufacturing process for preparation of PLGA-based porous microparticles.

A two-level screening design of experiments (sDOE) was used to determine the effect of varying the processing parameters on two response variables: percent honeycomb and particle diameter. Parameters tested included: concentration of PLGA, PVA, and salt, aqueous to organic ratio, primary emulsion time, power, and temperature, secondary emulsion speed, temperature, and time, ratio of dispersed phase to aqueous phase, and extraction volume. The boundary conditions employed for each variable in the sDOE were selected based on literature reports. A list of the parameters tested and their values, as well as a schematic of the work flow, is shown in Table 3 and FIG. 17, respectively.

TABLE 3

| wt % PLGA | wt % PVA | wt % Ammonium carbonate | H20/DCM | Sonication Time (sec) | Sonication Power | Sonication Temp | Emulsion Speed (rpm) | Emulsion Time (min) | DP/PVA | Emulsion Temp | Extraction Speed (rpm) | Extraction volume (mL) |
|---|---|---|---|---|---|---|---|---|---|---|---|---|
| 5 | 1 | 0 | 0.1 | 10 | 5 | Ice | 5000 | 30 | 0.5 | No Ice | 200 | 60 |
| 5 | 1 | 0 | 1 | 50 | 5 | Ice | 5000 | 30 | 0.1 | Ice | 1000 | 15 |
| 5 | 0.1 | 0 | 1 | 60 | 10 | Ice | 1000 | 30 | 0.5 | Ice | 200 | 60 |
| 1 | 1 | 0 | 0.1 | 10 | 10 | Ice | 5000 | 10 | 0.5 | Ice | 1000 | 60 |
| 1 | 1 | 0 | 0.1 | 60 | 5 | No ice | 1000 | 30 | 0.1 | No Ice | 200 | 60 |
| 1 | 0.1 | 0.5 | 1 | 10 | 5 | Ice | 5000 | 30 | 0.5 | No Ice | 200 | 15 |
| 5 | 0.1 | 0 | 0.1 | 60 | 5 | No ice | 5000 | 10 | 0.5 | Ice | 200 | 15 |
| 1 | 0.1 | 0.5 | 0.1 | 10 | 10 | No ice | 1000 | 10 | 0.5 | No Ice | 200 | 60 |
| 5 | 1 | 0.5 | 1 | 60 | 10 | No ice | 5000 | 30 | 0.5 | No Ice | 1000 | 60 |
| 5 | 1 | 0.5 | 0.1 | 60 | 5 | Ice | 1000 | 10 | 0.5 | No Ice | 1000 | 15 |
| 5 | 0.1 | 0 | 1 | 10 | 5 | No ice | 5000 | 10 | 0.1 | No Ice | 1000 | 60 |
| 5 | 0.1 | 0 | 0.1 | 10 | 10 | Ice | 1000 | 30 | 0.1 | No Ice | 1000 | 15 |
| 5 | 0.1 | 0.5 | 0.1 | 10 | 5 | No ice | 1000 | 30 | 0.5 | Ice | 1000 | 60 |
| 5 | 1 | 0.5 | 1 | 10 | 5 | Ice | 1000 | 10 | 0.1 | Ice | 200 | 60 |
| 1 | 1 | 0.5 | 0.1 | 10 | 5 | No ice | 5000 | 10 | 0.1 | No Ice | 1000 | 15 |
| 1 | 1 | 0.5 | 1 | 60 | 5 | No ice | 5000 | 10 | 0.5 | Ice | 200 | 60 |
| 5 | 1 | 0 | 0.1 | 60 | 10 | No ice | 1000 | 10 | 0.1 | Ice | 1000 | 60 |
| 5 | 0.1 | 0.5 | 0.1 | 60 | 10 | Ice | 5000 | 10 | 0.1 | No Ice | 200 | 60 |
| 5 | 1 | 0.5 | 0.1 | 10 | 10 | No ice | 5000 | 30 | 0.1 | Ice | 200 | 15 |
| 5 | 1 | 0 | 1 | 10 | 10 | No ice | 1000 | 10 | 0.5 | No Ice | 200 | 15 |
| 5 | 0.1 | 0.5 | 1 | 10 | 10 | Ice | 5000 | 10 | 0.5 | Ice | 1000 | 15 |
| 1 | 1 | 0.5 | 0.1 | 60 | 10 | Ice | 1000 | 30 | 0.5 | Ice | 200 | 15 |
| 1 | 1 | 0 | 1 | 60 | 10 | Ice | 5000 | 10 | 0.1 | No Ice | 200 | 15 |
| 1 | 0.1 | 0 | 0.1 | 60 | 10 | No ice | 5000 | 30 | 0.5 | No Ice | 1000 | 15 |
| 1 | 0.1 | 0 | 1 | 10 | 10 | No ice | 5000 | 30 | 0.1 | Ice | 200 | 60 |
| 1 | 0.1 | 0.5 | 0.1 | 60 | 5 | Ice | 5000 | 30 | 0.1 | Ice | 1000 | 60 |
| 1 | 0.1 | 0 | 1 | 60 | 5 | Ice | 1000 | 10 | 0.5 | No Ice | 1000 | 60 |
| 1 | 1 | 0 | 1 | 10 | 5 | No ice | 1000 | 30 | 0.5 | Ice | 1000 | 15 |
| 1 | 1 | 0.5 | 1 | 10 | 10 | Ice | 1000 | 30 | 0.1 | No Ice | 1000 | 60 |
| 1 | 0.1 | 0.5 | 1 | 50 | 10 | No ice | 1000 | 10 | 0.1 | Ice | 1000 | 15 |
| 1 | 0.1 | 0 | 0.1 | 10 | 5 | Ice | 1000 | 10 | 0.1 | Ice | 200 | 15 |
| 3 | 0.55 | 0.25 | 0.55 | 35 | 7.5 | Ice | 3000 | 20 | 0.3 | Ice | 600 | 37.5 |
| 5 | 0.1 | 0.5 | 1 | 60 | 5 | No ice | 1000 | 30 | 0.1 | No Ice | 200 | 15 |

Size Analysis

Particles were diluted with ultra pure water (resistivity of 18 MΩ) to a slurry containing 10% gas (vol/vol). Photomicrographs of LOM formulations were obtained using light microscopy (Olympus IX71, Q Imaging Retiga 2000R equipped with MetaMorph® Microscopy Automation & Image Analysis Software) and analyzed using ImageJ software. Images were processed by setting the scale and manually determining particle diameter. The average microbubble diameter for each formulation was determined by averaging at least 100 individual particles.

Results:

Determination of Percent Porous Microparticles and Particle Diameter

The overall goal of the sDOE was to identify the key processing parameters needed to manufacture large quantities of porous polymer microparticles with the appropriate particle size distribution. 8 of the 33 formulations tested had greater than 40% yield, with the remainder being a combination of microparticles with uniformly hollow and solid cores, respectively. In addition, all particles manufactured had particle sizes less than 15 micron and all but 1 had diameters less than 10 microns. The results of the sDOE are shown in Table 3.

Effect of Processing Parameters on Porous Particle Formation

The sDOE showed that the number of porous microparticles was dependent on the concentration of PLGA and salt in the primary emulsion, respectively, as well as the secondary emulsion speed (FIG. 18). More specifically, it was shown that higher concentrations of PLGA favored the formation of honeycomb-like microparticles. This result stems from the fact that high PLGA concentrations increase solution viscosity. This serves two purposes: (1) stabilization of the primary emulsion and (2) inhibition of entrapped bubble coalescence during solvent evaporation and polymer precipitation. Second, high concentrations of salt, in both aqueous phases, was also found to favor honeycomb formation. Addition of salts to the aqueous phases of a w/o/w emulsion serves to balance the osmotic pressure gradients across the oil phase and to counteract Ostwald ripening. (Gao, F., Su, Z.-G., Wang, P. & Ma, G.-H. Double Emulsion Templated Microcapsules with Single Hollow Cavities and Thickness-Controllable Shells. *Langmuir* 25, 3832-3838 (2009).) This stabilizes the double emulsion while solvent evaporation occurs, and allows the PLGA polymer to precipitate and entrap the water droplets within its interior. Finally, the secondary emulsion speed was shown to negatively influence honeycomb particle formation. Slower secondary emulsion speeds enable a larger number of water droplets to be encapsulated within the particles interior, whereas faster speeds were shown to lead to the formation of microparticles with uniformly hollow and solid cores, respectively. (Rosca, I. D., Watari, F. & Uo, M. Microparticle formation and its mechanism in single and double emulsion solvent evaporation. *Journal of Controlled Release* 99, 271-280(2004).)

Figure 18A:
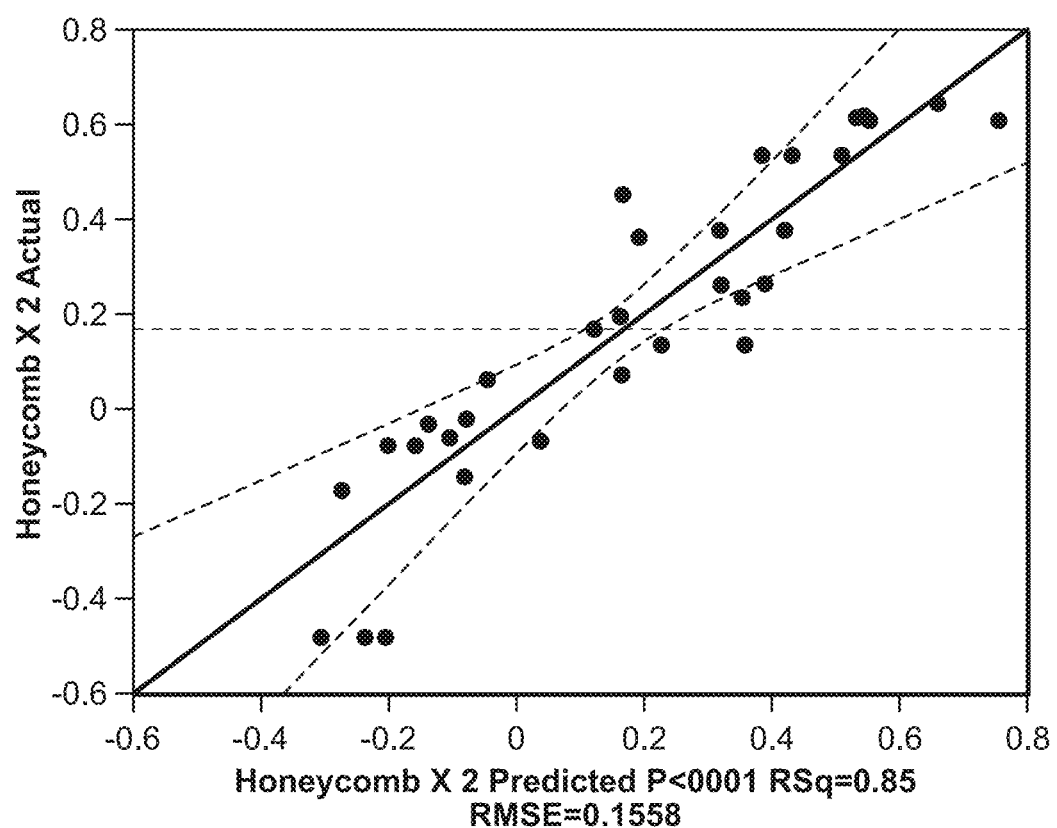
FIGS. 18A-18B. Evaluation of the percent yield model.
Figure 18B:
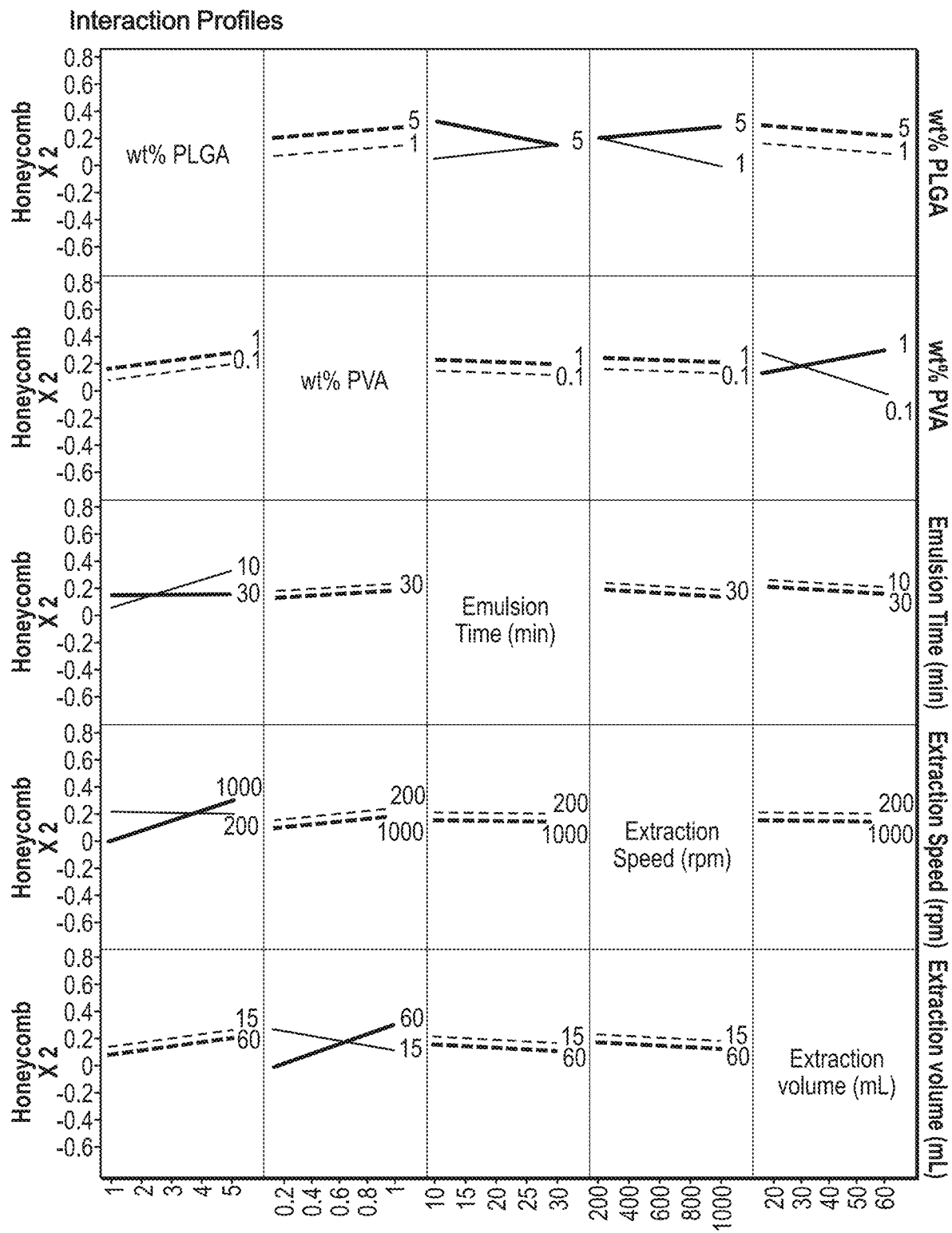

In addition, the sDOE identified three secondary interaction terms that also effected the yield of honeycomb particles (FIGS. 18A and 18B). For example, the interaction term PLGA*Emulsion Time revealed that emulsification for 30 min, regardless of PLGA concentration, yielded the same amount of honeycomb particles. However, emulsification for only 10 min, at high PLGA concentrations, nearly doubled the yield of honeycomb particles. It is hypothesized that extensive homogenization leads to destabilization of the emulsion, which decreases the percent yield of hollow microparticles. Similarly, the PLGA*Extraction Speed interaction term revealed that stirring at 200 rpm overnight under these conditions had almost no effect on the percent yield of honeycomb particles, regardless of PLGA concentration. However, extraction at 1000 rpm increased the yield of honeycomb particles when high concentrations of PLGA were used. We hypothesize that higher extraction speeds increased the rate of solvent evaporation and hence the rate of polymer precipitation. However, the increased rate of stirring can also lead to burst escape of the internal water droplets. This was evident from lower yield of honeycomb particles when lower concentrations of PLGA were used at the high extraction speeds (i.e. low PLGA concentration has a lower solution viscosity and was not able to stabilize the internal phase under high stir conditions). Finally, the PVA*Extraction Volume term revealed that high yields were favored at high PVA concentrations and high extraction volumes. Higher concentration of PVA act to stabilize the oil phase during solidification of the particles (i.e. prevents oil droplets from coalescing), while the higher extraction volume increases PLGA precipitation (minimizes time for droplet coalescence and rapidly traps the honeycomb structure in place).

Effect of Processing Parameters on Porous Particle Diameters

Figure 19A:
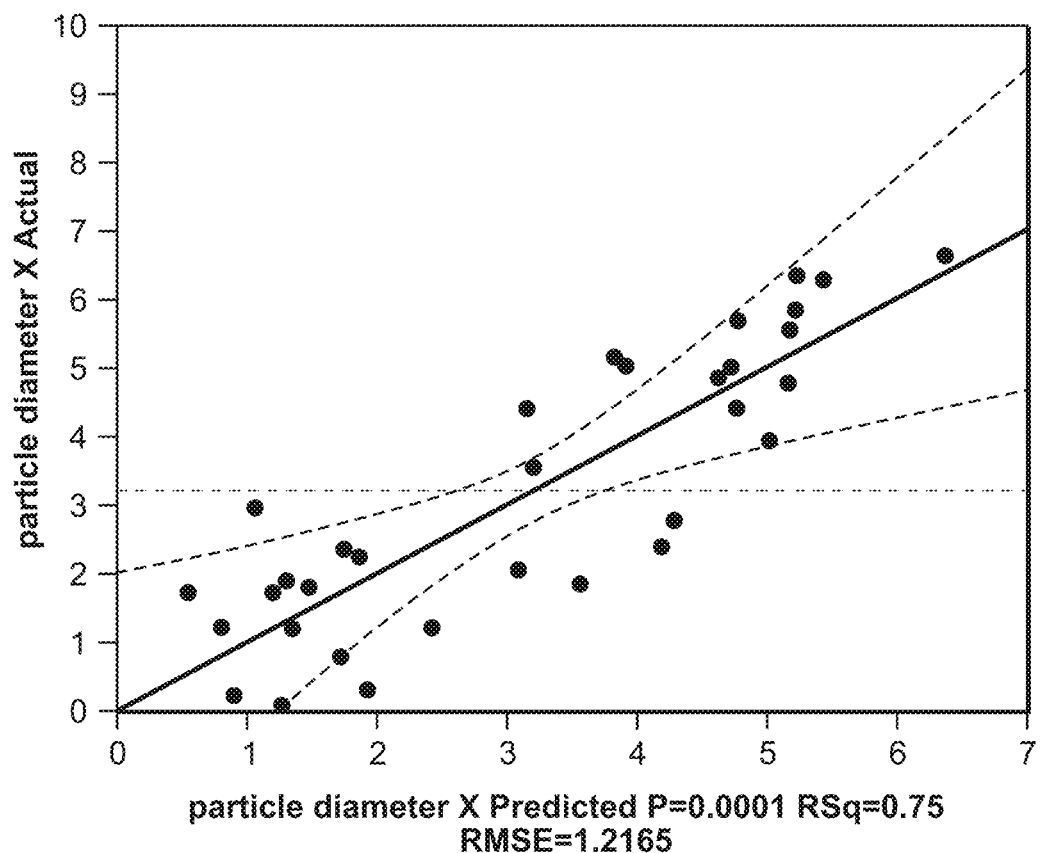
FIGS. 19A-19B. Evaluation of the size model.
Figure 19B:
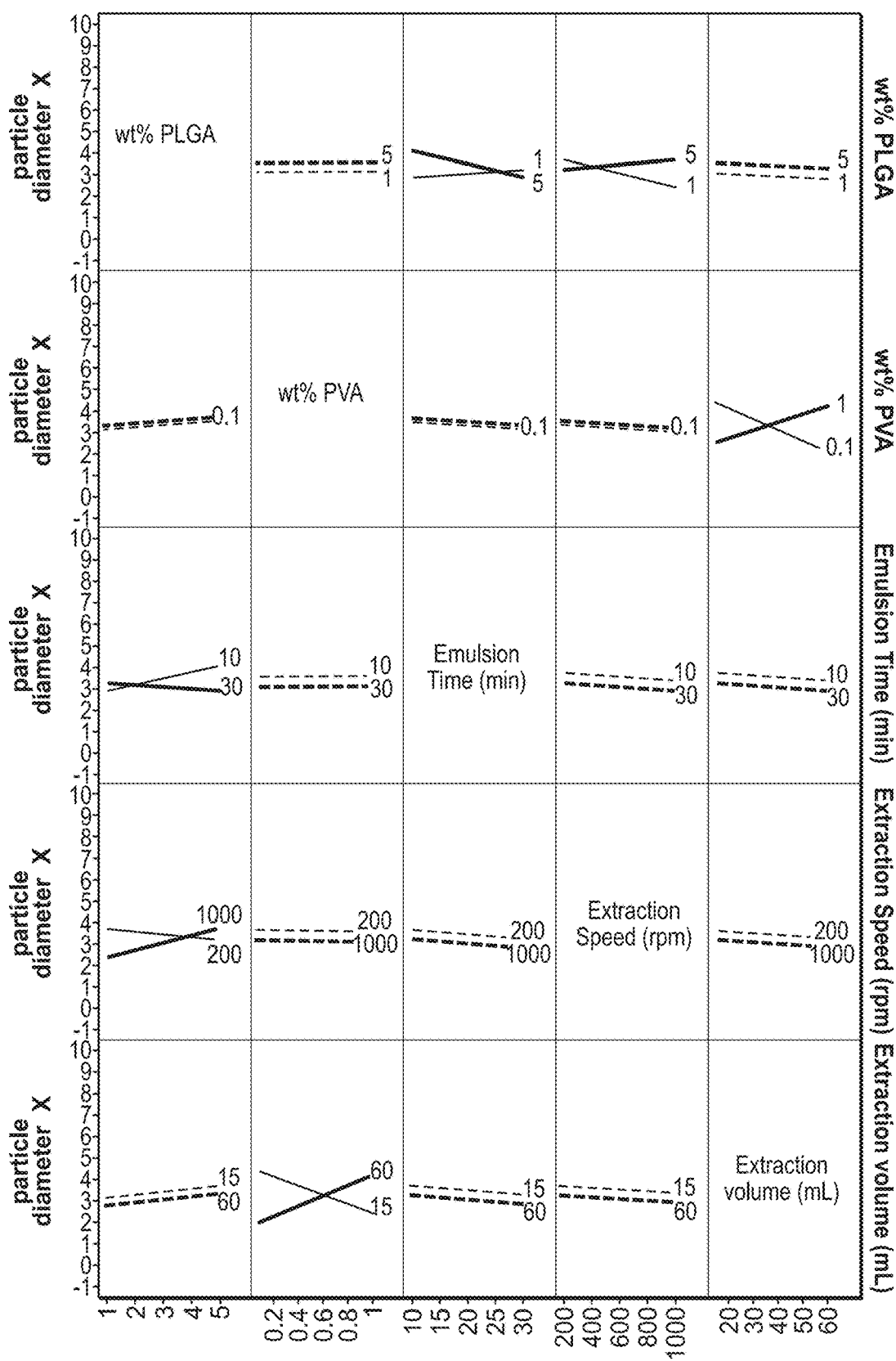

The sDOE showed that the diameter of microparticles was dependent on the concentration of salt and the emulsion speed. As mentioned above, the salt concentration contributes to stabilizing the primary emulsion and enables high encapsulation efficiencies (FIG. 19). Microparticles with large amounts of encapsulated water droplets were incompressible, which limits particle shrinkage during solvent evaporation (i.e. increases particle size); whereas particles with lower amounts of entrapped water droplets can experience up to 30% volume loss during the solvent evaporation process (i.e decreased particle size relative to the original emulsion size). The effects of the secondary emulsion speed on particle size is known, with higher speeds resulting in smaller particles (assuming a constant solution viscosity). (Rosca, I. D., Watari, F. & Uo, M. Microparticle formation and its mechanism in single and double emulsion solvent evaporation. *Journal of Controlled Release* 99, 271-280 (2004).)

Prediction of the Optimal Formulation

Figure 20:
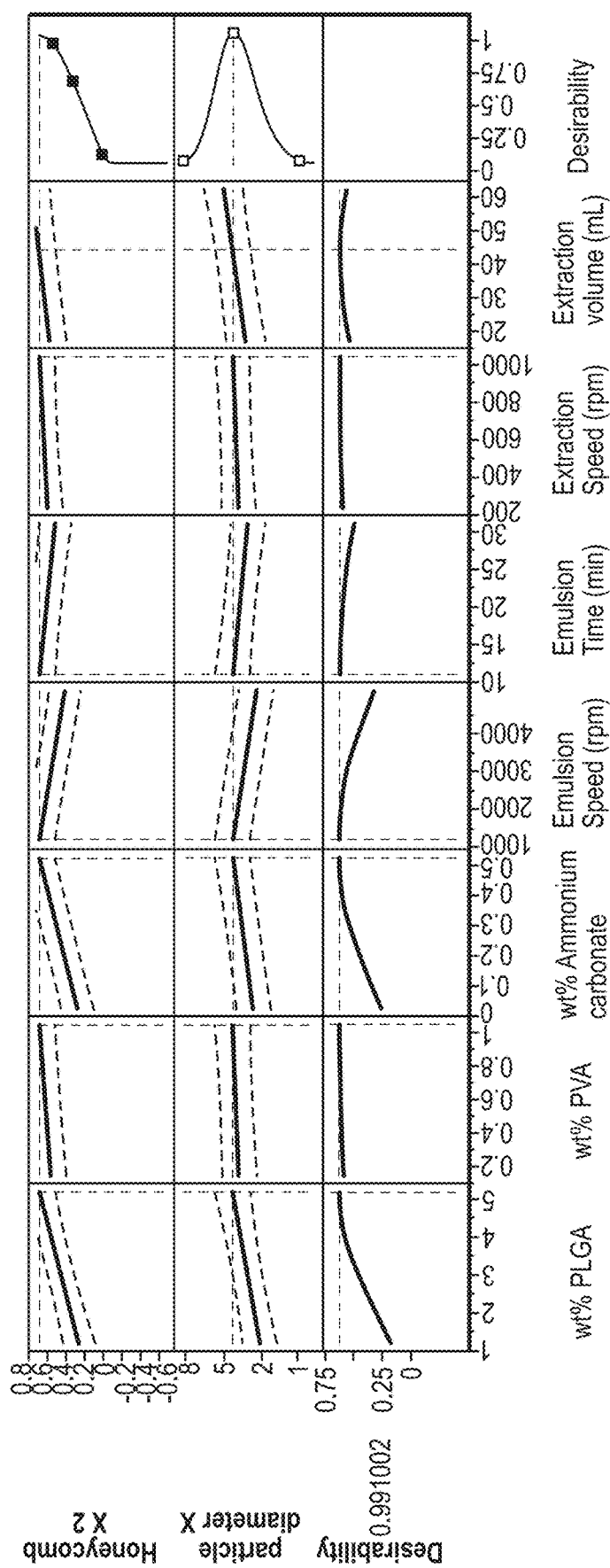
FIG. 20. Identification of the optimal processing parameters using the reduced model through JMPs prediction profiler platform. The sDOE predicted the following conditions: 5 wt % PLGA, 1 wt % PVA, 0.5 wt % salt, secondary emulsion speed of 5000 rpm, secondary emulsification time of 10 minutes, an extraction speed of 1000 rpm, and an extraction volume of 50 mL (i.e. dilution factor of between 3.5-13.5).

To predict the optimal formulation, we utilized the Prediction Profiler function within the Least Squares Fit platform (FIG. 20). The desirability parameters for both percent honeycomb and particle size maximize and match target with an importance value of 1. The model predicted that microparticles manufactured according to the following parameters (5 wt % PLGA, 1 wt % PVA, 0.5 wt % salt, secondary emulsion speed of 5000 rpm and time of 10 minutes, extraction speed of 1000 rpm, and an extraction volume of 42 mL) would produced honeycomb microparticles with a yield of 100% and an average diameter of 10 microns.

Model Validation

The power of the prediction profiler is that it allows one to predict the response variables when the factor parameters are varied. To test the validity of our model we utilized the prediction profiler to determine the percent yield and particle diameter for particles manufactured using the following conditions: 5 wt % PLGA, 1 wt % PVA, 0.5 wt % salt, secondary emulsion speed and time of 15000 rpm and 10 minutes, extraction speed of 1000 rpm, and an extraction volume of 45 mL. The model predicted a yield of 0.625 and an average particle diameter of 5.25, which when back transformed equates to approximately 65% and 5.79 microns, respectively. Actual measured values were 68.7% yield and a mean particle size of approximately 5.14 microns (FIGS. 21A-C).

Large Scale Manufacturing of Porous Polymer Microparticles (1-10 Grams)

Large scale manufacturing of porous polymer microparticles was accomplished using a combination of sonication and a lab scale homogenizer (Silverson L5MA). In general, the key parameters identified during the small scale experiments (i.e. from the sDOE) were used as guides to facilitate the scale-up procedure.

Optimization of Large Scale Manufacturing

In order for porous polymer microparticles to be effective vehicles for intravenous oxygen delivery, they must encapsulate high volumes of gas within their interiors. One of the challenges with the large scale manufacturing of honeycomb polymer particles is gas loss due to defects in the particles shell. These defects may be restricted to the shell surface, in which case gas can still be stored and delivered from the interior gas pockets; or they may be interconnected throughout the particle's interior, resulting in particles with poor gas encapsulation efficiencies (FIG. 21A, 21B).

The amount of water used to generate the primary emulsion (W/O) and the rate of precipitation are known to influence microparticle surface morphology with higher aqueous/organic ratios and slow solidification times leading to surface defects. (Yeo, Y. & Park, K. Control of Encapsulation Efficiency and Initial Burst in Polymeric Microparticle Systems. *Arch Pharm Res* 27, 1-12 (2004).) In order to maximize the gas carrying capacity of porous polymer microparticles we evaluated the effect of varying the aqueous/organic ratio and the precipitation rate. The specific parameters used for the fabrication are shown in Table 4. Specifically, aqueous/organic ratios of 0.5, 0.225, and 0.1 or 0.5, 0.225, and 0.05 were fabricated using a slow (DF=11) and fast precipitation rate (DF=61), respectively.

aqueous/organic ratios encapsulate fewer droplets which prevents coalescence into a uniform core. We anticipate that rapid precipitation with lower aqueous/organic ratios will substantially reduce the particle's density without introducing significant surface defects. Increasing the aqueous/organic ratio in conjunction with rapid precipitation maybe a viable approach to fabricate uniformly hollow microparticles in high yields.

TABLE 5

Tapped density measurements for manufactured honeycomb microparticles.

| Label | Formulation | Density (g/mL) |
|---|---|---|
| A | 43-649-50-1 | 0.072 |
| B | 43-649-63-4 | TBD |
| C | 43-649-50-2 | TBD |
| D | 43-649-63-1 | TBD |
| E | 43-649-63-2 | TBD |
| F | 43-649-63-3 | TBD |

TBD = To be determined

Oxygen Transfer Kinetics

Figure 22:
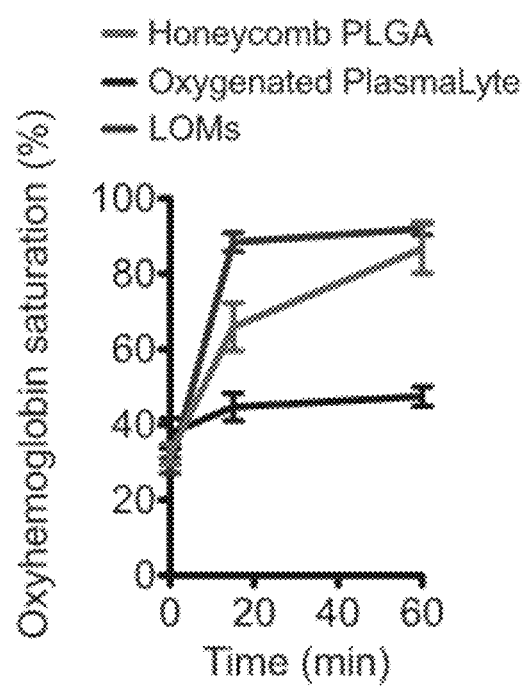
FIG. 22 A graph depicting optical photomicrographs of honeycomb microparticles manufactured from various processing conditions. Microparticles were fabricated with varying aqueous/organic ratios and a slow precipitation rate aqueous/organic ratio=0.5; aqueous/organic ratio=0.225; aqueous/organic ratio=0.1). Microparticles were fabricated with varying aqueous/organic ratios and a fast precipitation rate aqueous/organic ratio=0.5; aqueous/organic ratio=0.225; aqueous/organic ratio=0.05.

The effect of varying the aqueous/organic ratio and the precipitation rate on oxygen transfer kinetics was evaluated by (1) passively diffusing oxygen gas into the particle core, (2) adding said particles to deoxygenated blood of known oxygen saturation, and (3) measuring the increase in oxygen saturation at 0, 15, and 60 minutes after administration. The results indicate that honeycomb particles readily transfer about 70% of their oxygen payload to deoxygenated blood within 15 minutes and greater than 90% within 60 minutes (FIG. 22 n=3).

TABLE 4

Experimental conditions for optimization of microparticles for oxygen delivery.

| Label | Formulation | Sonication Power | Sonication Time (s) | PVA in W1 (wt %) | NaCl in W1 (wt %) | Water/DCM | 2 speed (rpm) | 2 time (min) | PVA in W2 (wt %) | NaCl in W2 (wt %) | Volume of W2 (mL) | DF of W2 | Final Volume (mL) |
|---|---|---|---|---|---|---|---|---|---|---|---|---|---|
| A | 43-649-50-1 | Max | 10 | 0 | 0.75 | 0.5 | 4000 | 5 | 1 | 0.5 | 200 | 1 | 200 |
| B | 43-649-63-4 | Max | 10 | 0 | 0.75 | 0.225 | 4000 | 5 | 1 | 0.5 | 200 | 1 | 200 |
| C | 43-649-50-2 | Max | 10 | 0 | 0.75 | 0.1 | 4000 | 5 | 1 | 0.5 | 200 | 1 | 200 |
| D | 43-649-63-1 | Max | 10 | 0 | 0.75 | 0.5 | 4000 | 5 | 1 | 0.5 | 200 | 6 | 1200 |
| E | 43-649-63-2 | Max | 10 | 0 | 0.75 | 0.05 | 4000 | 5 | 1 | 0.5 | 200 | 6 | 1200 |
| F | 43-649-63-3 | Max | 10 | 0 | 0.75 | 0.225 | 4000 | 5 | 1 | 0.5 | 200 | 6 | 1200 |

Morphological and Density Analysis

The effect of varying the aqueous/organic ratio on particle morphology and density. Specifically, decreasing the aqueous/organic ratio results in encapsulation of fewer water droplets per microparticle. Encapsulation of fewer droplets should lead to more dense particles (Table 5). The optimal ratio that minimizes surface defects and particle density was being assessed. Interestingly, the internal pore size increased drastically when high aqueous/organic ratios were employed in conjunction with rapid precipitation; whereas lower ratios were associated with more honeycomb structures. We hypothesize that high ratios of aqueous/organic phase lead to large numbers of entrapped water droplets that coalesce under the compressive forces associated with rapid solvent extraction and polymer precipitation; whereas the lower Example 10

Fabrication of Hollow Microparticles: Parameter Manipulation

Methods

General Preparation of Hollow Microparticles

PLGA was weighed out, placed into a scintillation vial, and dissolved by addition of methylene chloride to the desired concentration (typically 5 wt/vol %). This solution was then poured into an aqueous solution containing PVA (0.1-2 wt/vol %). Sometimes this solution contains a salt such as sodium chloride or ammonium carbonate (0.5 wt %). The water to organic phase ratio varies from 0.05 to 0.5. The water-in-oil emulsion was subsequently emulsifed at room temperature and immediately poured into a second aqueous solution containing PVA (and sometimes a salt), and homogenized for an additional five minutes. Particles were allowed to harden by the evaporation/precipitation method. Once hardened, particles were collected by centrifugation (3500×g for five minutes), washed five times with distilled water, and freeze dried to yield a white powder.

Density Measurements

Bulk density measurements were determined using tap density (Sotax). Briefly, approximately 10 mL of particles were placed into a graduate cylinder, which was tapped at a rate of 250 taps/min. The particles were tapped until the change in particle volume was less than 2 mL. The final tapped powder was subsequently weighed and the tapped density determined. The volume of gas within the porous particles was determined by using the densities for hollow and solid microparticles of similar size distributions, respectively. For example, for a 1 gram sample, a hollow microparticle with a density of 0.072 g/mL would occupy 13.89 mL, whereas a solid microparticle (of similar size) with a density of 0.411 g/mL would occupy a volume of 2.433 mL. Therefore, the gas fraction of the hollow microparticles was 13.89-2.433 or 11.457 mL of gas/gram of particle.

Oxygen Transfer Kinetics

To determine the rate of oxygen transfer to deoxyhemoglobin, the change in oxyhemoglobin saturation was monitored after addition of polymer microparticles to a beaker of donated human blood under convective motion. Briefly, a 50 mL aliquot of human blood was desaturated using bubbled nitrogen gas to a goal oxyhemoglobin saturation of <60%. Maximum oxygen content in 50 mL blood and actual oxygen content of the desaturated blood was calculated according to Eqn 2. The oxygen deficit was calculated and used to determine the volume of particles required to achieve near 100% oxyhemoglobin saturation. The oxygen deficit (in mL O2) was administered by addition of microparticles as the change in oxyhemoglobin saturation was measured continuously (PediaSat Oximetry Catheter, Edwards Lifesciences).

$$CaO_2 = (1.34 \times Hgb \times SaO_2) + (PaO_2 \times 0.0031) \times \text{Volume-Factor} \quad \text{Eqn 2.}$$

Results and Discussion

We optimized the percent yield of hollow microparticles prepared in accordance with the methods described herein by identifying the optimal manufacturing parameters. We also optimized the washing procedure to separate and enrich the hollow fraction from the honeycomb and solid fractions. The resultant product was a low density, polymeric microparticle with a uniform hollow core-shell structure.

Effect of Processing Parameters on Particle Morphology

The primary water in oil emulsion (w/o) was prepared by first emulsifying the aqueous phase in the presence of PLGA dissolved in an appropriate solvent (typically dichloromethane). The size of the w/o emulsion correlates to the internal diameter of the final microparticle. As such, control of the stability and size of the primary emulsion were required for high encapsulation efficiencies. Emulsion stability can be controlled by addition of surfactant to the aqueous or organic phase, or by addition of salts to the aqueous phase to balance the effects of Ostwald ripening. The size of the emulsion was controlled primarily through the viscosity of the solution (which is a function of the molecular weight and concentration of the PLGA and surfactant, the ratio of the aqueous-to organic phase, and the speed of homogenization. Formation of uniformly hollow microparticles is typically accomplished by matching the average size of the primary w/o emulsion to average size of the secondary emulsion. If the average size of the primary emulsion was smaller than the secondary emulsion, microparticles with a honeycomb internal morphology were formed. If the average size of the primary emulsion is greater than the size of the secondary emulsion, microparticles with solid cores will predominate. Alternatively, one can fabricate honeycomb particles (i.e. PLGA oil droplet encasing multiple water droplets) and identify the appropriate processing conditions that enable internal bubble coalescence, which would then yield a uniformly hollow microparticle.

Effect of Varying Primary Emulsion Droplet Size

The primary emulsion droplet size was varied by increasing the power of the dispersive force. Sonication was used to generate droplets 1 micron in diameter, whereas homogenization was used to produce w/o emulsions with larger droplet sizes (ranges from 2-10 microns). Representative experiments are shown in Table 6. Microparticles with multiple internal cavities (i.e. honeycomb) were produced when the droplet size of the primary emulsion is substantially smaller than the droplet size of the secondary emulsion; whereas microparticles with a single internal cavity were produced when the droplet size of the primary and secondary emulsions were similar.

TABLE 6

| Label | Formulation | 1-speed (rpm) | 1-Time (s) | PVA in W1 (% wt) | PLGA (wt/vol %) | Salt in W1 (wt %) | Water/DCM |
|---|---|---|---|---|---|---|---|
| Effect of varying primary emulsion droplet size | | | | | | | |
| | 43-649-55-1 | Sonicated | max@10 sec | 0 | 5 | 0.5 | 0.3 |
| | 43-649-55-3 | 4 | 60 | 0 | 5 | 0.5 | 0.3 |
| | 43-649-55-2 | 6 | 60 | 0 | 5 | 0.5 | 0.3 |
| Effect of varying secondary emulsion droplet size | | | | | | | |
| | 43-649-55-2* | 3 | 60 | 0 | 5 | 0.5 | 0.5 |
| | 43-649-52-2 | 3 | 60 | 0 | 5 | 0.5 | 0.5 |
| | 43-649-55-1* | 3 | 60 | 0 | 5 | 0.5 | 0.5 |
| | 43-649-37-2 | 3 | 60 | 1 | 5 | 0.5 | 0.5 |
| | 43-649-37-3 | 3 | 60 | 1 | 5 | 0.5 | 0.5 |
| | 43-649-42-3 | 6 | 60 | 0.1 | 2.5 | 0.5 | 0.5 |
| | 43-649-42-4 | 6 | 60 | 0.1 | 2.5 | 0.5 | 0.5 |
| Effect of varying aqueous-to-organic ratio | | | | | | | |
| | 43-649-52-1 | 3 | 60 | 0 | 5 | 0.5 | 0.1 |
| | 43-649-52-2 | 3 | 60 | 0 | 5 | 0.5 | 0.5 |

TABLE 6-continued

Effect of varying PLGA concentration

| | | | | | | | |
|---|---|---|---|---|---|---|---|
| 43-649-37-2 | 3 | 60 | 1 | 5 | 0.5 | 0.5 | |
| 43-649-37-4 | 3 | 60 | 1 | 2.5 | 0.5 | 0.5 | |
| 43-649-42-1 | 6 | 60 | 0.1 | 5 | 0.5 | 0.5 | |
| 43-649-42-4 | 6 | 60 | 0.1 | 2.5 | 0.5 | 0.5 | |

Effect of varying PVA content in W1

| | | | | | | | |
|---|---|---|---|---|---|---|---|
| 43-649-57-1 | 3 | 60 | 1 | 5 | 0.5 | 0.3 | |
| 43-649-57-2 | 3 | 60 | 0.1 | 5 | 0.5 | 0.3 | |
| 43-649-57-3 | 3 | 60 | 0.5 | 5 | 0.5 | 0.3 | |
| 43-649-52-3 | 3 | 60 | 0 | 5 | 0.5 | 0.5 | |
| 43-649-37-3 | 3 | 60 | 1 | 5 | 0.5 | 0.5 | |

Effect of varying osmotic pressure

| | | | | | | | |
|---|---|---|---|---|---|---|---|
| 43-649-55-1* | 3 | 60 | 0 | 5 | 0.5 | 0.5 | |
| 43-649-52-3 | 3 | 60 | 0 | 5 | 0.5 | 0.5 | |

| Label | Formulation | 2 speed (rpm) | 2 time (min) | PVA in W2 (wt %) | Salt in W2 (wt %) | Volume of W2 (mL) | DF of W2 | Final Volume (mL) | Salt Type |
|---|---|---|---|---|---|---|---|---|---|
| | Effect of varying primary emulsion droplet size | | | | | | | | |
| | 43-649-55-1 | 6000 | 5 | 1 | 0.5 | 200 | 1 | 200 | Ammonium Carbonate |
| | 43-649-55-3 | 6000 | 5 | 1 | 0 | 200 | 1 | 200 | Ammonium Carbonate |
| | 43-649-55-2 | 6000 | 5 | 1 | 0.5 | 200 | 1 | 200 | Ammonium Carbonate |
| | Effect of varying secondary emulsion droplet size | | | | | | | | |
| | 43-649-55-2* | 3500 | 5 | 1 | 0 | 200 | 1 | 200 | Ammonium Carbonate |
| | 43-649-52-2 | 4000 | 5 | 1 | 0.5 | 200 | 1 | 200 | Ammonium Carbonate |
| | 43-649-55-1* | 5000 | 5 | 1 | 0 | 200 | 1 | 200 | Ammonium Carbonate |
| | 43-649-37-2 | 3000 | 5 | 1 | 0.5 | 200 | 1 | 200 | Ammonium Carbonate |
| | 43-649-37-3 | 5000 | 5 | 1 | 0.5 | 200 | 1 | 200 | Ammonium Carbonate |
| | 43-649-42-3 | 3000 | 5 | 1 | 0.5 | 200 | 1 | 200 | Sodium Chloride |
| | 43-649-42-4 | 5000 | 5 | 1 | 0.5 | 200 | 1 | 200 | Sodium Chloride |
| | Effect of varying aqueous-to-organic ratio | | | | | | | | |
| | 43-649-52-1 | 4000 | 5 | 1 | 0.5 | 200 | 1 | 200 | Ammonium Carbonate |
| | 43-649-52-2 | 4000 | 5 | 1 | 0.5 | 200 | 1 | 200 | Ammonium Carbonate |
| | Effect of varying PLGA concentration | | | | | | | | |
| | 43-649-37-2 | 3000 | 5 | 1 | 0.5 | 200 | 1 | 200 | Ammonium Carbonate |
| | 43-649-37-4 | 3000 | 5 | 1 | 0.5 | 200 | 1 | 200 | Ammonium Carbonate |
| | 43-649-42-1 | 5000 | 5 | 1 | 0.5 | 200 | 1 | 200 | Sodium Chloride |
| | 43-649-42-4 | 5000 | 5 | 1 | 0.5 | 200 | 1 | 200 | Sodium Chloride |
| | Effect of varying PVA content in W1 | | | | | | | | |
| | 43-649-57-1 | 5500 | 5 | 1 | 0 | 200 | 6 | 1200 | Ammonium Carbonate |
| | 43-649-57-2 | 6000 | 5 | 1 | 0 | 200 | 6 | 1200 | Ammonium Carbonate |
| | 43-649-57-3 | 5500 | 5 | 1 | 0 | 200 | 6 | 1200 | Ammonium Carbonate |
| | 43-649-52-3 | 5000 | 5 | 1 | 0.5 | 200 | 1 | 200 | Ammonium Carbonate |
| | 43-649-37-3 | 5000 | 5 | 1 | 0.5 | 200 | 1 | 200 | Ammonium Carbonate |
| | Effect of varying osmotic pressure | | | | | | | | |
| | 43-649-55-1* | 5000 | 5 | 1 | 0 | 200 | 1 | 200 | Ammonium Carbonate |
| | 43-649-52-3 | 5000 | 5 | 1 | 0.5 | 200 | 1 | 200 | Ammonium Carbonate |

Effect of Varying Secondary Emulsion Droplet Size

Figure 23:
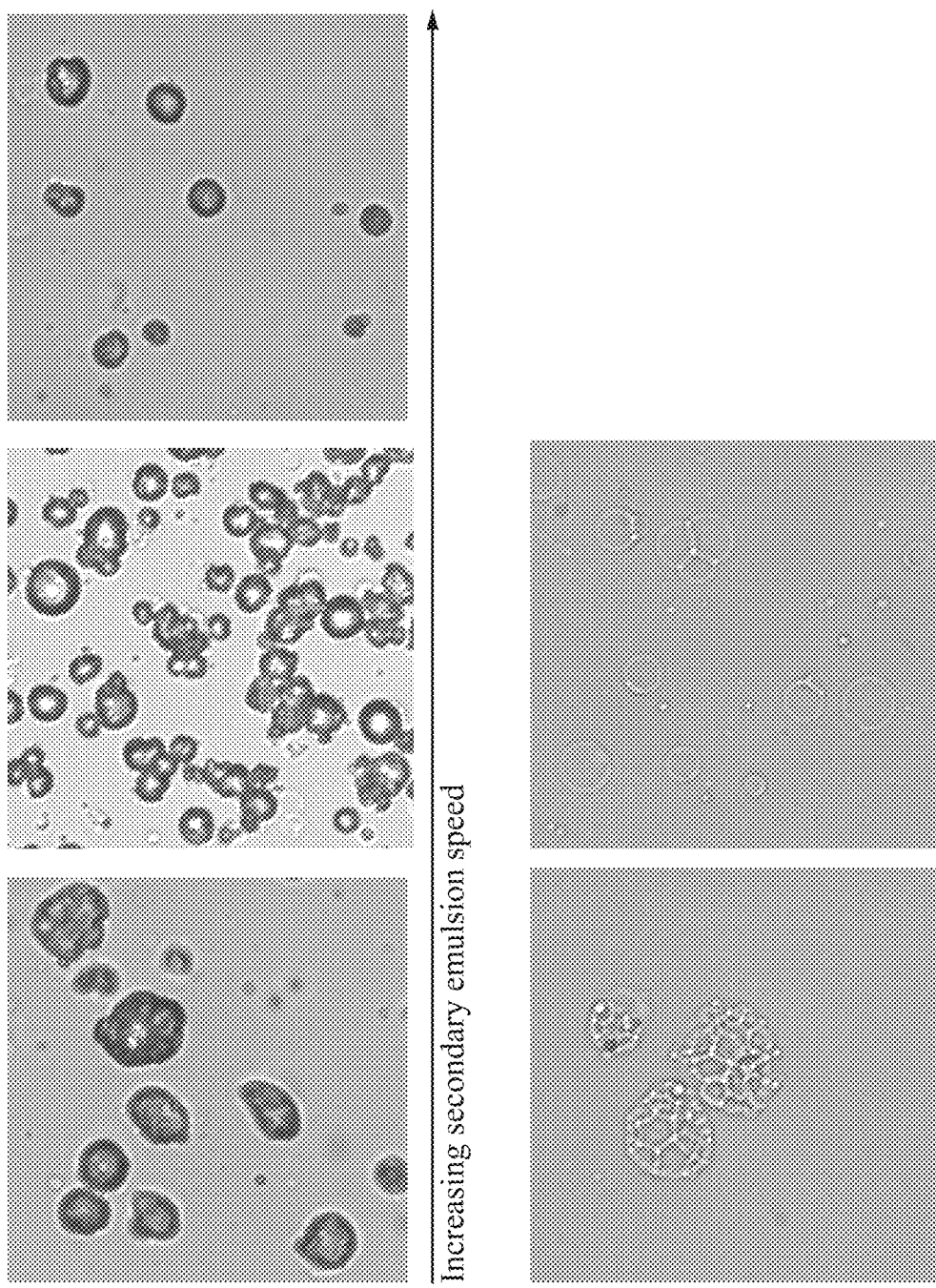
FIG. 23. Varying the secondary emulsion droplet size produces microparticles with varying internal morphologies and sizes. Low secondary speed results in large microparticles that possess honeycomb-like internal morphologies. As the secondary speed is increased, the particle diameter decreases and the internal morphology transforms from mulitcore to single core. Images are post-freeze drying.

Increasing the secondary emulsion speed changes both the microparticle size and internal morphology (FIG. 23). Just as above, if the droplet size of the primary emulsion is much smaller than the droplet size of the secondary emulsion, then large microparticles with a honeycomb-like structure will be formed (FIG. 23A). As the secondary speed was increased, the diameter of the primary emulsion approaches that of the secondary and microparticles with larger internal cavities were formed. (FIGS. 23B,23C). However, the secondary speed also controls the diameters of the final microparticle, with faster speeds yield smaller microparticles.

Effect of Varying PLGA and PVA Concentration

The concentrations of PLGA (in oil phase) and PVA (in W1) play critical roles in regulating the viscosity of the primary emulsion. Changing either one of these parameters will change the droplet size of the primary emulsion (assuming constant homogenization speed or power). At high PVA concentrations (1 wt %), honeycomb-like structures were favored at higher PLGA concentrations, whereas hollow cores were observed at lower PLGA concentrations. However, at low PVA concentrations (0.1%), hollow cores were observed regardless of PLGA concentration. In the former case, the high concentration of PLGA increases the viscosity of the oil phase during solvent evaporation, which hinders coalescence of the internal water droplets. Internal coalescence was further inhibited by the presence of high PVA concentrations, which are known to reduce the surface tension. When the concentration of PVA was significantly reduced to 0.1%, internal coalescence occurs and microparticles with uniform hollow cores were produce, regardless of the PLGA concentration.

Effect of Varying Osmotic Pressure Between W1 and W2

Figure 24:
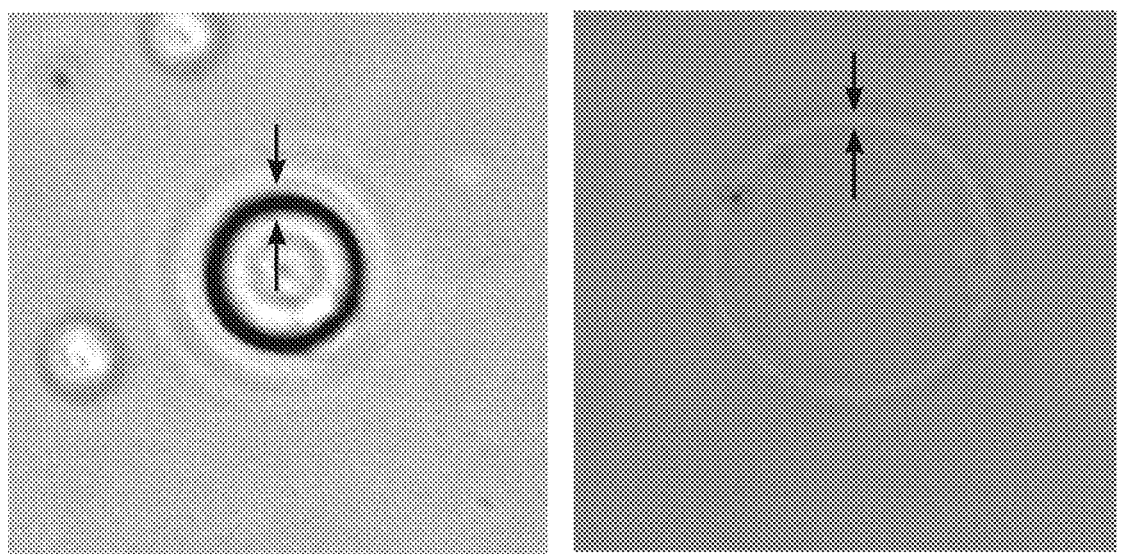
FIG. 24. Varying the osmotic pressure difference between W1 and W2 can be used to control shell thickness.

Varying the osmotic pressure between W1 and W2 serves two purposes: it prevents dewetting and allows one to tune the shell thickness (and by default particle size). Both of these situations requires a higher salt concentration in W1, which drives water into the emulsion. We found that the concentration of the gradient as well as the rate of solvent evaporation and polymer precipitation played significant roles in this process. If PLGA is precipitated quickly, shell thickness if virtually unchanged, regardless of salt concentration. However, if the PLGA is allowed to precipitate over several hours, the shell thickness can be reduced at the expense of increasing particle size (FIG. 24).

Method of Concentration of Microparticles

As previously mentioned, fabrication of microparticles via homogenization yields a mixture of hollow, honeycomb, and solid fractions. The hollow microparticles are less dense and can be easily separated from the bulk of the solid fraction by centrifugation. During this process, the more dense solid fraction pellets first with the hollow fraction settling at the top. Simple vortexing of the pellet preferentially resuspends the less packed hollow fraction while keeping the compact solid fraction tightly pelleted. The hollow particles were subsequently freeze-dried to yield the final product.

Oxygen Transfer

Figure 25:
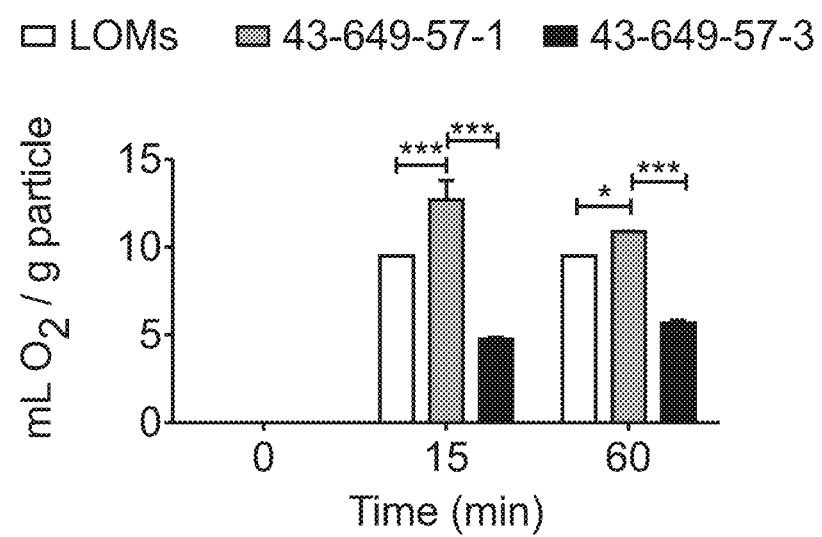
FIG. 25. PLGA microparticles deliver similar volumes of oxygen to deoxygenated blood as lipid-based microbubbles.

Selected hollow PLGA microparticles (densities=0.05 to 1.4 g/mL) were tested for their ability to transfer oxygen gas to deoxygenated blood (FIG. 25). Oxygen delivery correlated with particle density, with particles having lower densities delivering the greatest volume of gas. Importantly, PLGA microparticles delivered more oxygen than LOMs on a mass basis (11 mL $O_2$/g vs 9.5 mL $O_2$/g).

Other Embodiments

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A method of delivering a gas to a subject in need thereof, the method comprising administering to the subject a pharmaceutical composition comprising a gas-filled particle and a pharmaceutically acceptable excipient, wherein the gas-filled particle comprises a stabilized crosslinked membrane encapsulating one or more gases, wherein the one or more gases is not a fluorinated gas, perfluorocarbon based liquid, or hemoglobin, and wherein the stabilized membrane is a crosslinked membrane, and wherein the gas-filled particle releases the encapsulated gas within a period of time of less than 1 minute following the administration, thereby delivering the gas to the subject in need thereof.

2. The method of claim 1, wherein the pharmaceutical composition is administered to the subject.

3. The method of claim 1, wherein the pharmaceutical composition is topically administered directly to an organ of the subject.

4. The method of claim 3, wherein the organ is skin and a skin disorder or wound is treated.

5. The method of claim 4, wherein the wound is a burn.

6. The method of claim 1, wherein the subject has a neurological disease, and the pharmaceutical composition is administered in an effective amount to deliver the gas to the brain of the subject.

7. The method of claim 1, wherein the crosslinked membrane is non-covalently crosslinked.

8. The method of claim 7, wherein the non-covalently crosslinked membrane comprises a non-covalently crosslinked alginate.

9. The method of claim 1, wherein the stabilized membrane comprises a polymer.

10. The method of claim 9, wherein the polymer is a carbohydrate, a protein or a synthetic polymer, or a natural polymer.

11. The method of claim 1, further comprising a sheath membrane between the stabilized membrane and the encapsulated gas.

12. The method of claim 1, wherein the stabilized membrane is stabilized with one or more stabilizing agents.

13. The method of claim 1, wherein the particle is in medium as a suspension for storage or in a powder form for storage.

14. The method of claim 13, wherein the medium comprises a viscosity enhancing agent.

15. The method of any one of claims 1, 2, and 7-14, wherein the composition or suspension is delivered to the subject at a flow rate of between 10 mL/min to 400 mL/min.

16. The method of any one of claims 1, 2, 3-6, and 7-14, wherein the pharmaceutical composition is formulated in a suspension, and wherein the suspension comprises at least one viscosity enhancer in an amount between 25% and 80% by weight.

* * * * *